(12) United States Patent
Li et al.

(10) Patent No.: US 11,345,701 B1
(45) Date of Patent: *May 31, 2022

(54) KRAS MUTANT PROTEIN INHIBITORS

(71) Applicant: Jacobio Pharmaceuticals Co., Ltd., Beijing (CN)

(72) Inventors: Amin Li, Beijing (CN); Sujing Li, Beijing (CN); Peng Wang, Beijing (CN); Chaojie Dang, Beijing (CN); Dan Liu, Beijing (CN)

(73) Assignee: JACOBIO PHARMACEUTICALS CO., LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/407,249

(22) Filed: Aug. 20, 2021

Related U.S. Application Data

(63) Continuation of application No. 17/218,568, filed on Mar. 31, 2021, now Pat. No. 11,161,847, which is a continuation of application No. PCT/CN2021/080995, filed on Mar. 16, 2021.

(51) Int. Cl.
*C07D 471/04* (2006.01)

(52) U.S. Cl.
CPC .................. *C07D 471/04* (2013.01)

(58) Field of Classification Search
CPC ................................... C07D 471/04
USPC ..................................... 514/252.16
See application file for complete search history.

(56) References Cited

U.S. PATENT DOCUMENTS

| | | | |
|---|---|---|---|
| 10,519,146 B2 * | 12/2019 | Lanman | C07D 487/08 |
| 11,161,847 B2 * | 11/2021 | Li | C07D 471/04 |
| 2019/0374542 A1 | 12/2019 | Allen et al. | |

FOREIGN PATENT DOCUMENTS

| | | |
|---|---|---|
| CN | 111205286 | 5/2020 |
| WO | 2018119183 | 6/2018 |
| WO | 2018217651 | 11/2018 |
| WO | 2019051291 | 3/2019 |
| WO | 2019213516 | 11/2019 |
| WO | 2020102730 | 5/2020 |

OTHER PUBLICATIONS

Lanman et al. "Discovery of a covalent inhibitor of KRASG12C (AMG 510) for the treatment of solid tumors." J Med Chem. Jan. 9, 2020;63(1):52-65.
This application is a Continuation of U.S. Appl. No. 17/218,568, filed Mar. 31, 2021.

* cited by examiner

*Primary Examiner* — Niloofar Rahmani
(74) *Attorney, Agent, or Firm* — Robin L. Teskin; Baker, Donelson, Bearman, Caldwell & Berkowitz, PC

(57) ABSTRACT

The invention relates to a KRAS mutant protein inhibitors of formula (I), a composition containing the inhibitors and the use thereof.

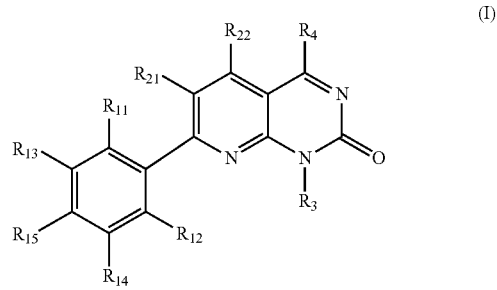

10 Claims, 2 Drawing Sheets

KRAS MUTANT PROTEIN INHIBITORS

CROSS-REFERENCE TO RELATED APPLICATIONS

This application is a continuation application of U.S. application Ser. No. 17/218,568, filed Mar. 31, 2021, which is a continuation of Int'l Appl. No. PCT/CN2021/080995, filed Mar. 16, 2021, which claims priority to Int'l Appl. No. PCT/CN2020/087943, filed Apr. 30, 2020, and Int'l Appl. No. PCT/CN2020/079667, filed Mar. 17, 2020, the disclosures of each of which are hereby incorporated by reference in their entireties.

TECHNICAL FIELD

The invention relates to a KRAS mutant protein inhibitors, a composition containing the inhibitors and the use thereof.

BACKGROUND ART

RAS represents a population of 189 amino acid monomeric globular proteins (21 kDa molecular weight) that are associated with the plasma membrane and bind to GDP or GTP, and RAS acts as a molecular switch. When the RAS contains bound GDP, it is in a stationary or closed position and is "inactive". When cells are exposed to certain growth-promoting stimuli, RAS is induced to exchange their bound GDP for GTP. In the case of binding to GTP, RAS is "opened" and is capable of interacting with other proteins (its "downstream targets") and activating the proteins. The RAS protein itself has an inherently low ability to hydrolyze GTP back to GDP, thereby turning itself into a closed state. Closing RAS requires an exogenous protein called GTPase activating protein (GAP) that interacts with RAS and greatly accelerates the conversion of GTP to GDP. Any mutation in RAS that affects its ability to interact with GAP or convert GTP back to GDP will result in prolonged protein activation, and thus conduction to the cell to inform its signaling of continued growth and division. Since these signals cause cell growth and division, over-activated RAS signaling can ultimately lead to cancer.

Structurally, the RAS protein contains a G domain responsible for the enzymatic activity of RAS, guanine nucleotide binding and hydrolysis (GTPase reaction). It also contains a C-terminal extension called the CAAX cassette, which can be post-translationally modified and responsible for targeting the protein to the membrane. The G domain contains a phosphate binding ring (P-ring). The P-loop represents a pocket of a binding nucleotide in a protein, and this is a rigid portion of a domain with conserved amino acid residues necessary for nucleotide binding and hydrolysis (glycine 12 and lysine 16). The G domain also contains a so-called switch I region (residues 30-40) and a switch II region (residues 60-76), both of which are dynamic parts of the protein, since the dynamic portion is converted between stationary and loaded states. The ability is often expressed as a "spring loaded" mechanism. The primary interaction is the hydrogen bond formed by threonine-35 and glycine-60 with the gamma-phosphate of GTP, which maintains the active conformation of the switch 1 region and the switch 2 region, respectively. After hydrolysis of GTP and release of phosphate, the two relax into an inactive GDP conformation.

The most notable members of the RAS subfamily are HRAS, KRAS and NRAS, which are primarily involved in many types of cancer. Mutation of any of the three major isoforms of the RAS gene (HRAS, NRAS or KRAS) is one of the most common events in human tumor formation. Approximately 30% of all tumors in human tumors were found to carry some mutations in the RAS gene. It is worth noting that KRAS mutations were detected in 25%-30% of tumors. In contrast, the rate of carcinogenic mutations in NRAS and HRAS family members was much lower (8% and 3%, respectively). The most common KRAS mutations were found at residues G12 and G13 in the P-loop as well as at residue Q61.

G12C is a frequently occurring KRAS gene mutation (glycine-12 is mutated to cysteine). This mutation has been found in about 13% of cancers, about 43% in lung cancer, and almost 100% in MYH-associated polyposis (familial colon cancer syndrome). However, targeting this gene with small molecules is a challenge.

Thus, despite advances in this field, there remains a need in the art for improved compounds and methods for treating cancer, such as by inhibiting KRAS, HRAS or NRAS. The present invention fulfills this need and provides other related advantages.

SUMMARY OF INVENTION

In one aspect, provided herein is a compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof:

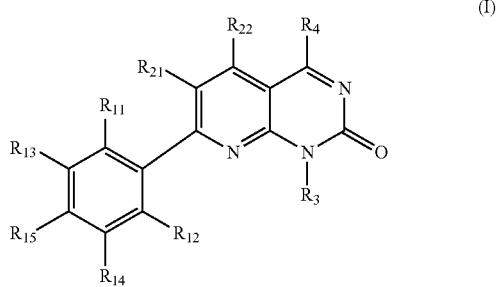

Wherein:

$R_{11}$, $R_{12}$, $R_{13}$, $R_{14}$ or $R_{15}$ is independently selected from halogen, —$C_{1-6}$alkyl, —$C_{2-6}$alkenyl, —$C_{2-6}$alkynyl, hetero$C_{2-6}$alkyl, —CN, —$OC_{1-6}$alkyl, —$SC_{1-6}$alkyl, —$NR_5R_6$, —C(=O)$R_5$, —C(=O)$OR_5$, —OC(=O)$R_5$, —C(=O)$NR_5R_6$, —$NR_5$C(=O)$R_6$, —$NR_5SO_2R_6$, —$SO_2R_5$, —S(=O)$_2NR_5R_6$, —POR$_5R_6$, —$C_{3-6}$carbocyclic, 3- 6 membered heterocyclic, —$C_{6-10}$aryl, or 5-10 membered heteroaryl, wherein, said —$C_{1-6}$alkyl, —$C_{2-6}$alkenyl, —$C_{2-6}$alkynyl, hetero$C_{2-6}$alkyl, —$OC_{1-6}$alkyl, —$SC_{1-6}$alkyl, —$NR_5R_6$, —C(=O)$R_5$, —C(=O)$OR_5$, —OC(=O)$R_5$, —C(=O)$NR_5R_6$, —$NR_5$C(=O)$R_6$, —$NR_5SO_2R_6$, —$SO_2R_5$, —S(=O)$_2NR_5R_6$, —POR$_5R_6$, —$C_{3-6}$carbocyclic, 3- 6 membered heterocyclic, —$C_{6-10}$aryl or 5-10 membered heteroaryl is independently optionally substituted with one or more substituents selected from halogen, —$C_{1-6}$alkyl, —$C_{2-6}$alkenyl, —$C_{2-6}$alkynyl, hetero$C_{2-6}$alkyl, —CN, oxo, —$OC_{1-6}$alkyl, —$SC_{1-6}$alkyl, —$NR_5R_6$, —C(=O)$R_5$, —C(=O)$OR_5$, —OC(=O)$R_5$, —C(=O)$NR_5R_6$, —$NR_5$C(=O)$R_6$, —$NR_5SO_2R_5$, —$SO_2R_5$, —S(=O)$_2NR_5R_6$, —POR$_5R_6$, —$C_{3-6}$carbocyclic, 3-6 membered heterocyclic, —$C_{6-10}$aryl, or 5-10 membered heteroaryl; said heterocyclic or heteroaryl at each occurrence independently contains 1, 2, 3 or 4 heteroatoms selected from N, O, S, S=O or S(=O)$_2$;

$R_{21}$ or $R_{22}$ is independently selected from hydrogen, halogen, —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3- 6 membered heterocyclic, —C$_{6-10}$aryl, or 5-10 membered heteroaryl, wherein, said —C$_{1-6}$alkyl, —C$_{2-6}$alkenyl, —C$_{2-6}$alkynyl, heteroC$_{2-6}$alkyl, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3- 6 membered heterocyclic, —C$_{6-10}$aryl or 5-10 membered heteroaryl is independently optionally substituted with one or more substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; said heterocyclic or heteroaryl at each occurrence independently contains 1, 2, 3 or 4 heteroatoms selected from N, O, S, S=O or S(=O)$_2$;

$R_3$ is selected from —C$_{1-14}$alkyl, —C$_{2-14}$alkenyl, —C$_{2-14}$alkynyl, —C$_{6-10}$aryl, 5-10 membered heteroaryl, 3-14 membered heterocyclic, —C$_{3-14}$carbocyclic,

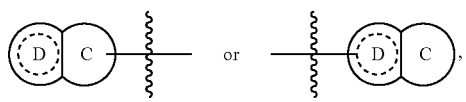

each ring C at each occurrence is independently selected from a C$_{3-14}$ carbocyclic ring or a 3-14 membered heterocyclic ring, each ring D at each occurrence is independently selected from a C$_{6-10}$ aryl ring or a 5-10 membered heteroaryl ring, wherein, said —C$_{1-14}$alkyl, —C$_{2-14}$alkenyl, —C$_{2-14}$alkynyl, —C$_{6-10}$aryl, 5-10 membered heteroaryl, 3-14 membered heterocyclic, —C$_{3-14}$carbocyclic,

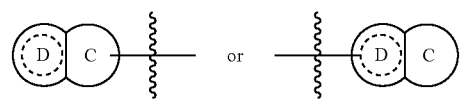

is independently optionally substituted with 1R$_{31}$, 2R$_{31}$, 3R$_{31}$, 4R$_{31}$, 5R$_{31}$ or 6R$_{31}$; said heterocyclic, heterocyclic ring, heteroaryl or heteroaryl ring at each occurrence independently contains 1, 2, 3 or 4 heteroatoms selected from N, O, S, S=O or S(=O)$_2$;

Each R$_{31}$ at each occurrence is independently selected from halogen, —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3- 6 membered heterocyclic, —C$_{6-10}$aryl, or 5-10 membered heteroaryl, wherein, said —C$_{1-6}$alkyl, —C$_{2-6}$alkenyl, —C$_{2-6}$alkynyl, heteroC$_{2-6}$alkyl, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3- 6 membered heterocyclic, —C$_{6-}$ $_{10}$aryl, or 5-10 membered heteroaryl is independently optionally substituted with one or more substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; said heterocyclic or heteroaryl at each occurrence independently contains 1, 2, 3 or 4 heteroatoms selected from N, O, S, S=O or S(=O)$_2$;

R$_4$ is selected from

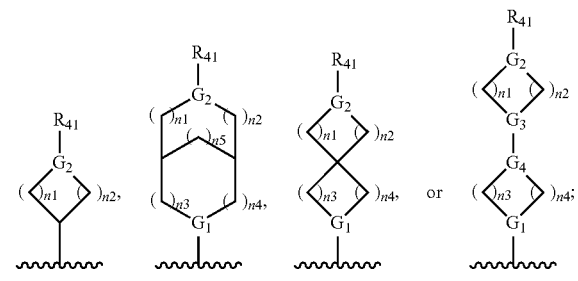

Each G$_1$, G$_2$, G$_3$ or G$_4$ at each occurrence is independently selected from N or CH;

Each n1, n2, n3, n4 or n5 at each occurrence is independently selected from 0, 1, 2, 3, 4, 5 or 6, provided that n1 and n2 is not 0 at the same time, n3 and n4 is not 0 at the same time;

Said

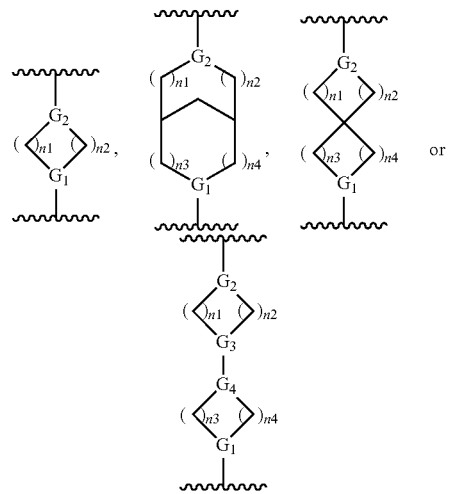

is independently optionally substituted with 1 R$_{42}$, 2 R$_{42}$, 3 R$_{42}$, 4 R$_{42}$, 5 R$_{42}$ or 6 R$_{42}$;

Each R$_{41}$ at each occurrence is independently selected from

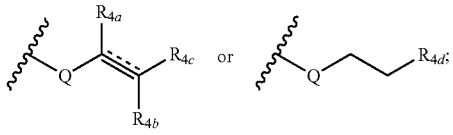

Each Q at each occurrence is independently selected from C(=O), NR$_5$C(=O), S(=O)$_2$ or NR$_5$S(=O)$_2$;

═══ in

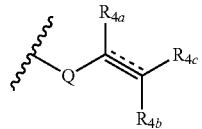

is selected from ═ or ≡;

when ═══ is ═, R$_{4a}$, R$_{4b}$ or R$_{4c}$ is independently selected from hydrogen, halogen, —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl, wherein, said —C$_{1-6}$alkyl, —C$_{2-6}$alkenyl, —C$_{2-6}$alkynyl, heteroC$_{2-6}$alkyl, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl is independently optionally substituted with one or more substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; said heterocyclic or heteroaryl at each occurrence independently contains 1, 2, 3 or 4 heteroatom(s) selected from N, O, S, S=O or S(=O)$_2$; or when ═══ is ═, R$_{4a}$ is selected from hydrogen, halogen, —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl, wherein, said —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl is independently optionally substituted with one or more substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; and R$_{4b}$ and R$_{4c}$ together with the carbon to which they are both attached form a C$_{3-10}$ carbocyclic ring or a 3-10 membered heterocyclic ring, said C$_{3-10}$ carbocyclic ring or said 3-10 membered heterocyclic ring is optionally substituted with one or more substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_5$, —C$_{3-6}$carbocyclic, 3-6 membered heterocyclic, —C$_{6-10}$aryl, or 5-10 membered heteroaryl; said heterocyclic, heterocyclic ring, heteroaryl or heteroaryl ring at each occurrence independently contains 1, 2, 3 or 4 heteroatoms selected from N, O, S, S=O or S(=O)$_2$; or when ═══ is ═, R$_{4a}$ and R$_{4c}$ with the carbons to which they respectively are attached form a C$_{3-10}$ carbocyclic ring or a 3-10 membered heterocyclic ring, said C$_{3-10}$ carbocyclic ring or said 3-10 membered heterocyclic ring is optionally substituted with one or more substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; and R$_{4b}$ is selected from hydrogen, halogen, —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_5$, —C$_{3-6}$carbocyclic, 3-6 membered heterocyclic, —C$_{6-10}$aryl, or 5-10 membered heteroaryl, said —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl is independently optionally substituted with one or more substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$. —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; said heterocyclic, heterocyclic ring, heteroaryl or heteroaryl ring at each occurrence independently contains 1, 2, 3 or 4 heteroatoms selected from N, O, S, S=O or S(=O)$_2$;

when ═══ is ≡, R$_{4a}$ is absent, R$_{4b}$ is absent, R$_{4c}$ is selected from hydrogen, halogen, —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl, wherein, said —C$_{1-6}$alkyl, —C$_{2-6}$alkenyl, —C$_{2-6}$alkynyl, heteroC$_{2-6}$alkyl, —OC$_{1-6}$alkyl, —SC$_{1-6}$alkyl, —NR$_5$R$_6$. —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl is independently optionally substituted with one or more substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; said heterocyclic or heteroaryl at each occurrence independently contains 1, 2, 3 or 4 heteroatoms selected from N, O, S, S=O or S(=O)$_2$;

$R_{4d}$ is halogen;

Each $R_{42}$ at each occurrence is independently selected from halogen, —$C_{1-6}$alkyl, —$C_{2-6}$alkenyl, —$C_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl, wherein, said —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl is independently optionally substituted with one or more substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl;

Optionally, two $R_{42}$ together with the atom(s) to which they are both or respectively attached form a $C_{3-6}$ carbocyclic or 3-6 membered heterocyclic ring, said $C_{3-6}$ carbocyclic or said 3-6 membered heterocyclic ring is independently optionally substituted with one or more substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —PO(R$_5$)$_2$, —C$_{3-6}$carbocyclic, 3-6 membered heterocyclic, —C$_{6-10}$aryl, or 5-10 membered heteroaryl; said heterocyclic, heterocyclic ring, heteroaryl or heteroaryl ring at each occurrence independently contains 1, 2, 3 or 4 heteroatoms selected from N, O, S, S=O or S(=O)$_2$;

Each $R_5$ or $R_6$ at each occurrence is independently selected from hydrogen or —C$_{1-6}$alkyl; or $R_5$ and $R_6$ together with the atom(s) to which they are both or respectively attached form a 3-10 membered heterocyclic ring, said 3-10 membered heterocyclic ring is optionally further contains 1, 2, 3 or 4 heteroatoms selected from N, O, S, S(=O) or S(=O)$_2$, and said 3-10 membered heterocyclic ring is independently optionally substituted with 1 R$_{51}$, 2 R$_{51}$, 3 R$_{51}$, 4 R$_{51}$, 5 R$_{51}$ or 6 R$_{51}$;

Each $R_{51}$ at each occurrence is independently selected from halogen, —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_7$R$_8$, —C(=O)R$_7$, —C(=O)OR$_7$, —OC(=O)R$_7$, —C(=O)NR$_7$R$_8$, —NR$_7$C(=O)R$_8$, —NR$_7$SO$_2$R$_8$, —SO$_2$R$_7$, —S(=O)$_2$NR$_7$R$_8$, —POR$_7$R$_8$, —C$_{3-6}$carbocyclic, 3- 6 membered heterocyclic, —C$_{6-10}$aryl, or 5-10 membered heteroaryl, wherein, said —C$_{1-6}$alkyl, —C$_{2-6}$alkenyl, —C$_{2-6}$alkynyl, heteroC$_{2-6}$alkyl, —OC$_{1-6}$alkyl, —SC$_{1-6}$alkyl, —NR$_7$R$_8$, —C(=O)R$_7$, —C(=O)OR$_7$, —OC(=O)R$_7$, —C(=O)NR$_7$R$_8$, —NR$_7$C(=O)R$_8$, —NR$_7$SO$_2$R$_8$, —SO$_2$R$_7$, —S(=O)$_2$NR$_7$R$_8$, —POR$_7$R$_8$, —C$_{3-6}$carbocyclic, 3- 6 membered heterocyclic, —C$_{6-10}$aryl, or 5-10 membered heteroaryl is independently optionally substituted with one or more substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_7$R$_8$, —C(=O)R$_7$, —C(=O)OR$_7$, —OC(=O)R$_7$, —C(=O)NR$_7$R$_8$, —NR$_7$C(=O)R$_8$, —NR$_7$SO$_2$R$_8$, —SO$_2$R$_7$, —S(=O)$_2$NR$_7$R$_8$, —POR$_7$R$_8$, —C$_{3-6}$carbocyclic, 3-6 membered heterocyclic, —C$_{6-10}$aryl, or 5-10 membered heteroaryl; said heterocyclic or heteroaryl at each occurrence independently contains 1, 2, 3 or 4 heteroatoms selected from N, O, S, S=O or S(=O)$_2$;

Each $R_7$ or $R_8$ at each occurrence is independently selected from hydrogen or —C$_{1-6}$alkyl.

In some embodiments, provided herein is a compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof:

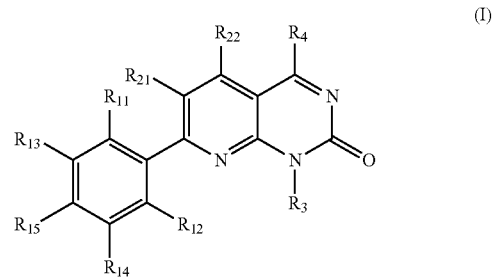

(I)

Wherein:

$R_{11}$, $R_{12}$, $R_{13}$, $R_{14}$ or $R_{15}$ is independently selected from —OH; halogen; —NR$_a$R$_b$; —C$_{1-6}$alkyl; —OC$_{1-6}$alkyl; —C$_{1-6}$alkylene-OH; —C$_{1-6}$alkylene-O—C$_{1-6}$alkyl; —C$_{1-6}$alkyl substituted with halogen, —NH$_2$, —CN or —OH; —O—C$_{1-6}$alkyl substituted with halogen, —NH$_2$, —CN or —OH; —SO$_2$R$_a$; —CN; —C(=O)NR$_a$R$_b$; —C(=O)R$_a$; —OC(=O)R$_a$; —C(=O)OR$_a$; or —C$_{3-6}$carbocyclic;

$R_a$ or $R_b$ is independently selected from hydrogen or —C$_{1-6}$alkyl;

$R_{21}$ is selected from hydrogen; halogen; —C$_{1-6}$alkyl; —C$_{1-6}$alkyl substituted with halogen, —NH$_2$, —CN or —OH; —C$_{2-6}$alkenyl; or —C$_{3-6}$carbocyclic;

$R_{22}$ is selected from hydrogen; halogen; —C$_{1-6}$alkyl; —C$_{1-6}$alkyl substituted with halogen, —NH$_2$, —CN or —OH; —C$_{2-6}$alkenyl; or —C$_{3-6}$carbocyclic;

$R_3$ is selected from —C$_{6-10}$aryl or 5-10 membered heteroaryl, each of 5-10 membered heteroaryl at each occurrence independently contains 1, 2, 3 or 4 heteroatoms selected from N, O or S, each of —C$_{6-10}$aryl or 5-10 membered heteroaryl at each occurrence is independently optionally substituted with 1 R$_{31}$, 2 R$_{31}$, 3 R$_{31}$, 4 R$_{31}$, 5 R$_{31}$ or 6 R$_{31}$;

Each of $R_{31}$ at each occurrence is independently selected from halogen, —C$_{1-6}$alkyl, —CN, —OH, —O—C$_{1-6}$alkyl, —NH$_2$, —NH(C$_{1-6}$alkyl), —N(C$_{1-6}$alkyl)$_2$ or —C$_{3-6}$carbocyclic;

$R_4$ is selected from

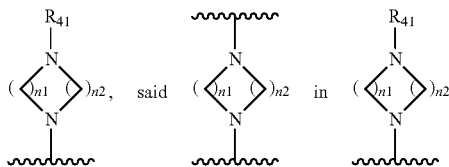

is independently optionally substituted with 1 R$_{42}$, 2 R$_{42}$, 3 R$_{42}$, 4 R$_{42}$, 5 R$_{42}$ or 6 R$_{42}$;

n1 or n2 is independently selected from 1, 2, 3, 4, 5 or 6;

$R_{41}$ is selected from

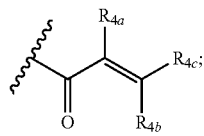

$R_{4a}$, $R_{4b}$ or $R_{4c}$ is independently selected from hydrogen, halogen, —$C_{1-6}$alkyl or —$C_{1-6}$alkylene-N($C_{1-6}$alkyl)$_2$; Each of $R_{42}$ at each occurrence is independently selected from —$C_{1-6}$alkyl; —$C_{1-6}$alkylene-CN or —$C_{1-6}$alkyl substituted with halogen.

In some embodiments, $R_{11}$, $R_{12}$, $R_{13}$, $R_{14}$ or $R_{15}$ is independently selected from —OH; —F; —Cl; —Br; —$NR_aR_b$; —$C_{1-3}$alkyl; —$OC_{1-3}$alkyl; —$C_{1-3}$alkylene-OH; —$C_{1-3}$alkylene-O—$C_{1-3}$alkyl; —$C_{1-3}$alkyl substituted with —F or —Cl; —O—$C_{1-3}$alkyl substituted with —F or —Cl; —$SO_2R_a$; —CN; —C(=O)$NR_aR_b$; —C(=O)$R_a$; —OC(=O)$R_a$; —C(=O)$OR_a$; 3-membered carbocyclic; 4-membered carbocyclic; 5-membered carbocyclic or 6-membered carbocyclic;

$R_a$ or $R_b$ is independently selected from hydrogen or —$C_{1-3}$alkyl.

In some embodiments, $R_{11}$, $R_{12}$, $R_{13}$, $R_{14}$ or $R_{15}$ is independently selected from —OH, —F, —Cl, —NH$_2$, —NHCH$_3$, —N(CH$_3$)$_2$, —CH$_3$, —CH$_2$CH$_3$, —CH$_2$CH$_2$CH$_3$, —CH(CH$_3$)$_2$, —OCH$_3$, —OCH$_2$CH$_3$, —OCH$_2$CH$_2$CH$_3$, —OCH(CH$_3$)$_2$, —CH$_2$OH, —CH$_2$CH$_2$OH, —CH$_2$OCH$_3$, —CHF$_2$, —CH$_2$F, —CF$_3$, —OCH$_2$F, —OCHF$_2$, —OCF$_3$, —SO$_2$CH$_3$, —CN, —C(=O)NH$_2$, —C(=O)CH$_3$, —OC(=O)CH$_3$, —C(=O)OCH$_3$ or 3-membered carbocyclic.

In some embodiments, $R_{11}$, $R_{12}$, $R_{13}$, $R_{14}$ or $R_{15}$ is independently selected from —OH, —F, —Cl, —NH$_2$, —CH$_3$ or —CF$_3$.

In some embodiments, $R_{11}$ is selected from —OH or —NH$_2$; and $R_{12}$, $R_{13}$, $R_{14}$ or $R_{15}$ is independently selected from —F or —Cl.

In some embodiments, $R_1$ is selected from:

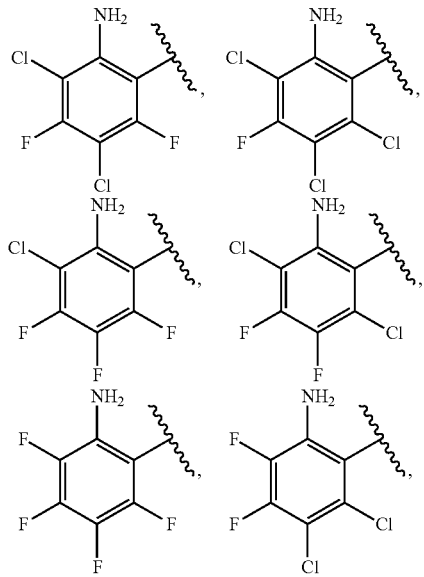

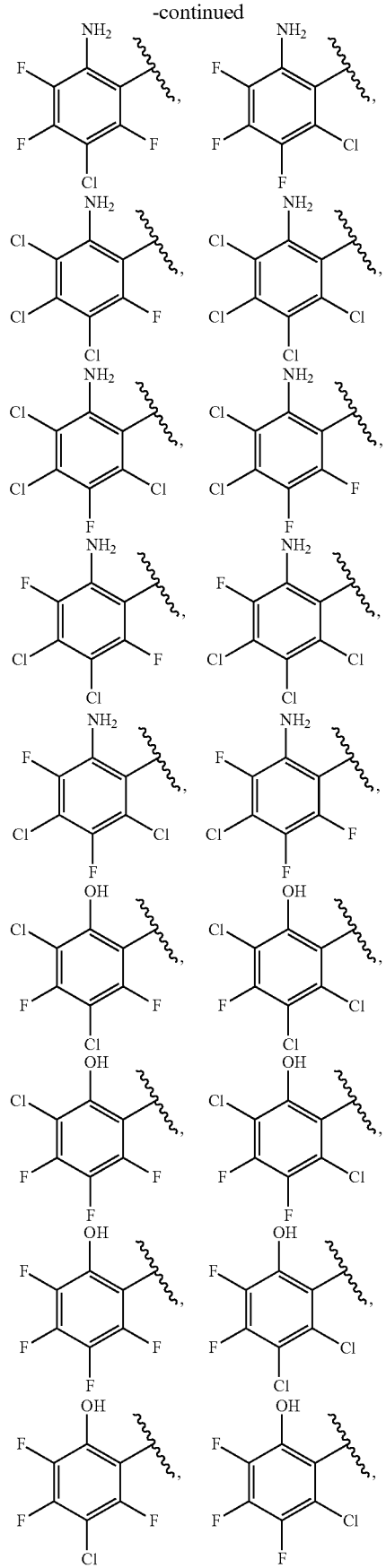

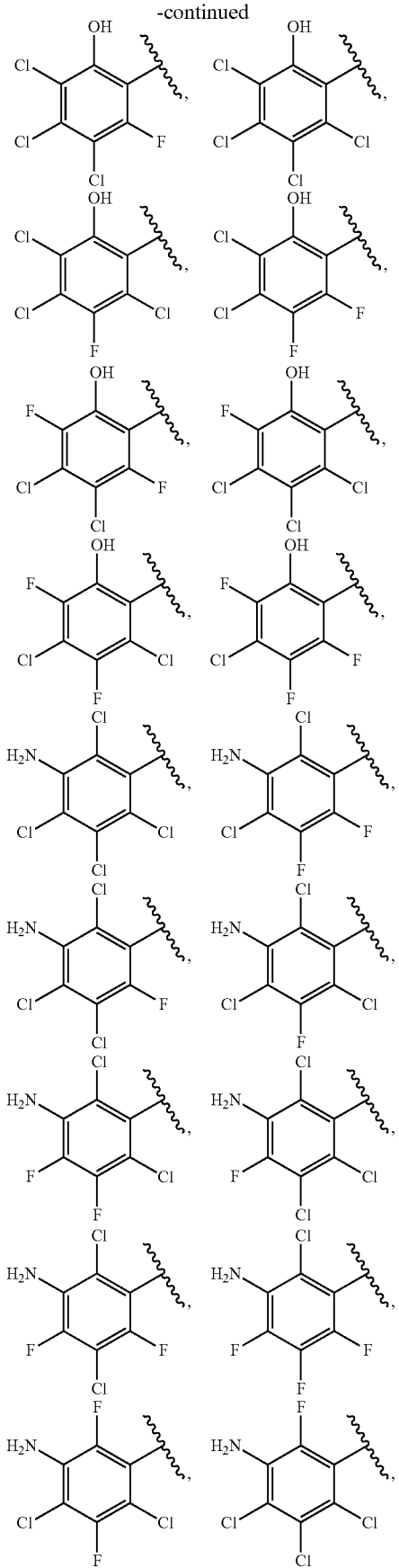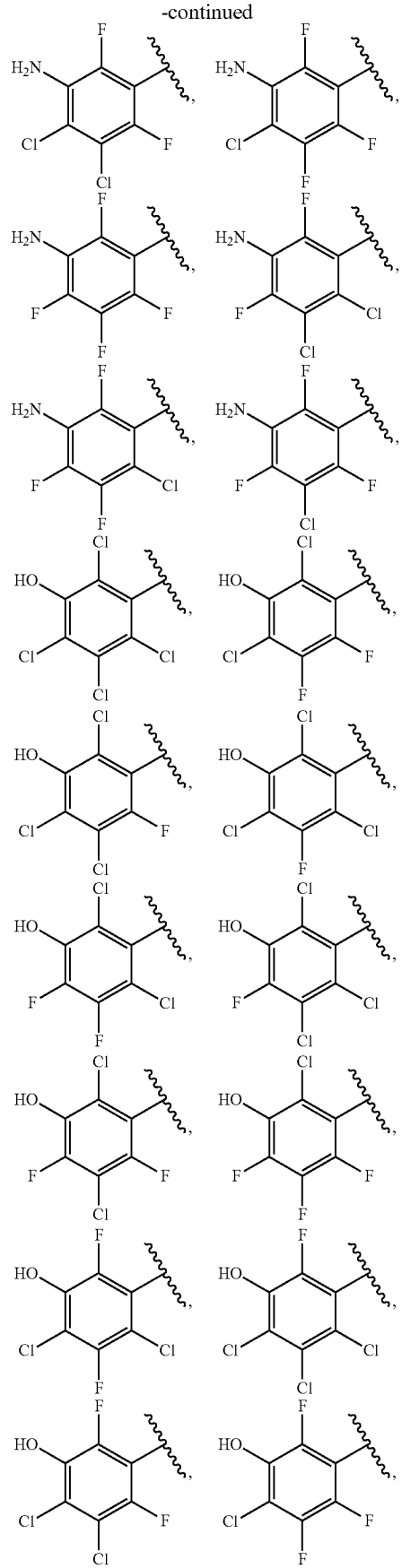

-continued

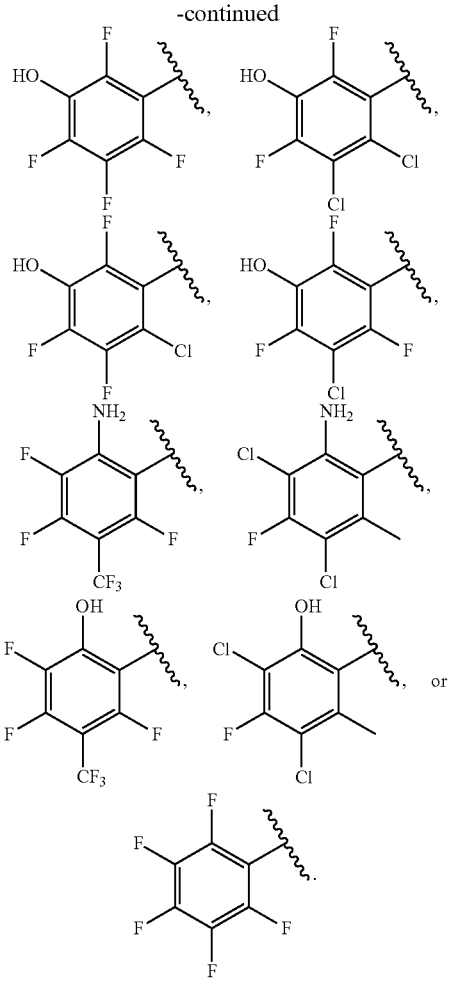

In some embodiments, R$_{21}$ is selected from hydrogen; —F; —Cl; —Br; —C$_{1-3}$alkyl; —C$_{1-3}$alkyl substituted with —F or —Cl; —C$_{2-3}$alkenyl; or —C$_{3-6}$carbocyclic.

In some embodiments, R$_{21}$ is selected from hydrogen; —F; —Cl; methyl; ethyl; propyl; isopropyl; methyl substituted with —F; ethyl substituted with —F; propyl substituted with —F; isopropyl substituted with —F; ethenyl; propenyl; 3 membered carbocyclic; 4 membered carbocyclic; 5 membered carbocyclic; or 6 membered carbocyclic.

In some embodiments, R$_{21}$ is selected from —F or —Cl.

In some embodiments, R$_{21}$ is selected from —F.

In some embodiments, R$_{22}$ is selected from hydrogen; —F; —Cl; —Br; —C$_{1-3}$alkyl; —C$_{1-3}$alkyl substituted with —F or —Cl; —C$_{2-3}$alkenyl; or —C$_{3-6}$carbocyclic.

In some embodiments, R$_{22}$ is selected from hydrogen; —F; —Cl; methyl; ethyl; propyl; isopropyl; methyl substituted with —F; ethyl substituted with —F; propyl substituted with —F; isopropyl substituted with —F; ethenyl; propenyl; 3 membered carbocyclic; 4 membered carbocyclic; 5 membered carbocyclic; or 6 membered carbocyclic.

In some embodiments, R$_{22}$ is hydrogen.

In some embodiments, R$_3$ is selected from phenyl, naphthyl, 5 membered heteroaryl, 6 membered heteroaryl, 7 membered heteroaryl, 8 membered heteroaryl, 9 membered heteroaryl or 10 membered heteroaryl, said heteroaryl at each occurrence independently contains 1, 2 or 3 heteroatoms selected from N or O, said phenyl, naphthyl, 5 membered heteroaryl, 6 membered heteroaryl, 7 membered heteroaryl, 8 membered heteroaryl, 9 membered heteroaryl or 10 membered heteroaryl is independently optionally substituted by 1 R$_{31}$, 2 R$_{31}$, 3 R$_{31}$, 4 R$_{31}$ or 5 R$_{31}$.

In some embodiments, R$_3$ is selected from phenyl or 6 membered heteroaryl, said heteroaryl contains 1 or 2 heteroatoms selected from N, said phenyl or 6 membered heteroaryl at each occurrence is independently optionally substituted with 1 R$_{31}$, 2 R$_{31}$, 3 R$_{31}$ or 4 R$_{31}$.

In some embodiments, R$_3$ is selected from

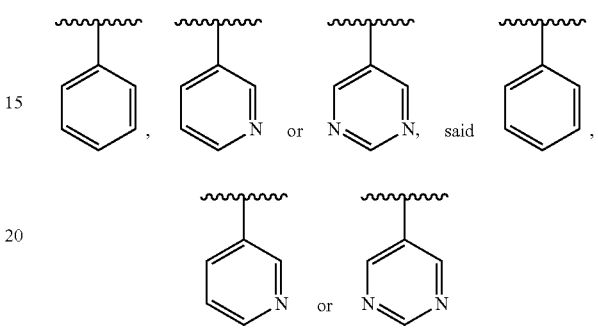

at each occurrence is independently optionally substituted with 1 R$_{31}$, 2 R$_{31}$, 3 R$_{31}$ or 4 R$_{31}$.

In some embodiments, each R$_{31}$ at each occurrence is independently selected from —F, —Cl, —Br, —C$_{1-3}$alkyl, —CN, —OH, —O—C$_{1-3}$alkyl, —NH$_2$, —NH(C$_{1-3}$alkyl), —N(C$_{1-3}$alkyl)$_2$ or —C$_{3-6}$carbocyclic.

In some embodiments, each R$_{31}$ at each occurrence is independently selected from —F, —Cl, methyl, ethyl, propyl, isopropyl, —CN, —OH, methoxy, ethoxy, propoxy, isopropoxy, —NH$_2$, —NHCH$_3$, —NHCH$_2$CH$_3$, —NH(CH$_2$CH$_2$CH$_3$), —NH(CH(CH$_3$)$_2$), —N(CH$_3$)$_2$, —N(CH$_2$CH$_3$)$_2$, —N(CH$_3$)(CH$_2$CH$_3$), 3 membered carbocyclic, 4 membered carbocyclic, 5 membered carbocyclic or 6 membered carbocyclic.

In some embodiments, each R$_{31}$ at each occurrence is independently selected from methyl or isopropyl.

In some embodiments, R$_3$ is selected from

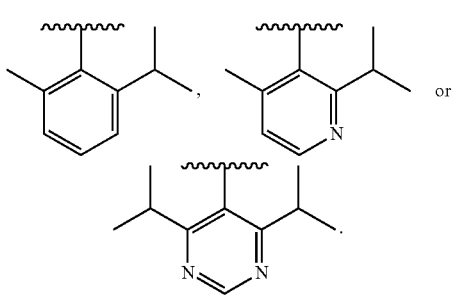

In some embodiments, R$_3$ is

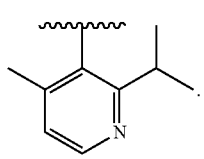

In some embodiments, $R_4$ is selected from

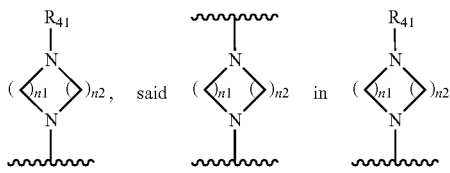

is independently optionally substituted by 1 $R_{42}$, 2 $R_{42}$, 3 $R_{42}$ or 4 $R_{42}$; IDC-37 Cl n1 is selected from 1, 2 or 3;

n2 is selected from 1, 2 or 3.

In some embodiments, $R_4$ is selected from

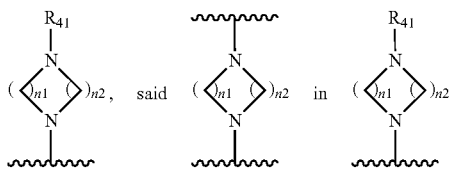

is independently optionally substituted with 1 $R_{42}$ or 2 $R_{42}$;

n1 is selected from 1 or 2;

n2 is selected from 1 or 2.

In some embodiments, $R_4$ is selected from

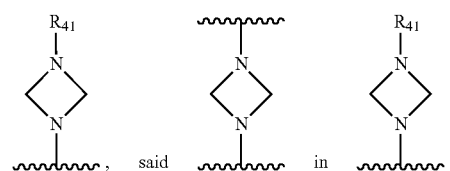

is independently optionally substituted by 1 $R_{42}$ or 2 $R_{42}$.

In some embodiments, $R_{41}$ is selected from

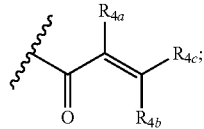

$R_{4a}$, $R_{4b}$, or $R_{4c}$ is independently selected from hydrogen, —F, —Cl, —Br, —$C_{1-3}$alkyl or —$C_{1-3}$alkylene-N($C_{1-3}$alkyl)$_2$.

In some embodiments, $R_{4a}$, $R_{4b}$ or $R_{4c}$ is independently selected from hydrogen, —F, —Cl, methyl, ethyl, propyl, isopropyl, —$CH_2$—N($CH_3$)$_2$, —$CH_2$—N($CH_2CH_3$)$_2$ or —$CH_2$—N($CH_3$)($CH_2CH_3$).

In some embodiments, $R_{4a}$, $R_{4b}$ or $R_{4c}$ is independently selected from hydrogen, —F, methyl or —$CH_2$—N($CH_3$)$_2$.

In some embodiments, $R_{4a}$ is selected from hydrogen or —F;

$R_{4b}$ is hydrogen;

$R_{4c}$ is selected from hydrogen or —$CH_2$—N($CH_3$)$_2$.

In some embodiments, $R_{41}$ is independently selected from:

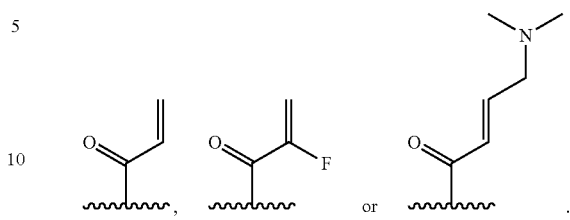

In some embodiments, $R_4$ is selected from

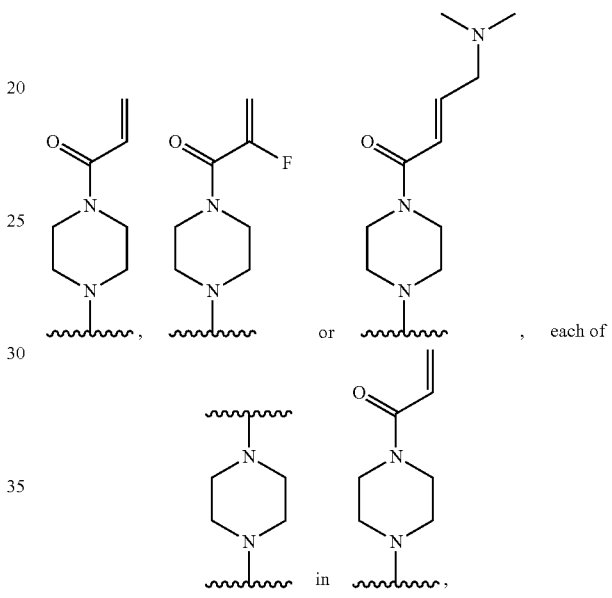

, each of at each occurrence is independently optionally substituted with 1 $R_{42}$ or 2 $R_{42}$.

In some embodiments, each $R_{42}$ at each occurrence is independently selected from —$C_{1-3}$alkyl; —$C_{1-3}$alkylene-CN; or —$C_{1-3}$alkyl substituted with —F or —Cl.

In some embodiments, each $R_{42}$ at each occurrence is independently selected from methyl; ethyl; propyl; isopropyl; -methylene-CN; -ethylene-CN; -propylene-CN; methyl substituted with —F; ethyl substituted with —F; propyl substituted with —F; or isopropyl substituted with —F.

In some embodiments, each $R_{42}$ at each occurrence is independently selected from methyl; ethyl; -methylene-CN or methyl substituted with —F.
In some embodiments, each $R_{42}$ at each occurrence is independently selected from —$CH_3$, —$CH_2CH_3$, —$CH_2CN$, —$CHF_2$ or —$CF_3$.
In some embodiments, $R_4$ is selected from:
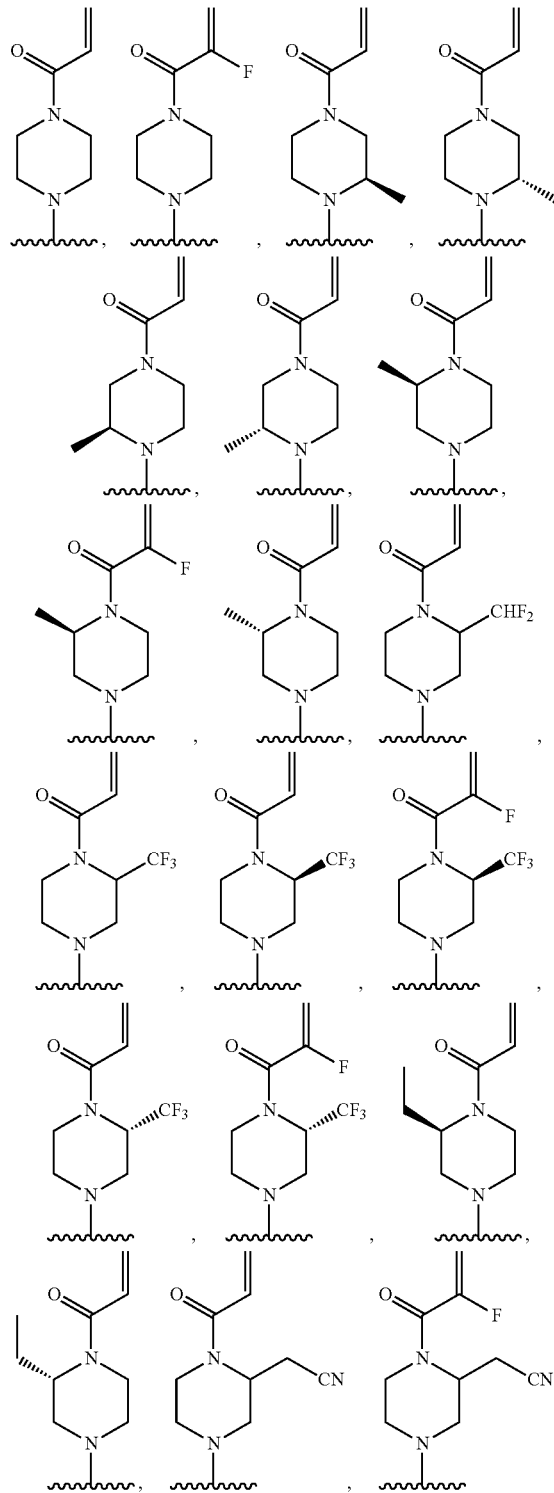
-continued
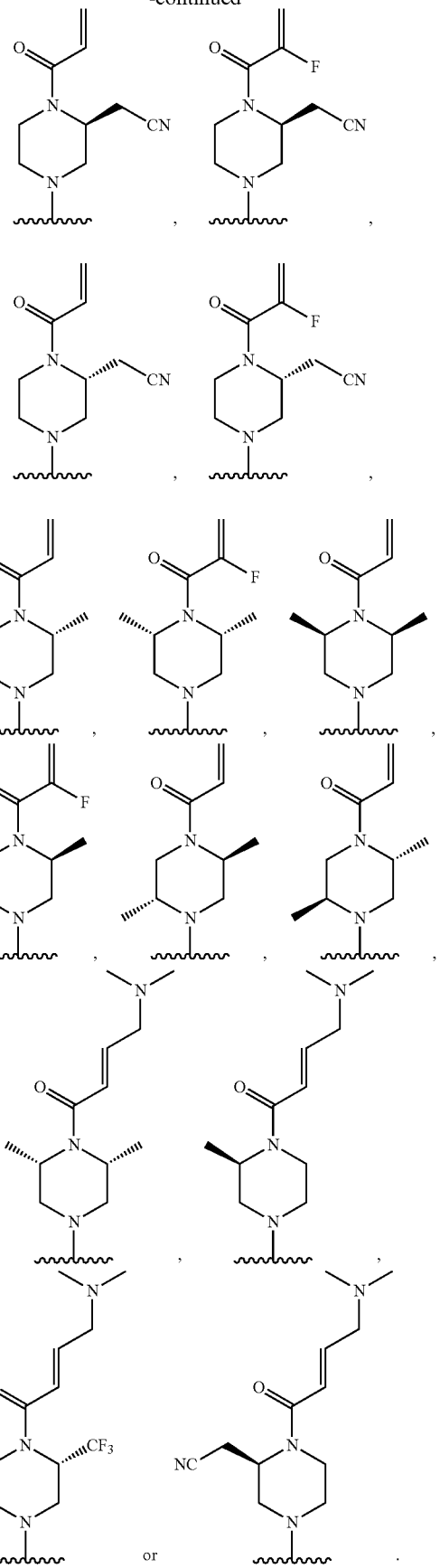
or In some embodiments, R$_4$ is selected from:
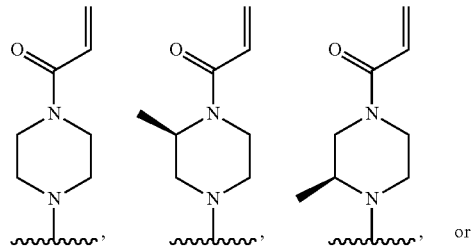
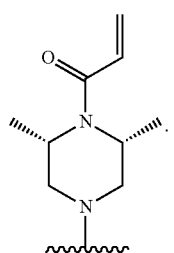
In some embodiments, R$_4$ is selected from:
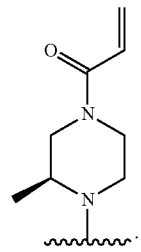
In some embodiments, the compound is selected from:
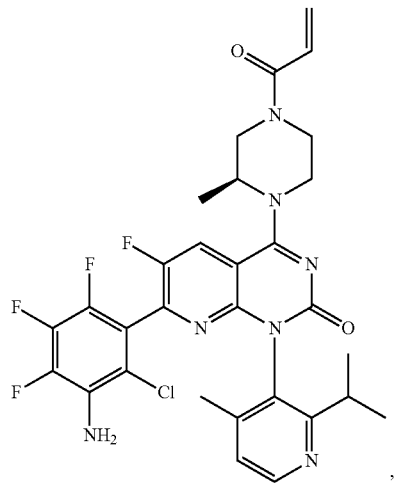
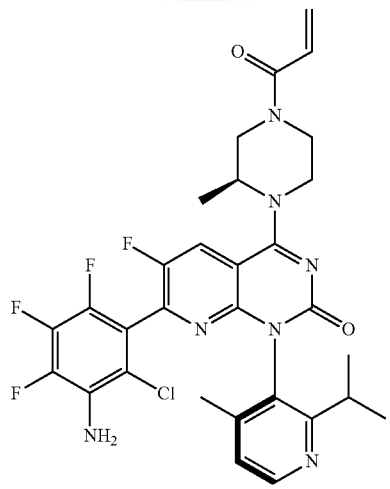
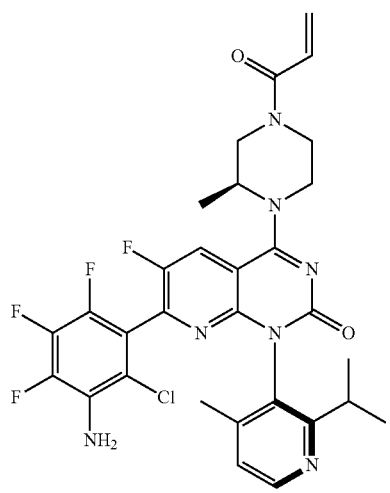
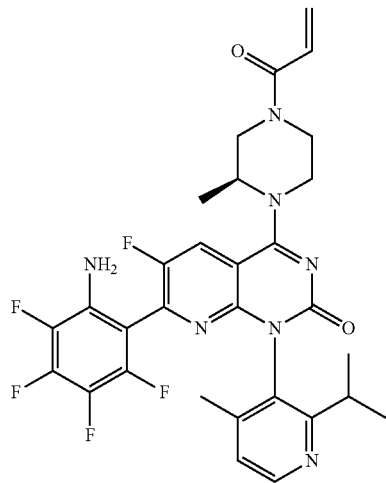

21
-continued
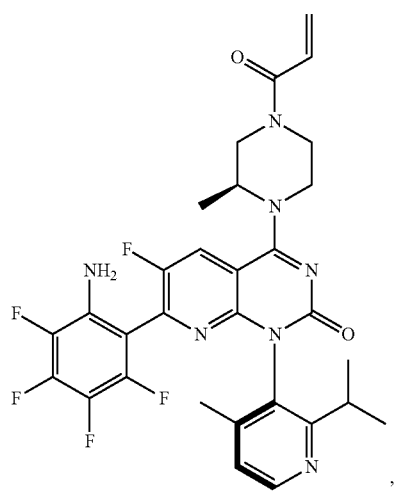
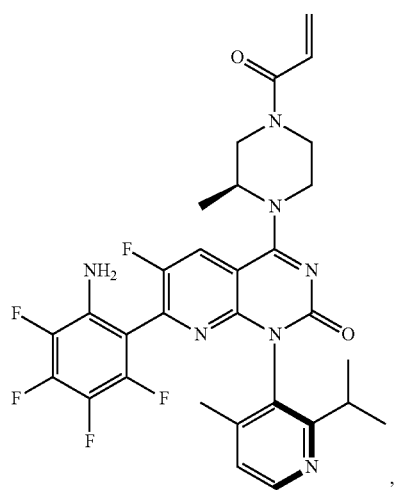
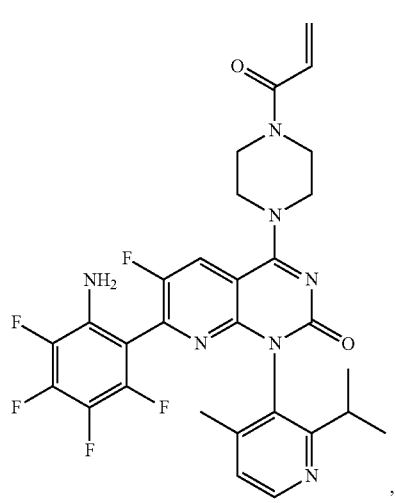
22
-continued
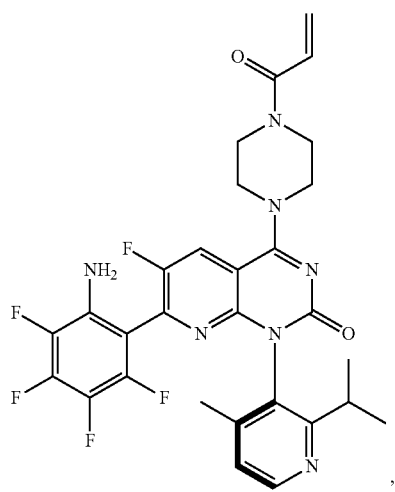
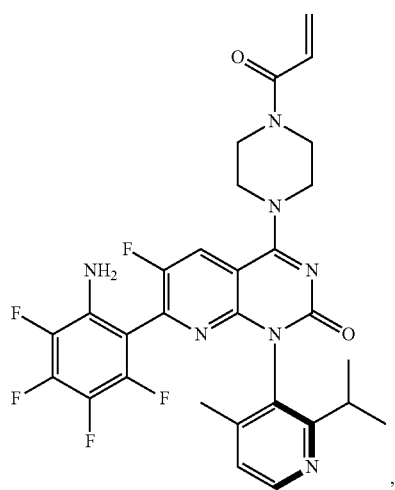
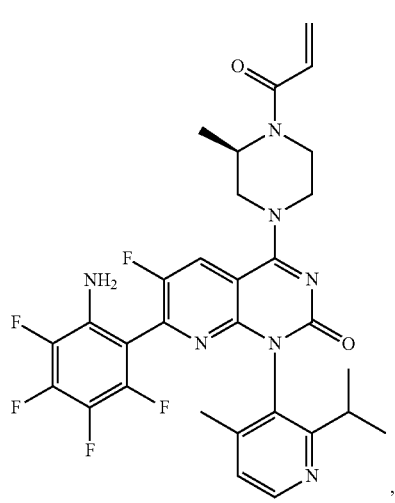

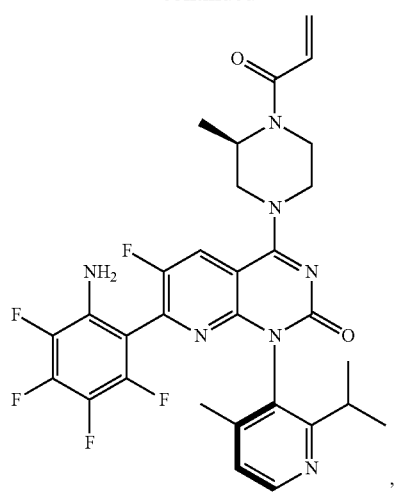
,
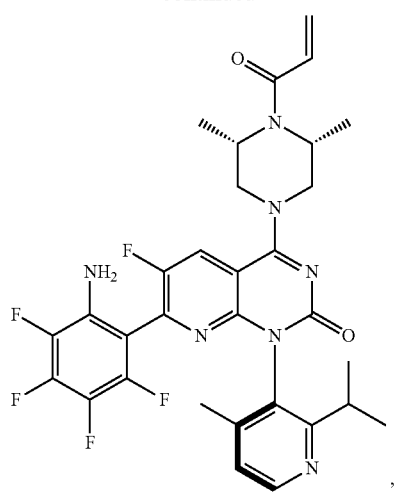
,
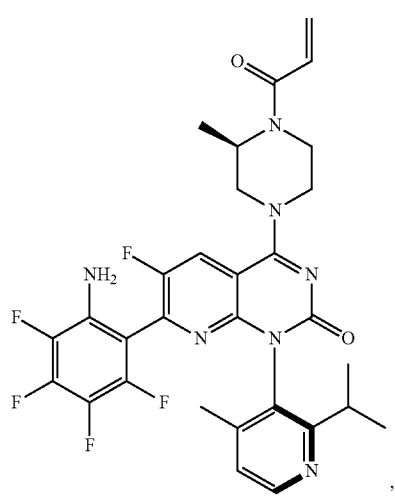
,
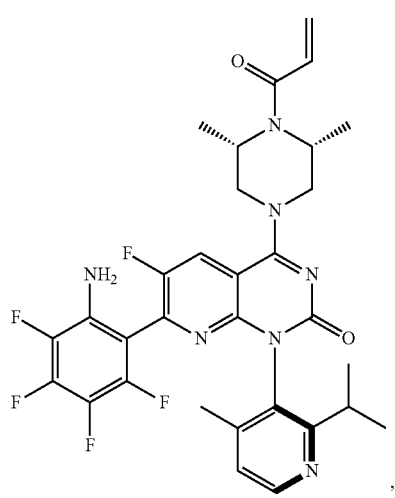
,
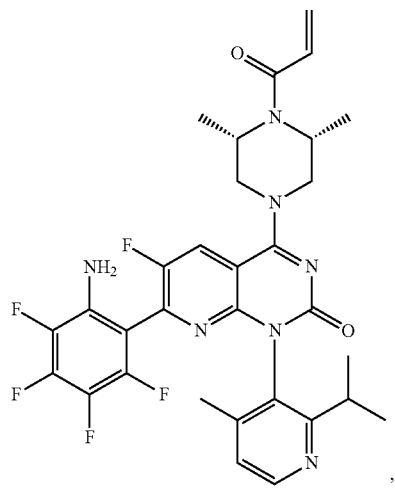
,

25
-continued
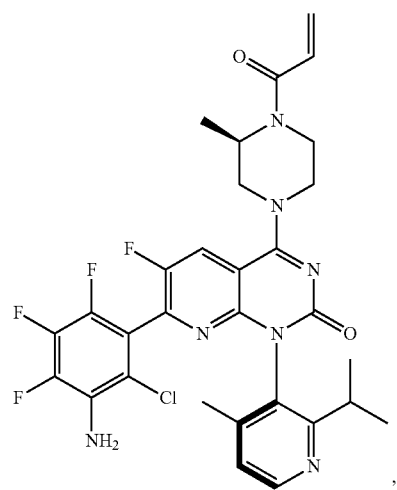
,
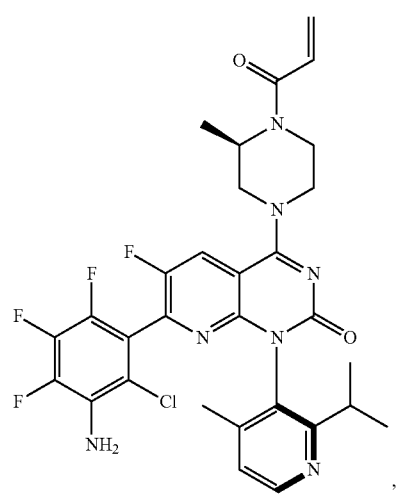
,
26
-continued
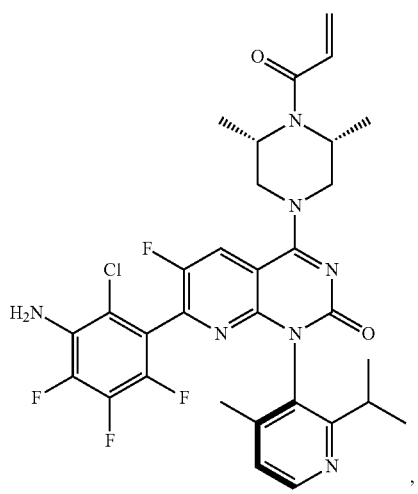
,
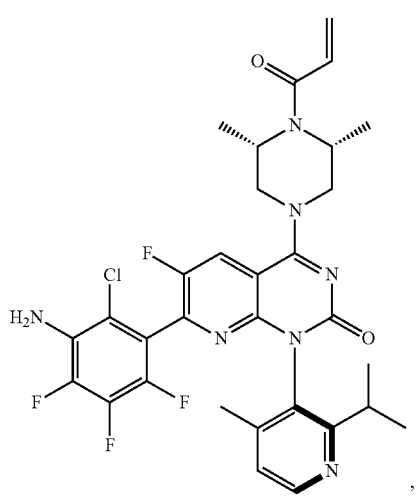
,

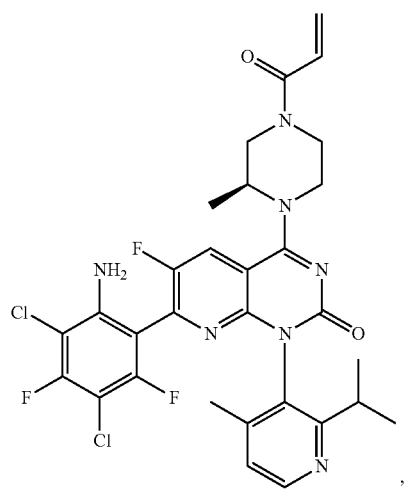
,
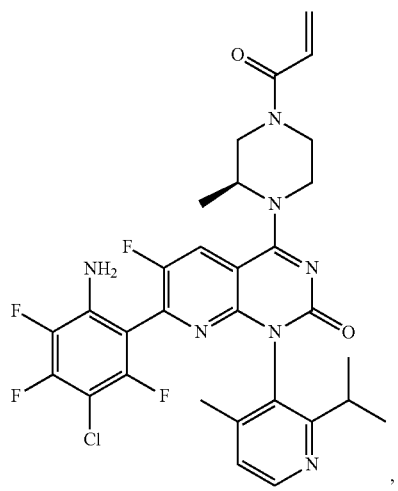
,
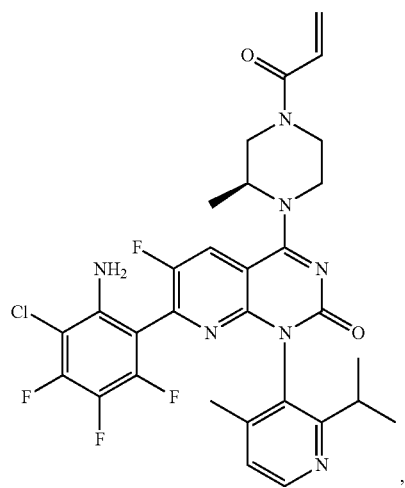
,
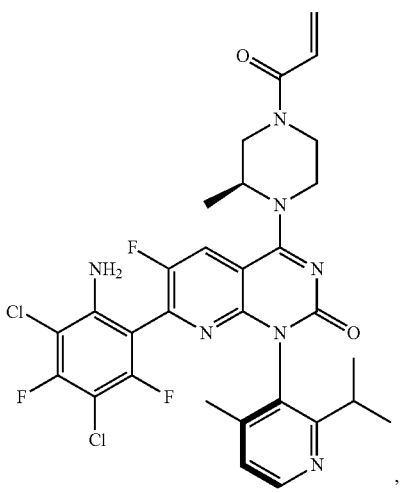
,
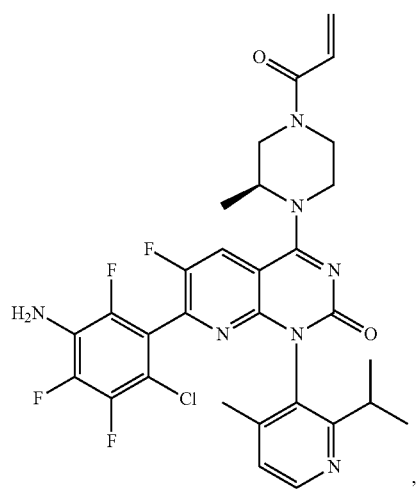
,

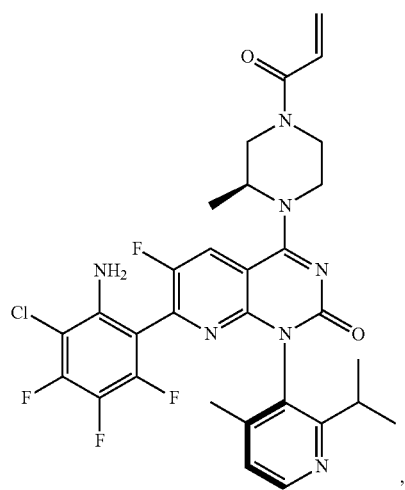
,
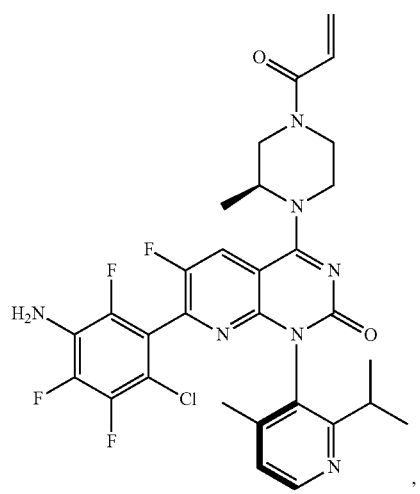
,
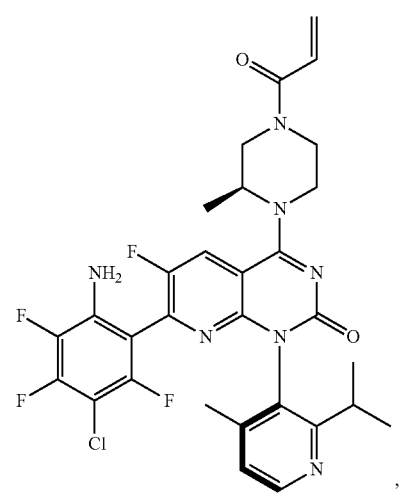
,
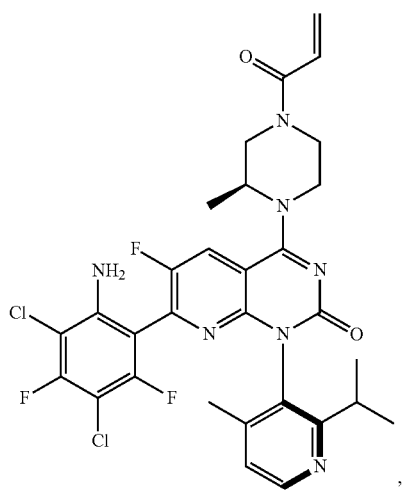
,
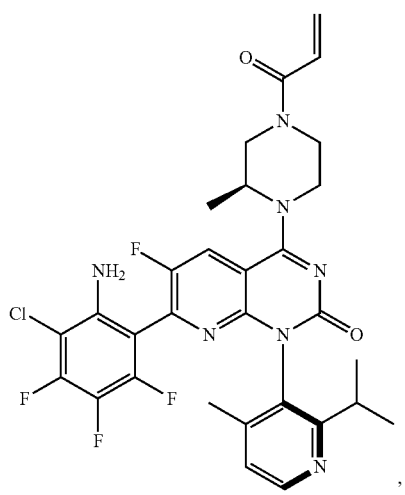
,

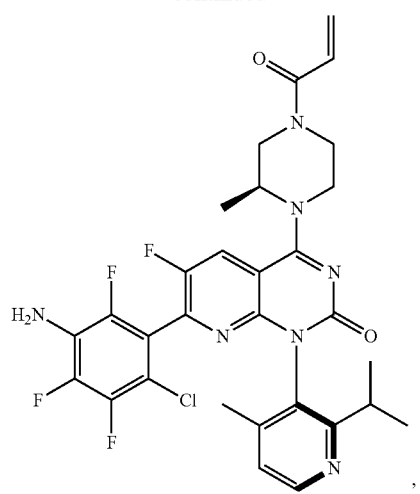
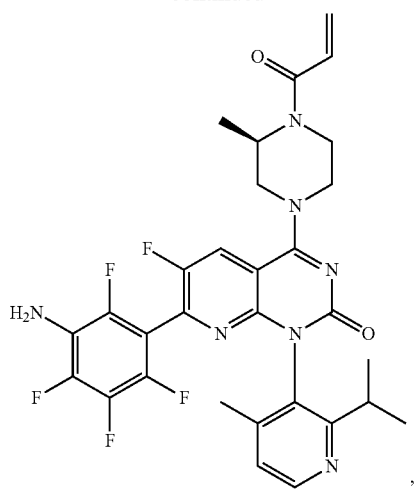
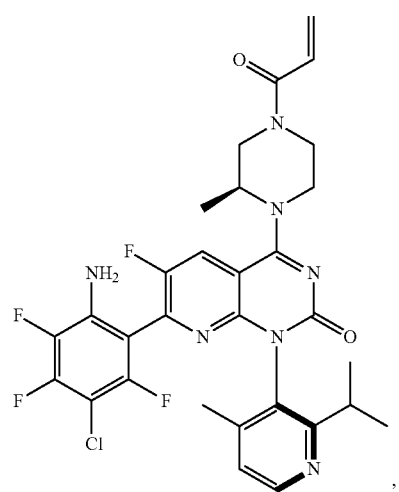
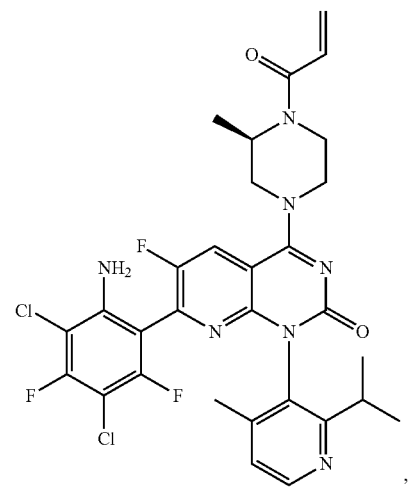
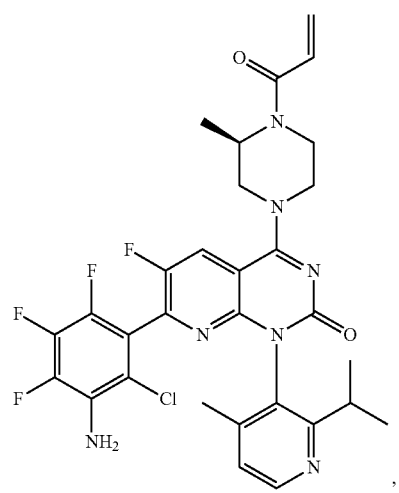

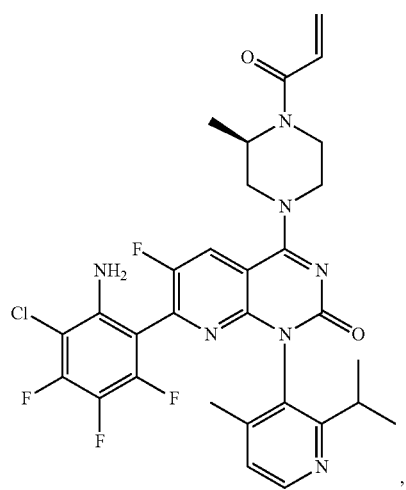
,
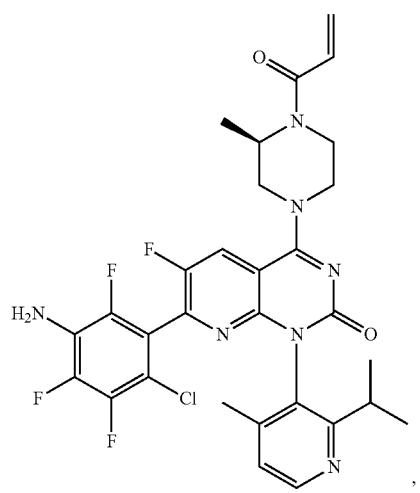
,
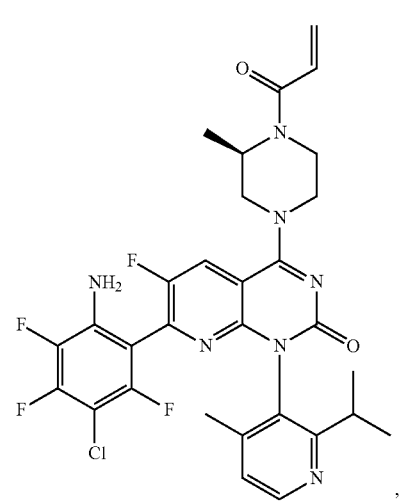
,
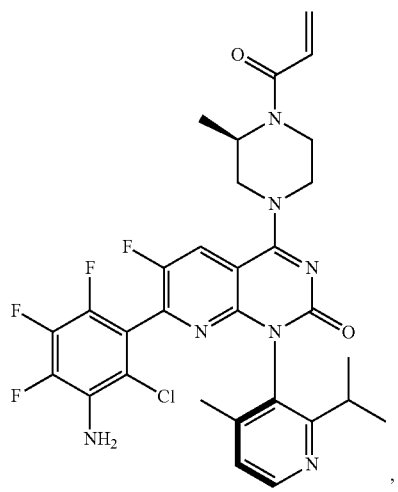
,
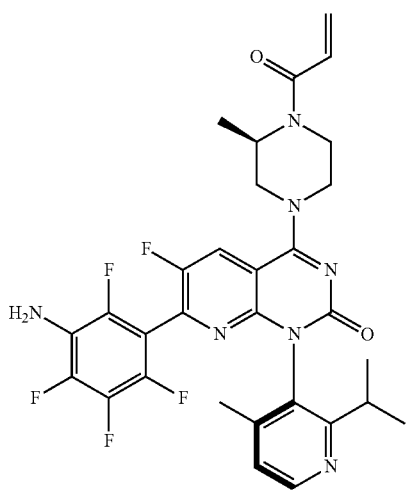
,
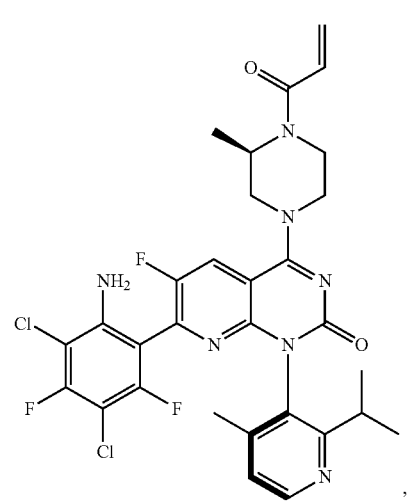
,

-continued
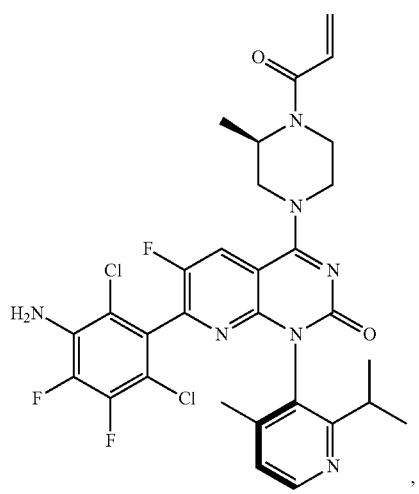
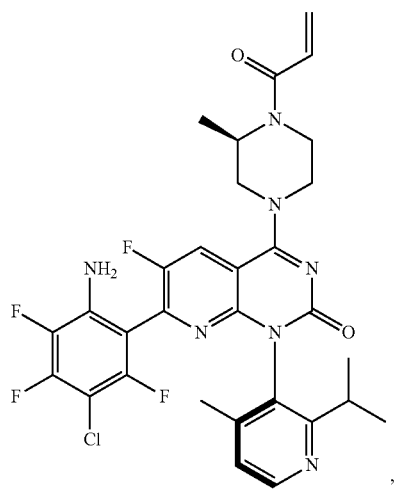
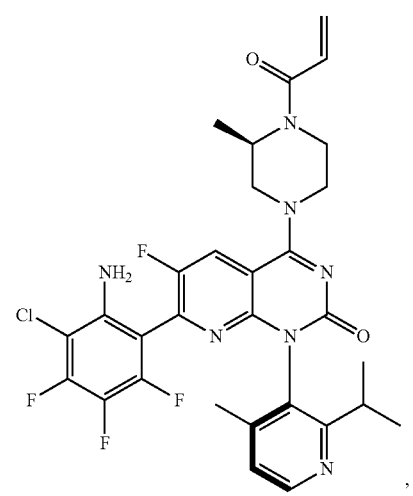
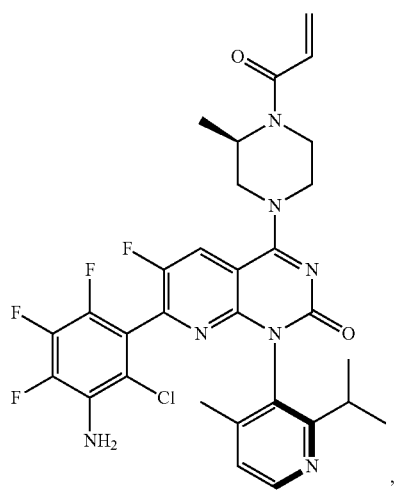
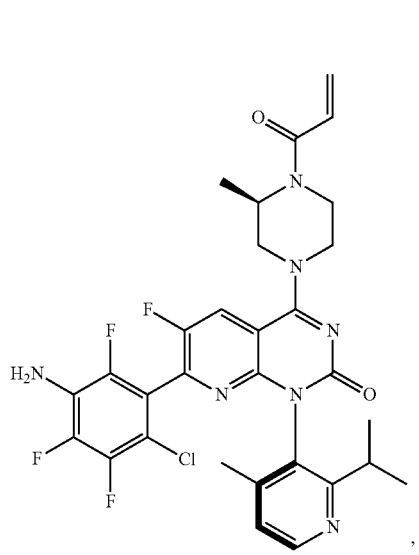
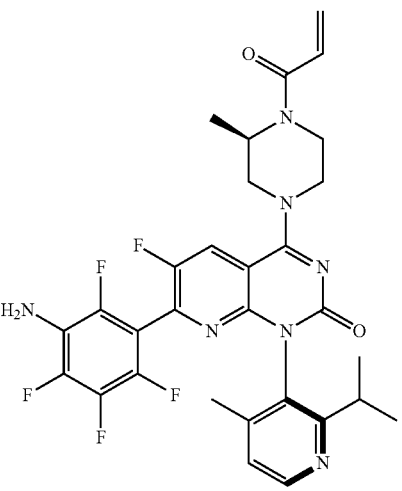

37
-continued
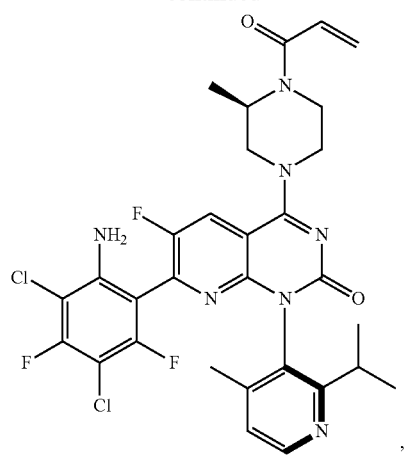
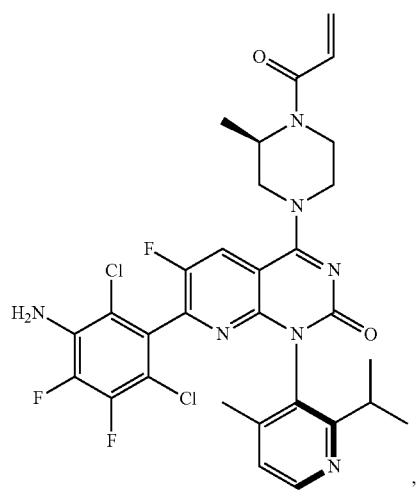
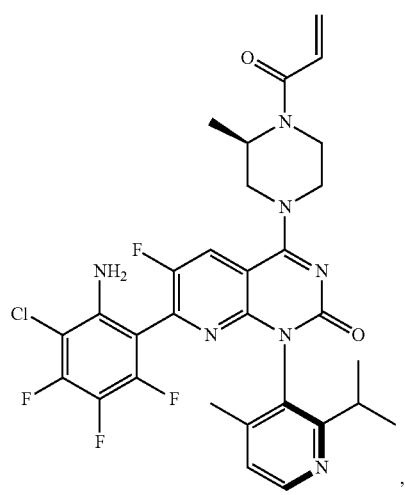
38
-continued
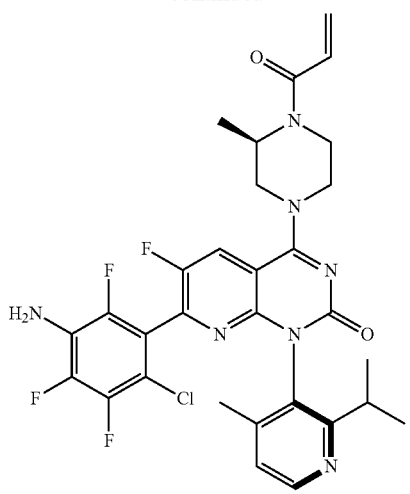
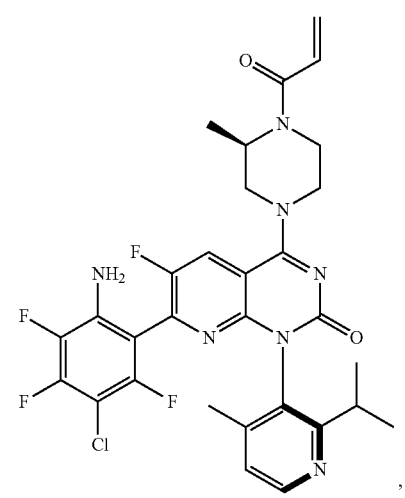
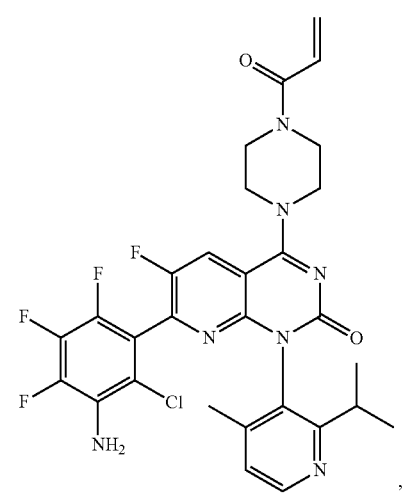

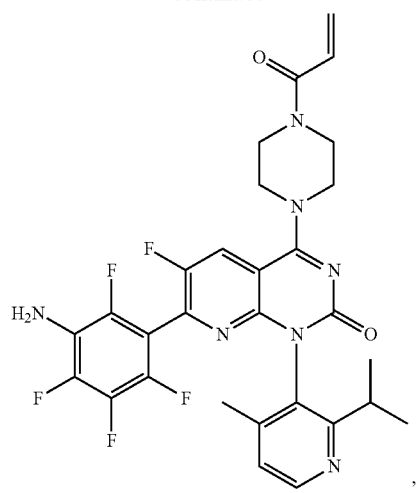
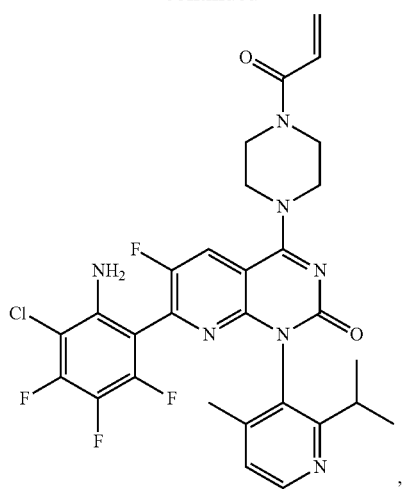
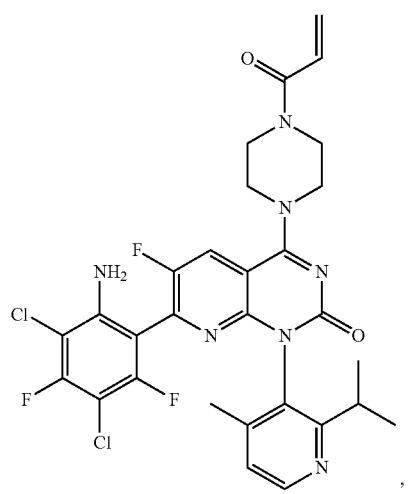
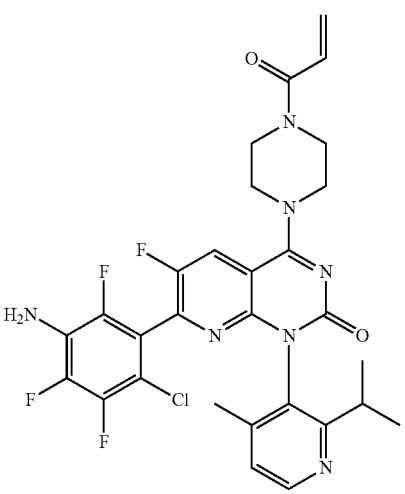
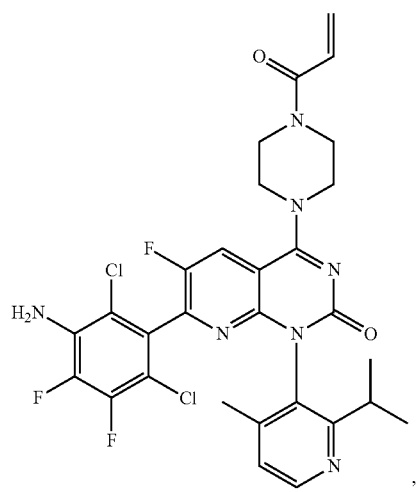

-continued
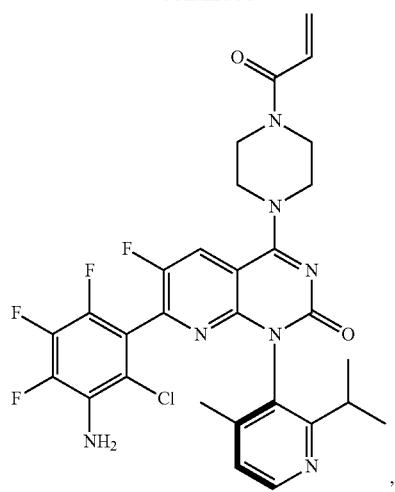
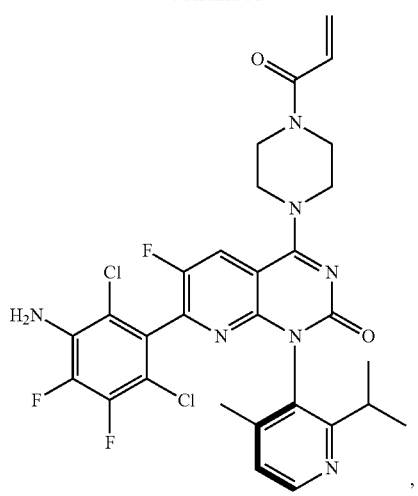
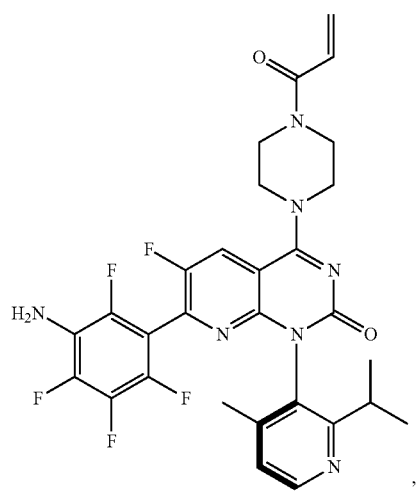
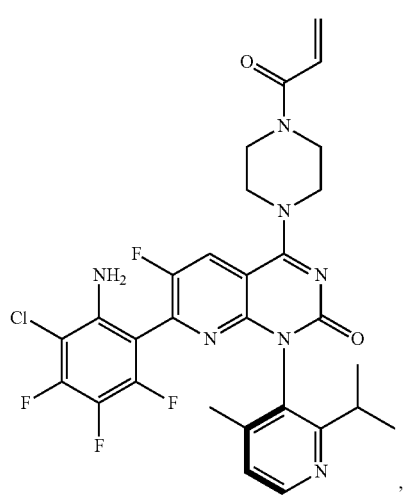
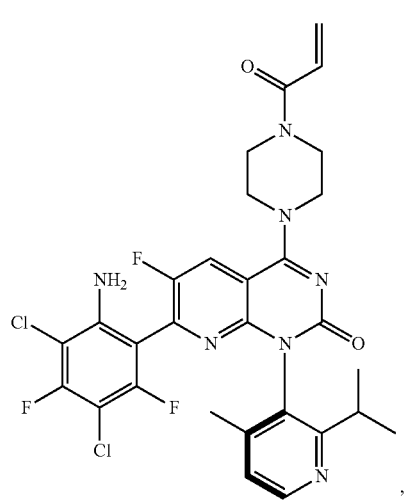
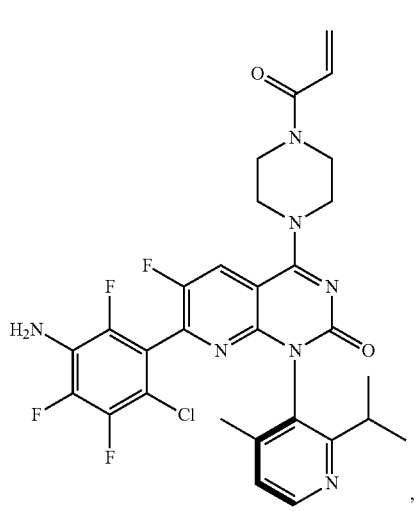

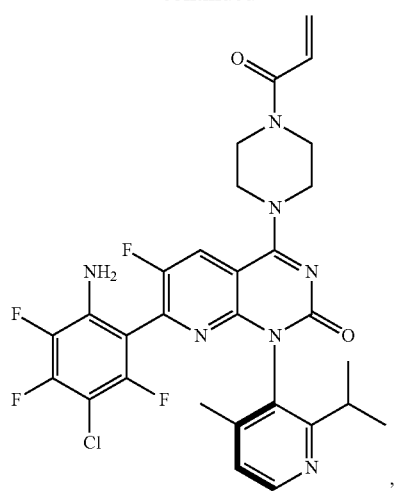
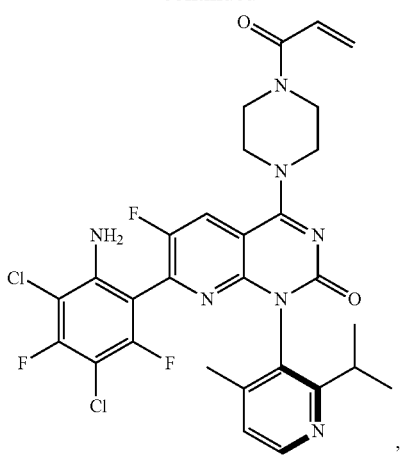
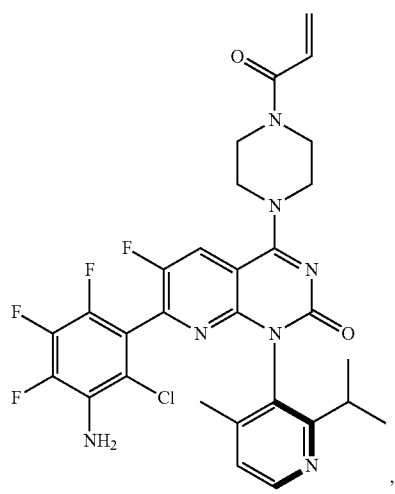
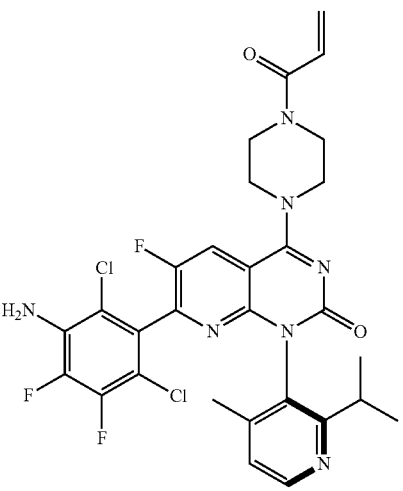
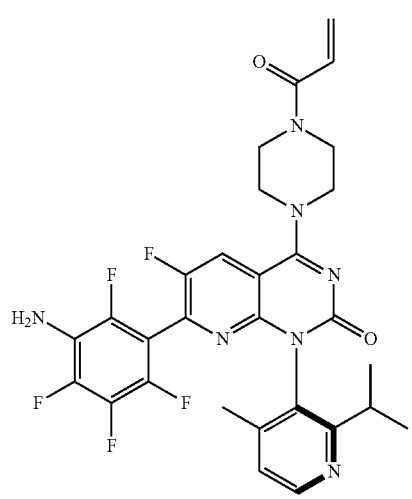
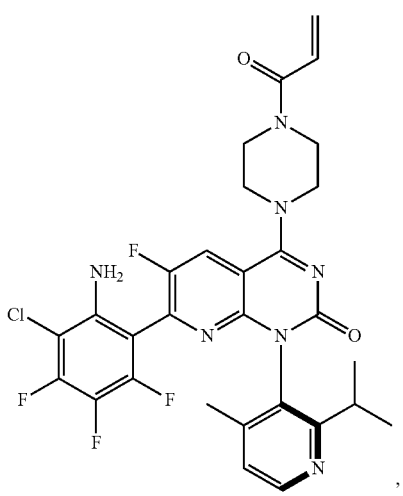

45
-continued
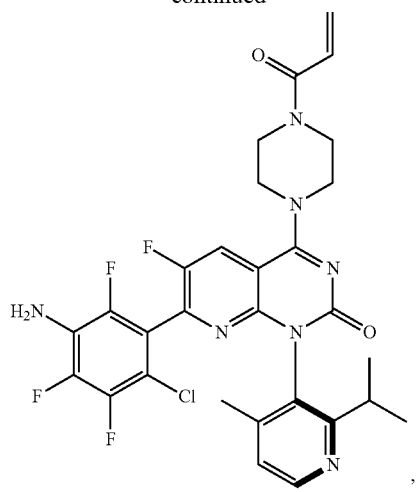
46
-continued
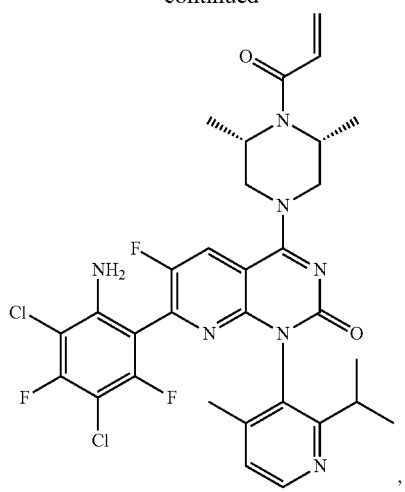

47
-continued
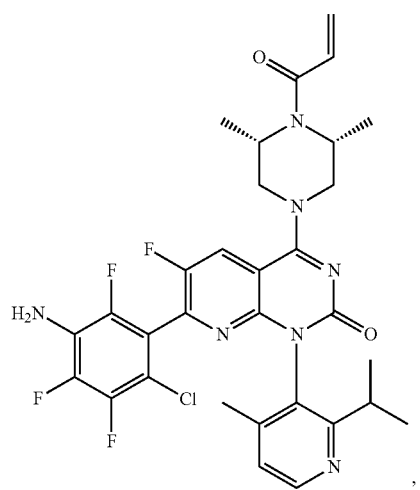
,
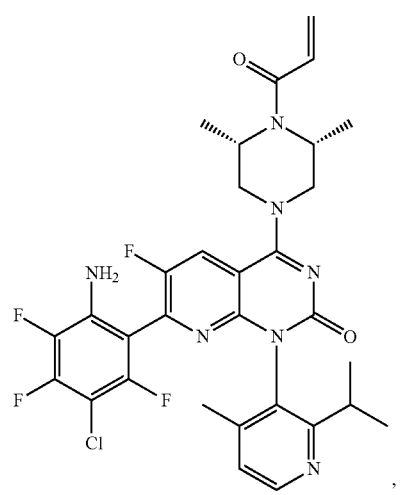
,
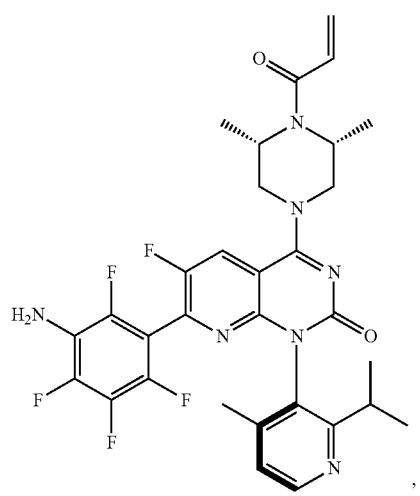
,
48
-continued
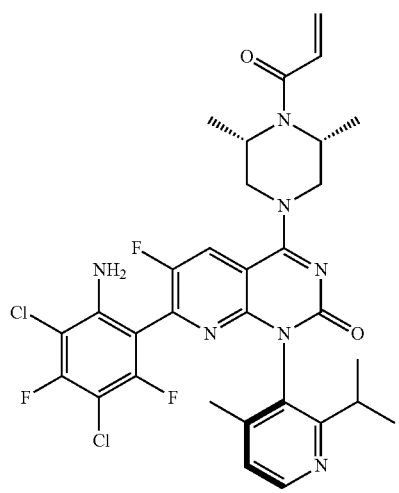
,
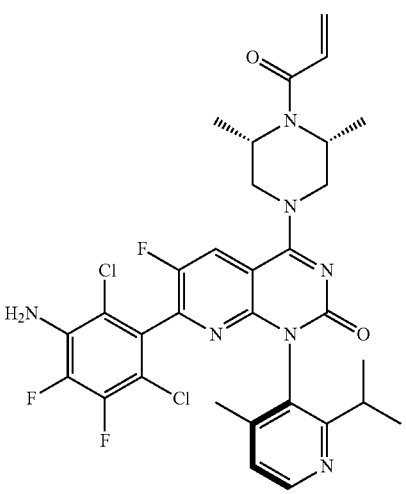
,
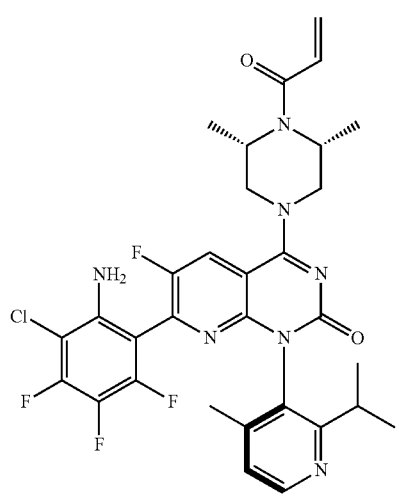
, 49
-continued
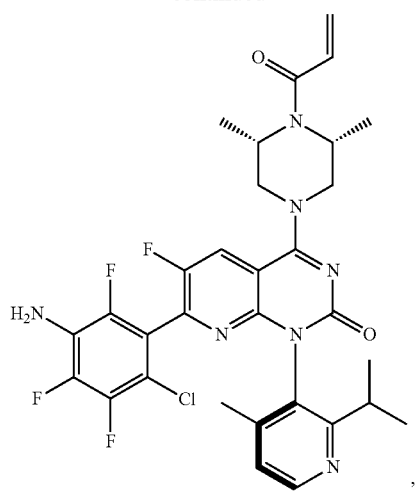
,
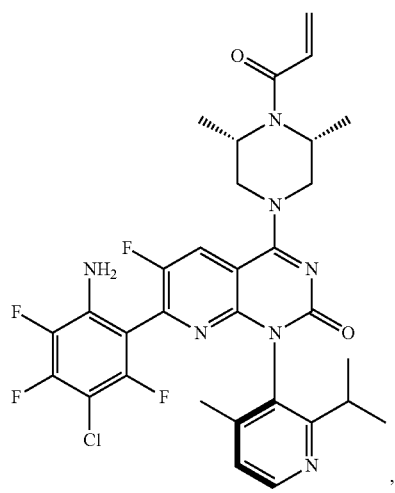
,
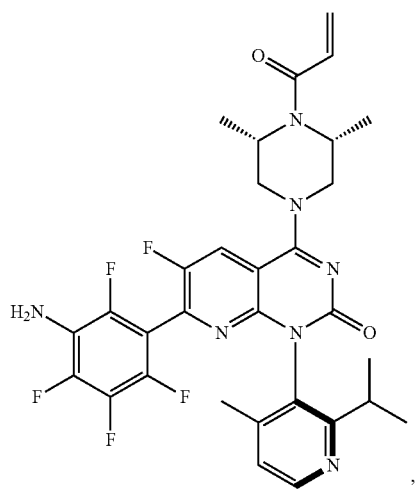
,
50
-continued
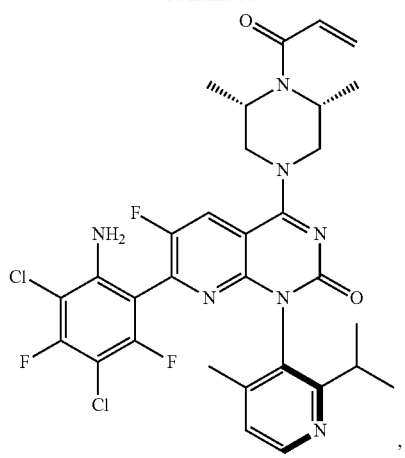
,
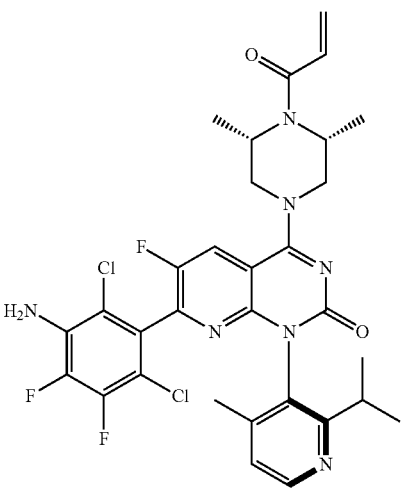
,
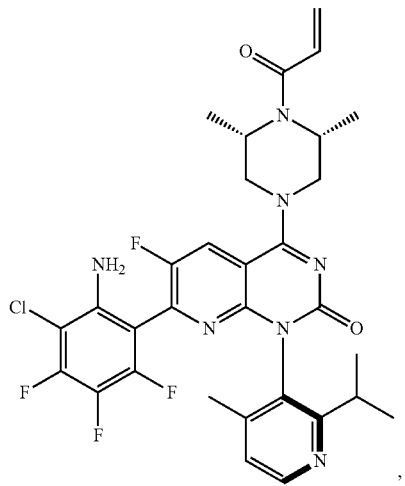
, 51 52
-continued

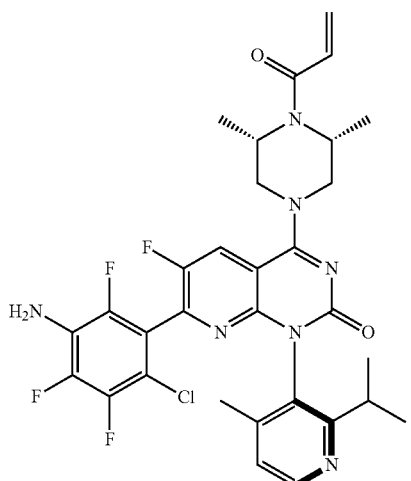

or

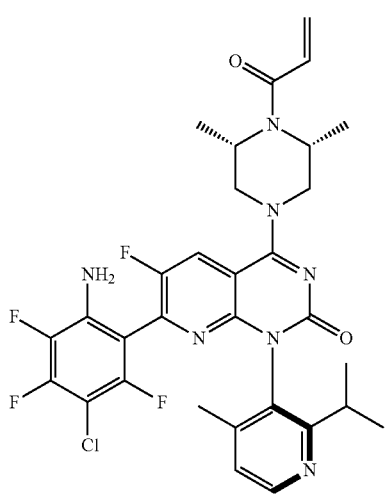

.

In another aspect, provided herein is a method for preparing the compound of formula (I), the stereoisomer thereof, the atropisomer thereof, the pharmaceutically acceptable salt thereof, the pharmaceutically acceptable salt of the stereoisomer thereof or the pharmaceutically acceptable salt of the atropisomer thereof, the method comprises a coupling reaction between a compound of formula (II) and a compound of formula (III) according to the following reaction Scheme 1 or between a compound of formula (II') and a compound of formula (III') according to the following reaction Scheme 2 catalyzed by a transition metal palladium or nickel reagent:

Scheme 1:

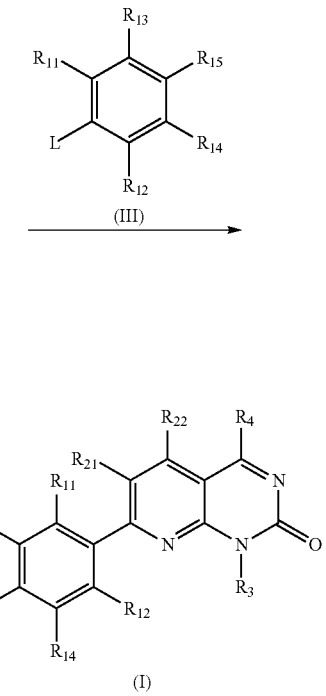

Scheme 2:

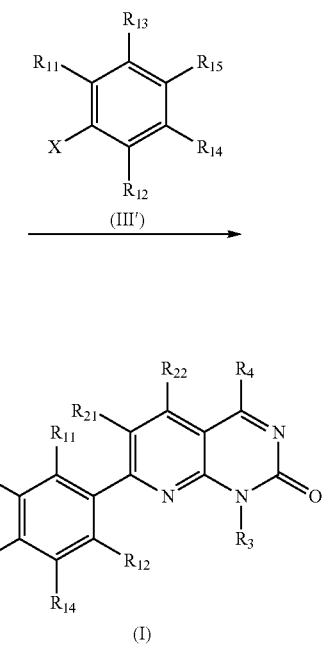

Wherein:

the L in the compound of formula(III) or formula(II') is a leaving group; preferably, the leaving group is selected from halogen, —OS(O)$_2$CF$_3$ or -OTs; more preferably, the halogen is selected from —F, —Cl, —Br, or —I; more preferably, the leaving group is —Cl or —Br;

the X in the compound of formula (II) or formula(III') is selected from boronic acid, borate ester or organotin; more preferably, the X is selected from

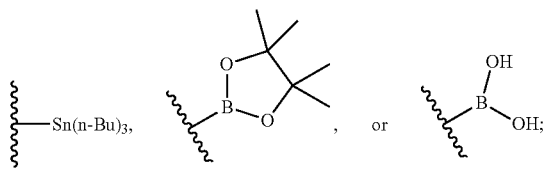

Preferably, the coupling reaction is Suzuki coupling reaction or Stille coupling reaction;

Preferably, the coupling reaction is catalyzed by the transition metal palladium reagent; more preferably, the transition metal palladium reagent is $Pd(PPh_3)_4$.

In another aspect, provided herein is an intermediate of formula (IV), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof:

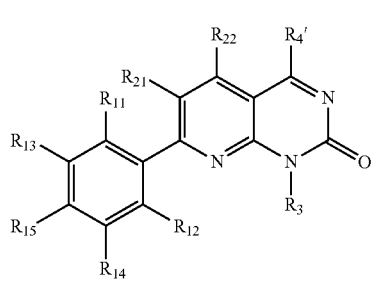

(IV)

Wherein:
$R_{11}$, $R_{12}$, $R_{13}$, $R_{14}$, $R_{15}$, $R_{21}$, $R_{22}$ or $R_3$ is defined as in the present invention; and $R_4'$ is selected from

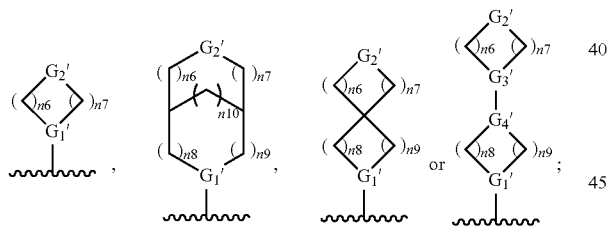

Each $G_1'$, $G_2'$, $G_3'$ or $G_4'$ at each occurrence is independently selected from NH or CH;

Each n6, n7, n8, n9 or n10 at each occurrence is independently selected from 0, 1, 2, 3, 4, 5 or 6, provided that n6 and n7 is not 0 at the same time, n8 and n9 is not 0 at the same time;

Said

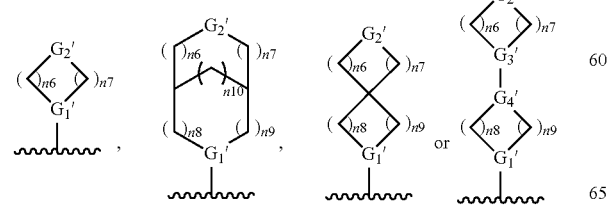

is independently optionally substituted with 1 $R_{42}$, 2 $R_{42}$, 3 $R_{42}$, 4 $R_{42}$, 5 $R_{42}$ or 6 $R_{42}$;

Each $R_{42}$ is defined as in the present invention.

In some embodiments, the intermediate of formula (IV) is the formula (IV'):

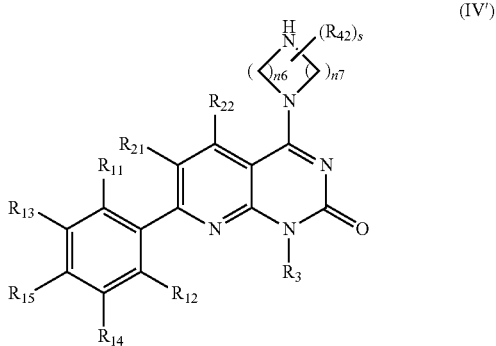

(IV')

n6 or n7 is selected from 1, or 2; and s is selected from 0, 1, 2, or 3;

$R_{11}$, $R_{12}$, $R_{13}$, $R_{14}$, $R_{15}$, $R_{21}$, $R_{22}$, $R_3$ or $R_{42}$ is defined as in the present invention.

In some embodiments, the intermediate of formula (IV) is selected from:

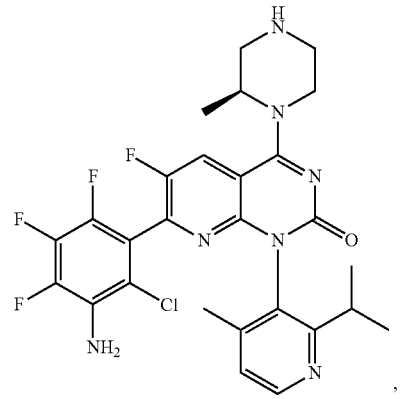

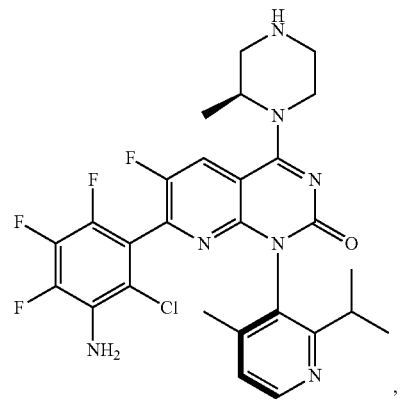

55
-continued
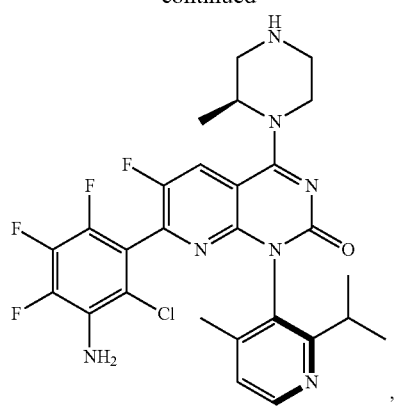
,
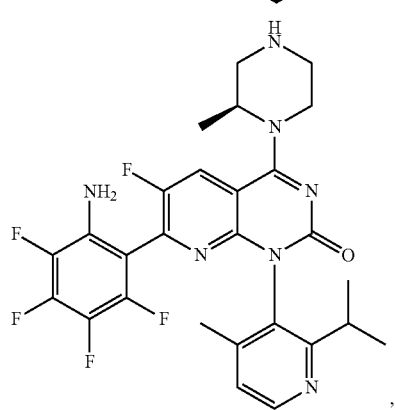
,
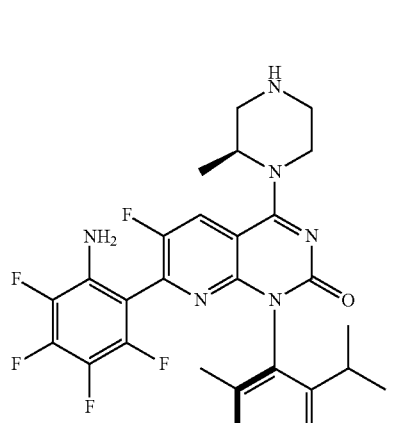
,
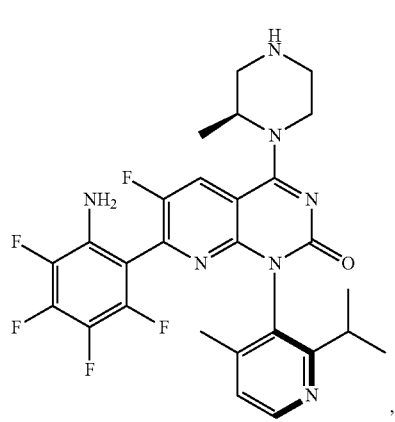
,
56
-continued
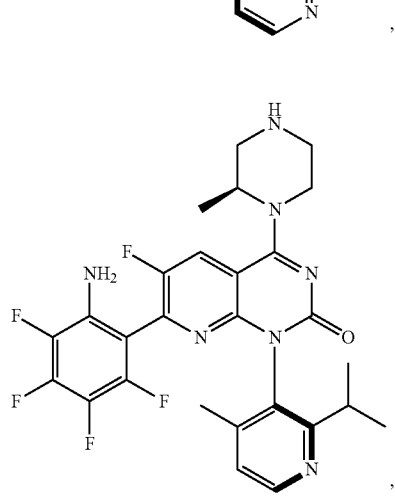
,
,
,
, 57
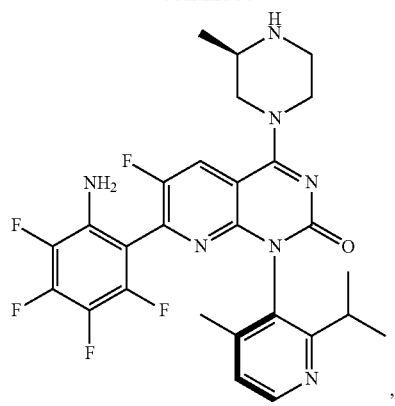
,
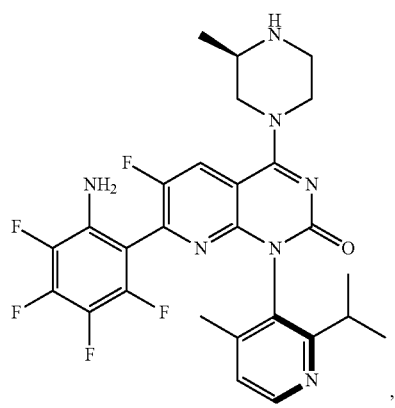
,
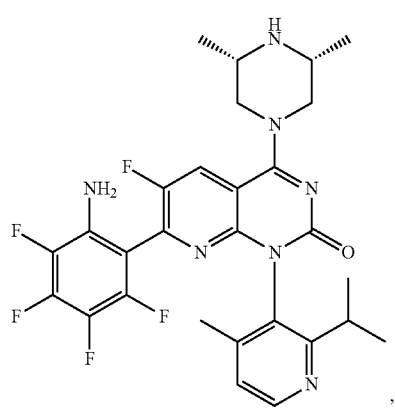
,
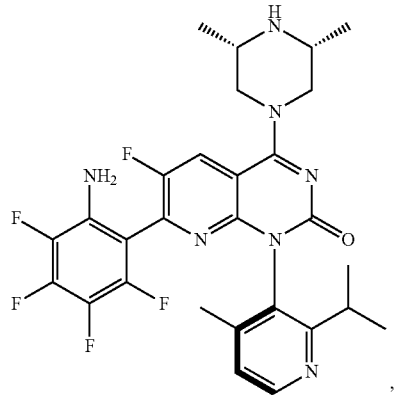
,
58
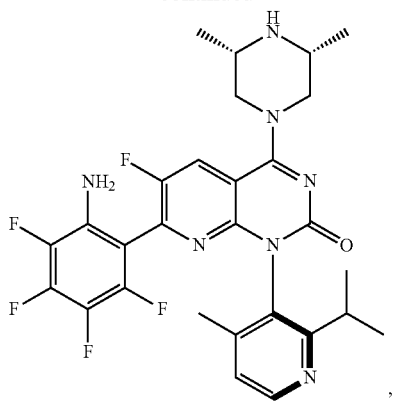
,
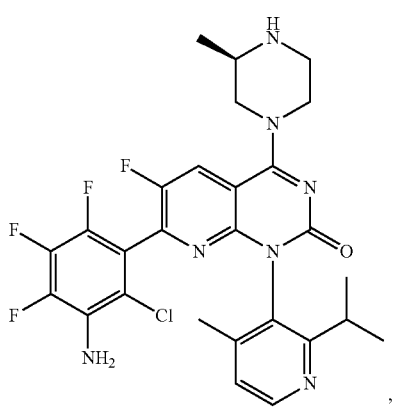
,
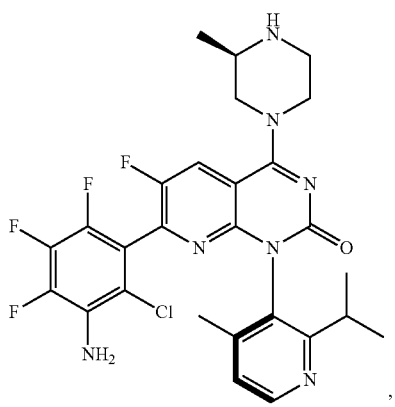
,
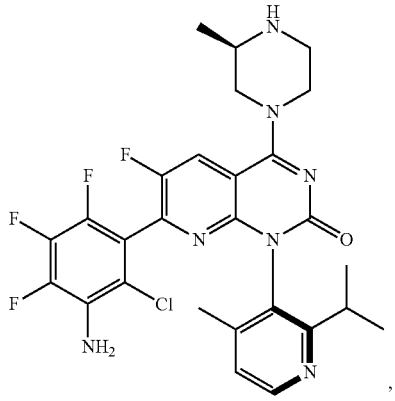
, -continued
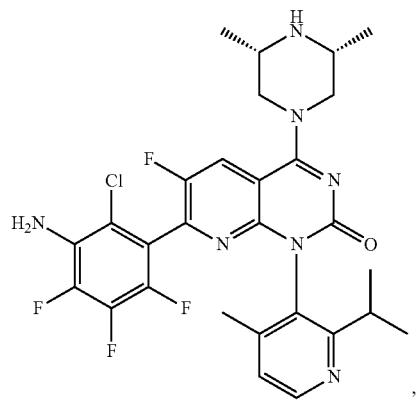
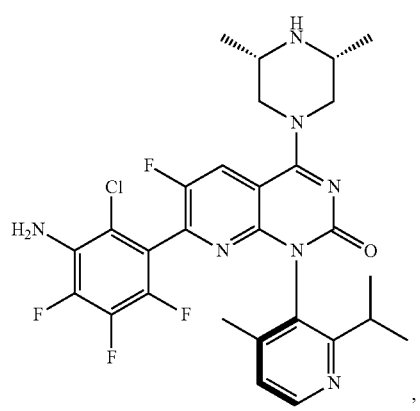
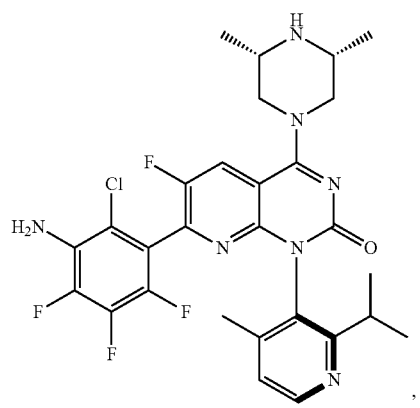
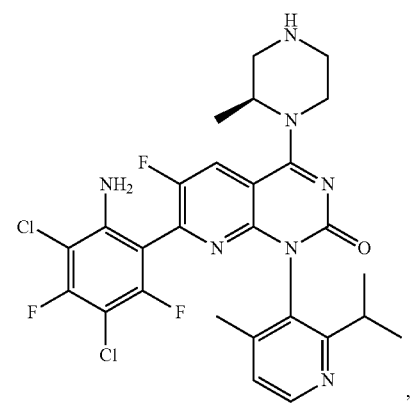
-continued
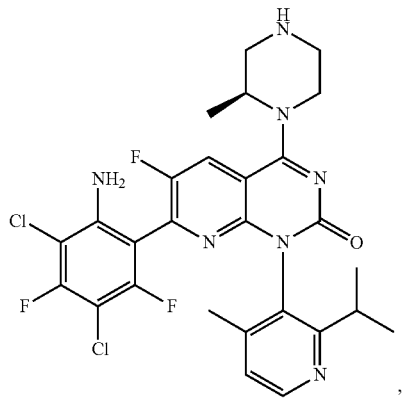
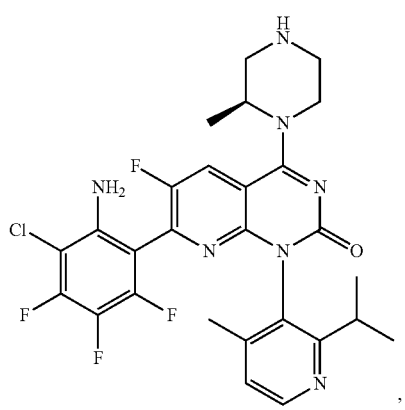
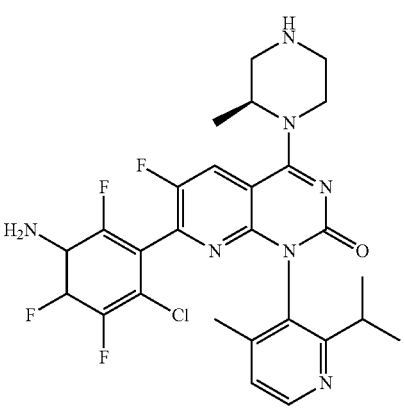
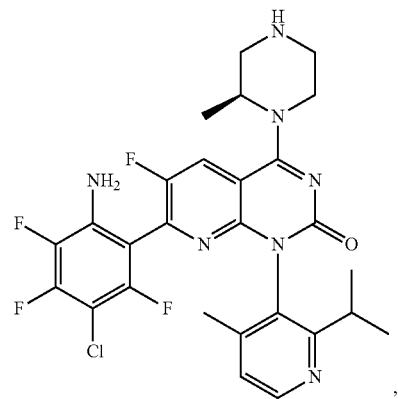

61
-continued
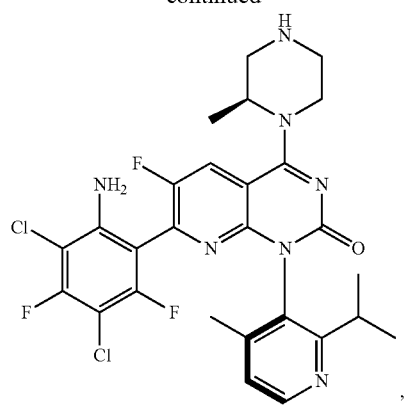
,
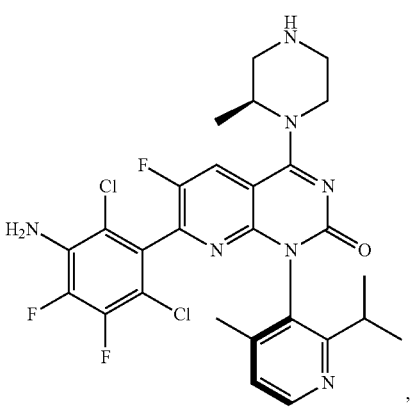
,
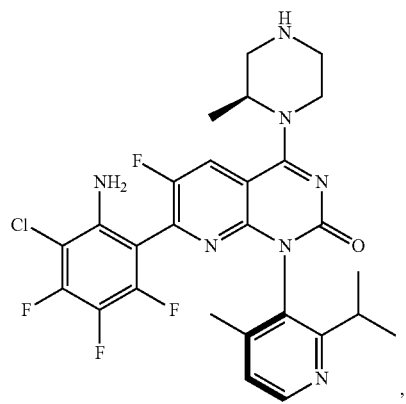
,
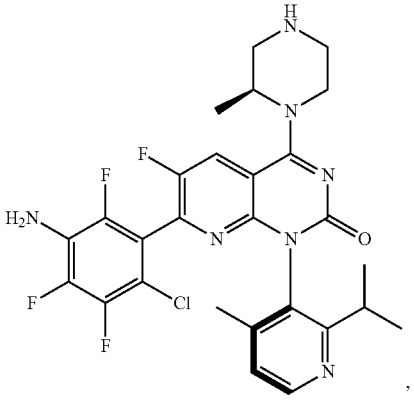
,
62
-continued
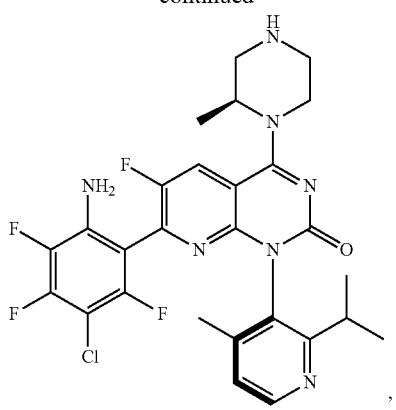
,
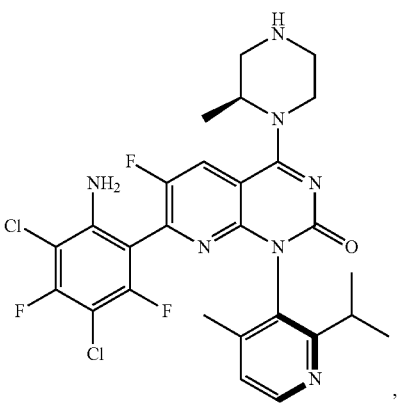
,
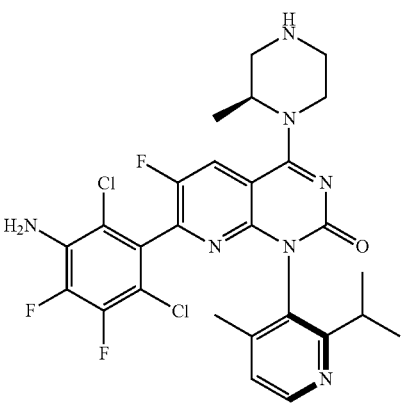
,
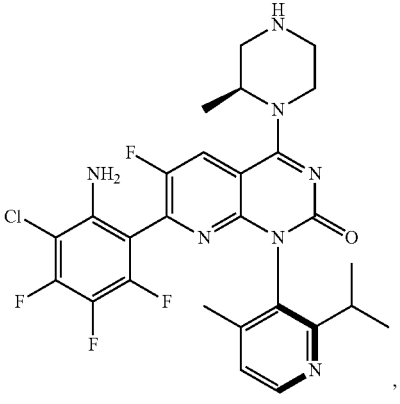
,

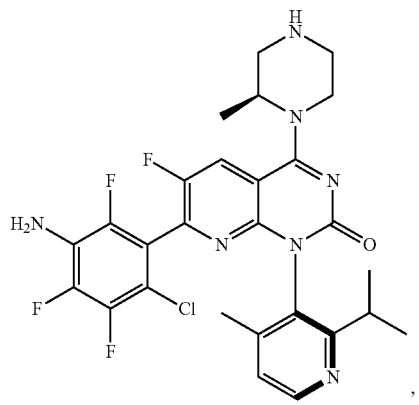
,
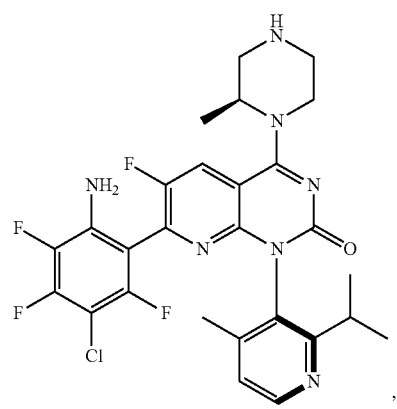
,
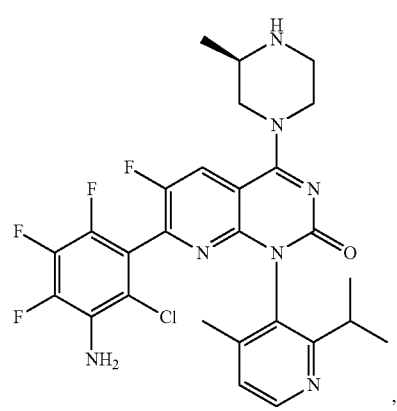
,
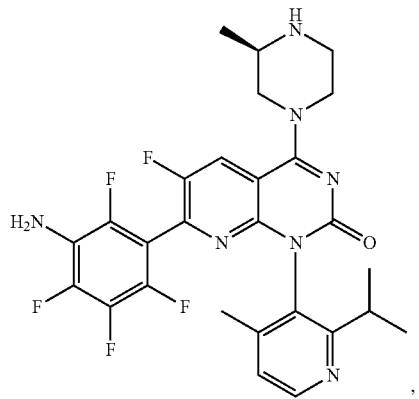
,
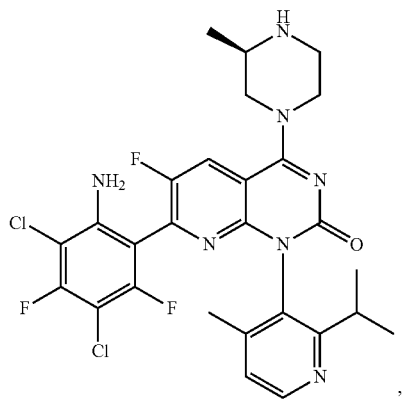
,
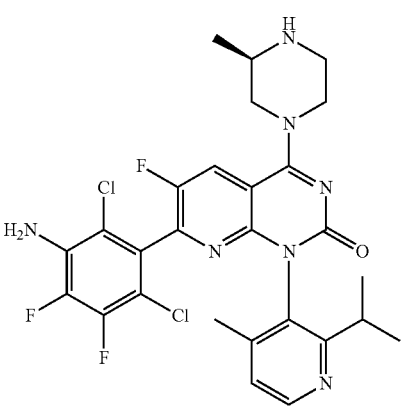
,
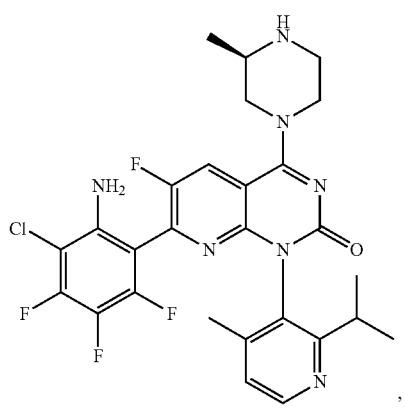
,
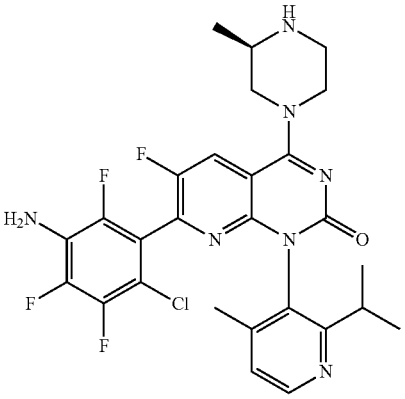
,

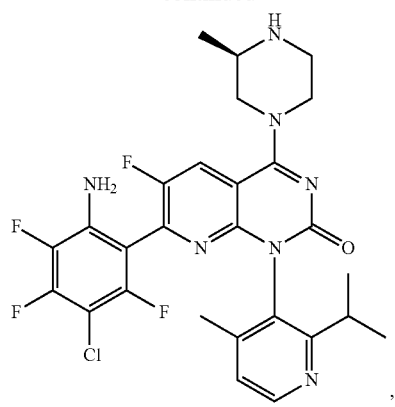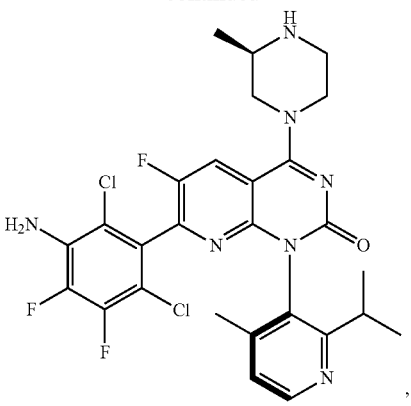

67
-continued
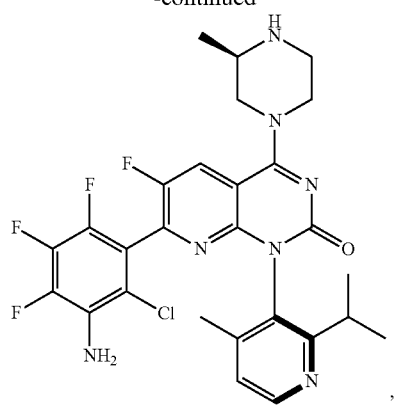
,
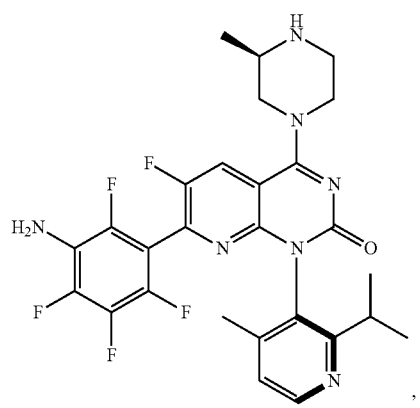
,
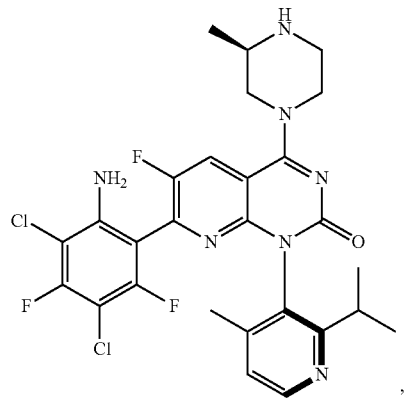
,
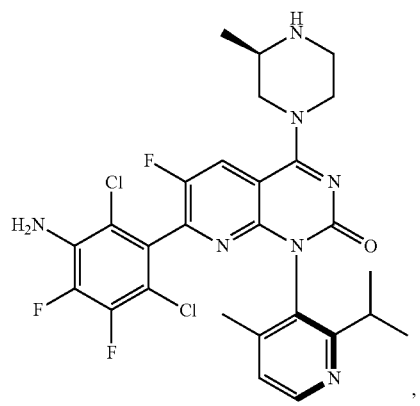
,
68
-continued
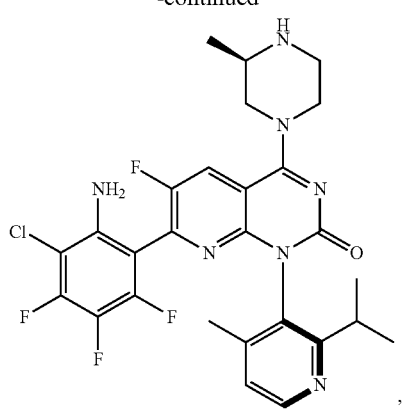
,
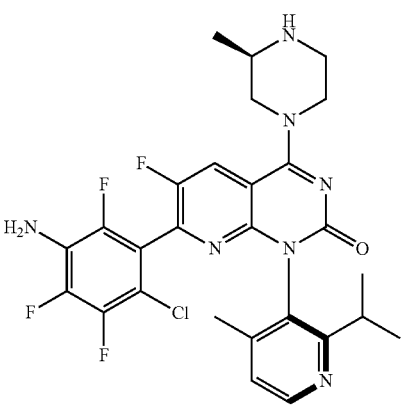
,
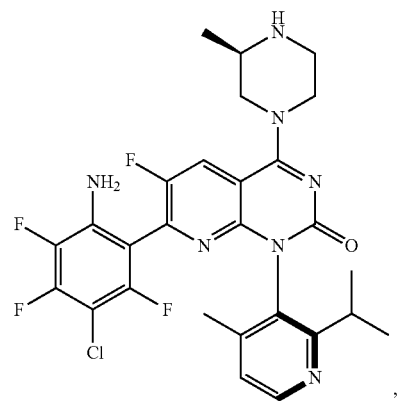
,
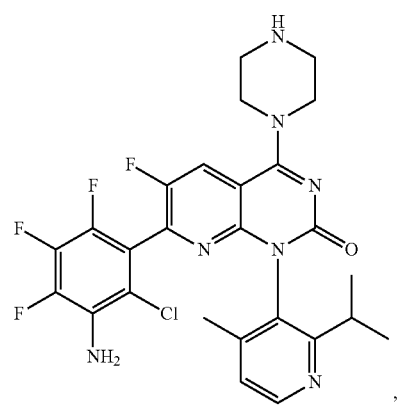
, 69
-continued
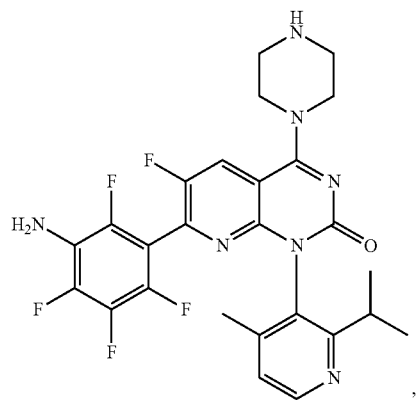
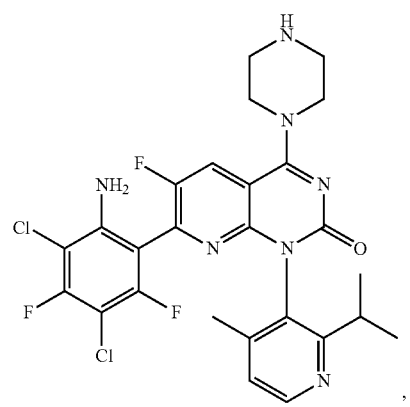
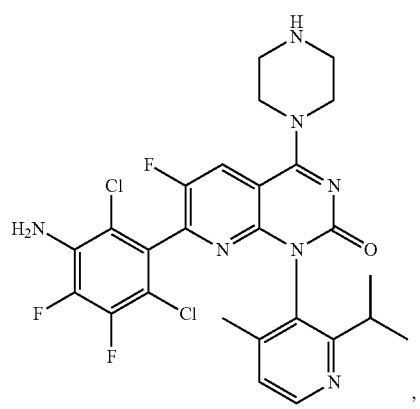
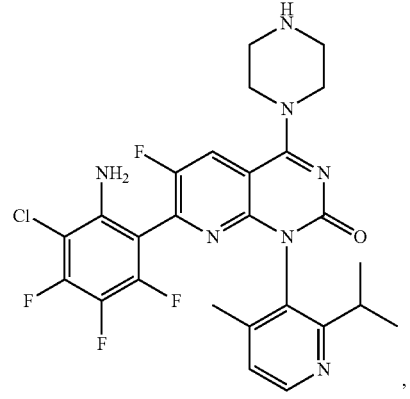
70
-continued
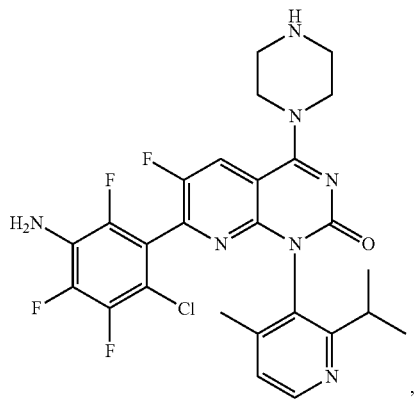
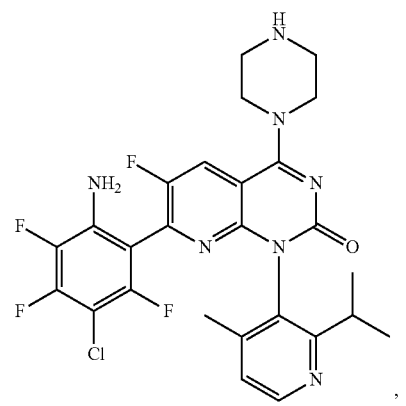
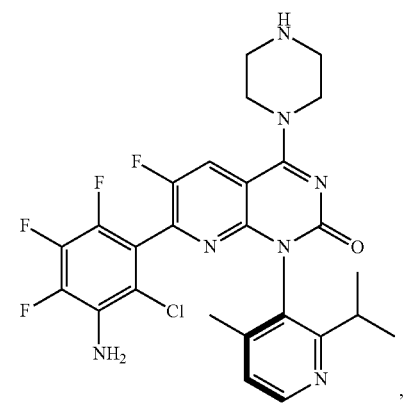
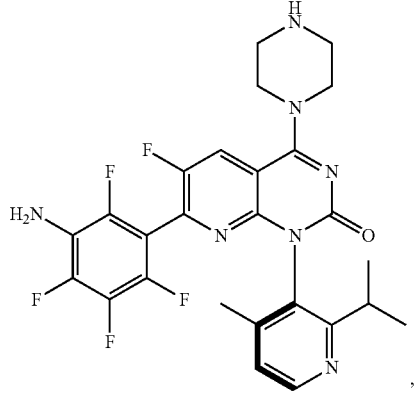

71
-continued
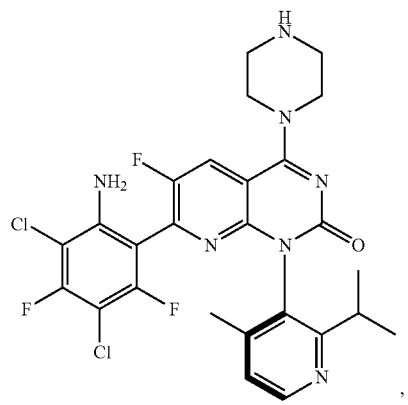
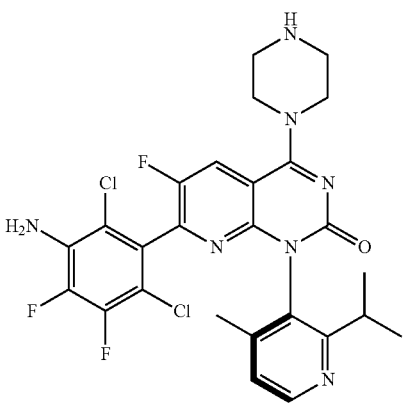
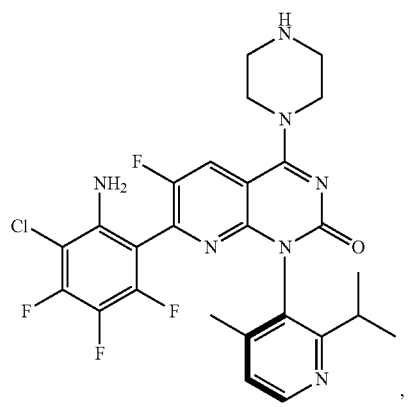
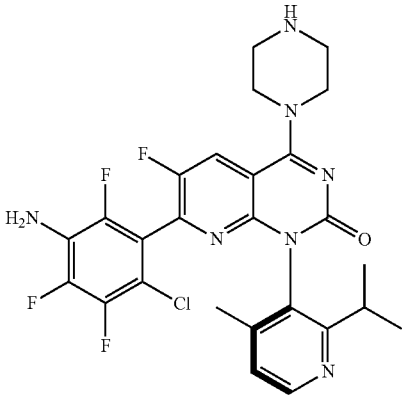
72
-continued
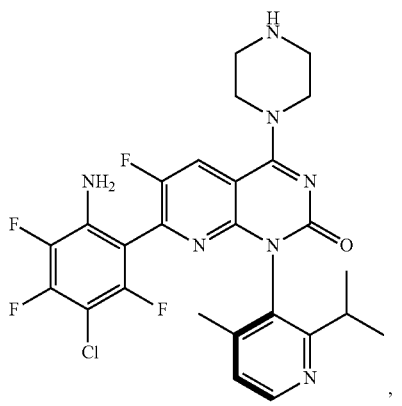
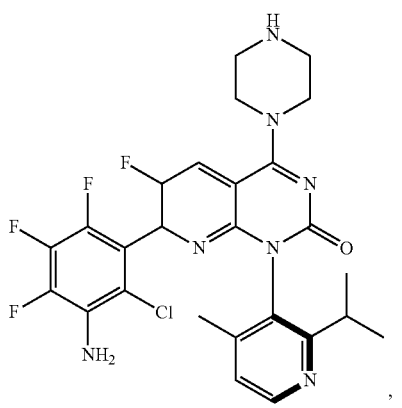
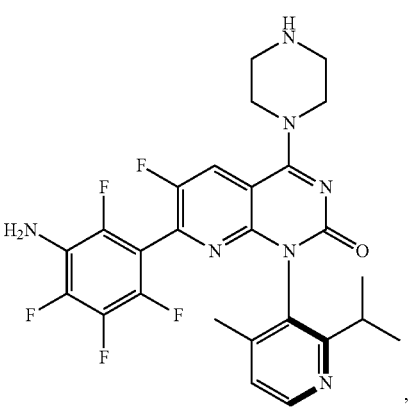
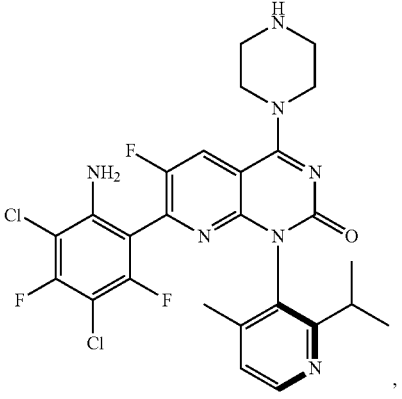

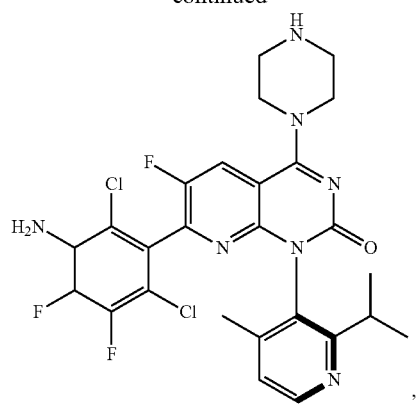
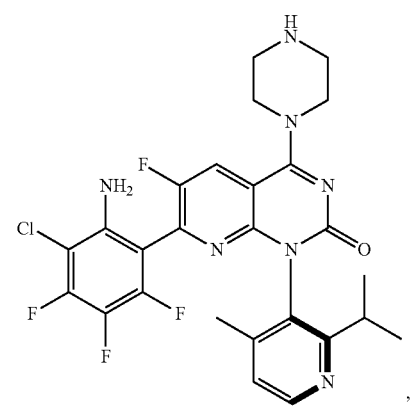
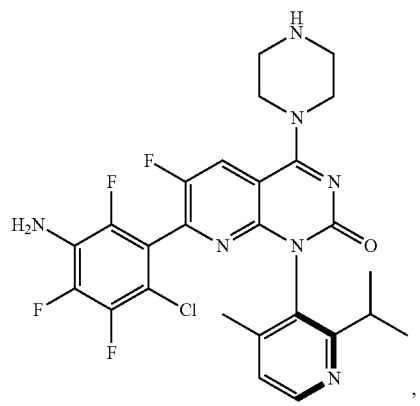
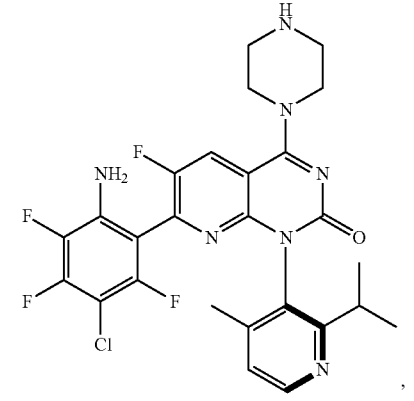
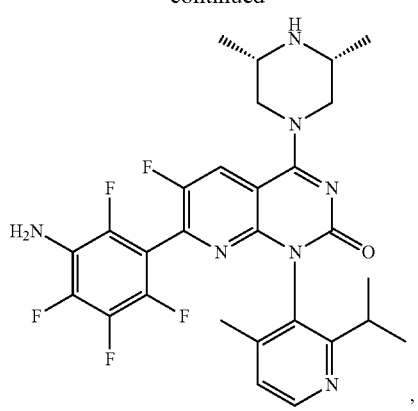
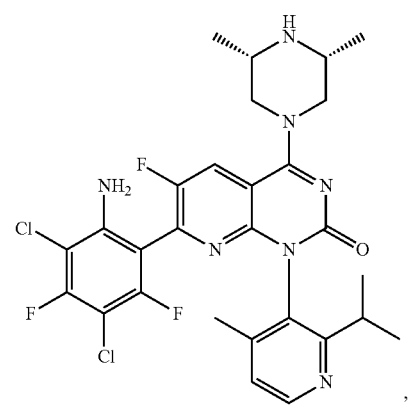
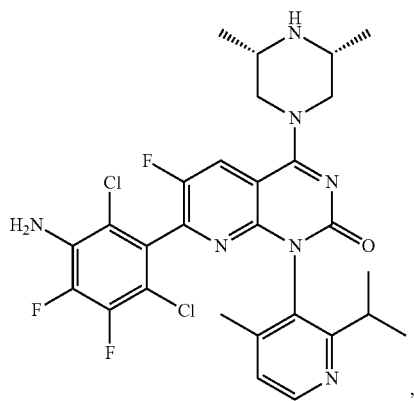
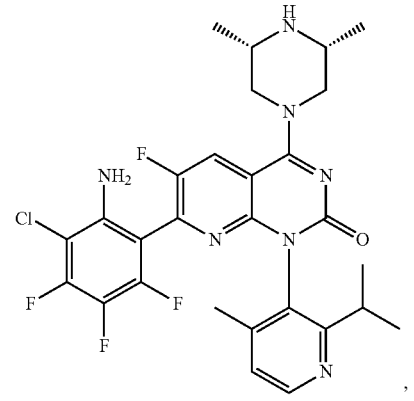

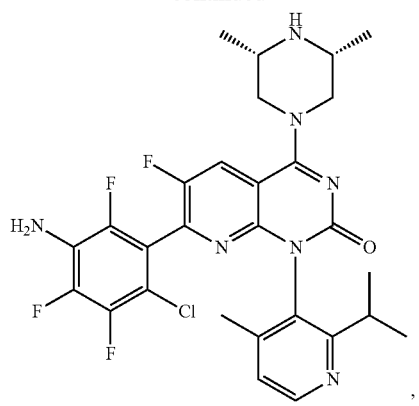
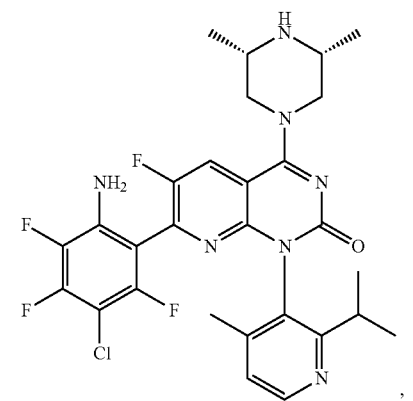
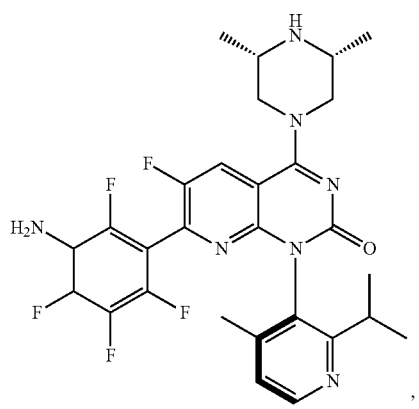
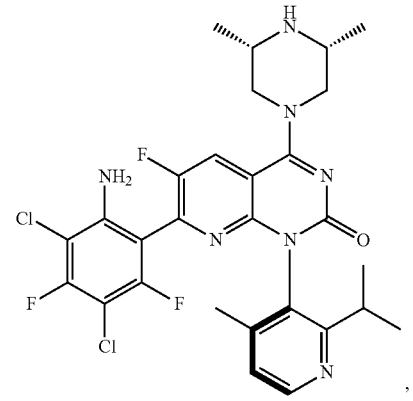
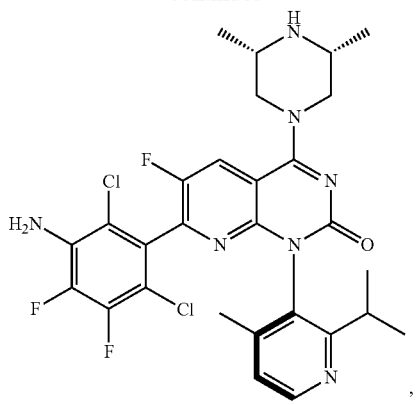
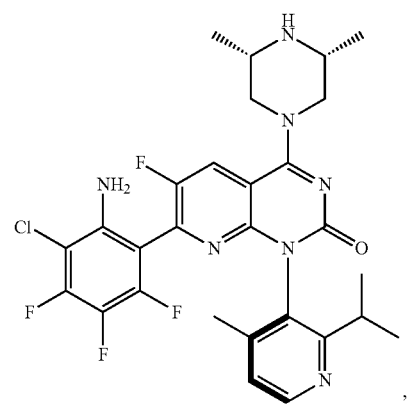
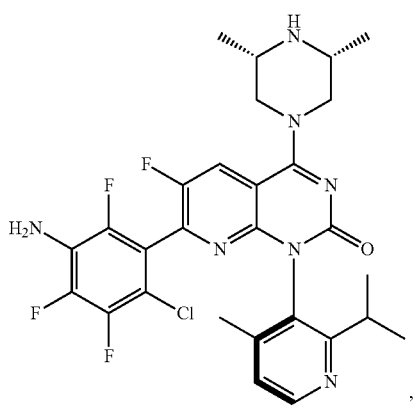
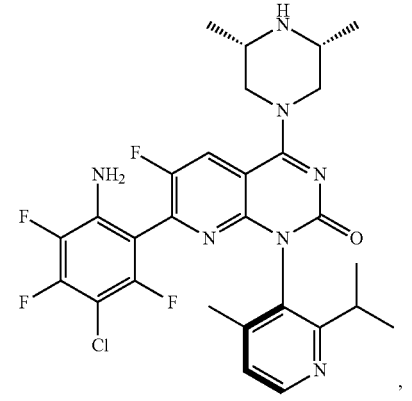

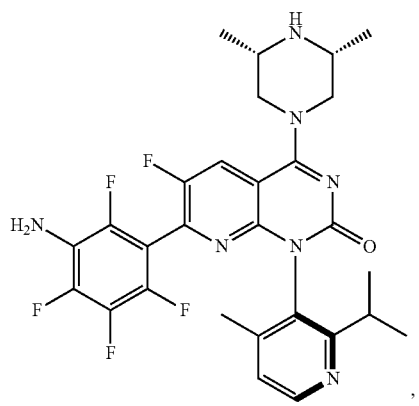

,

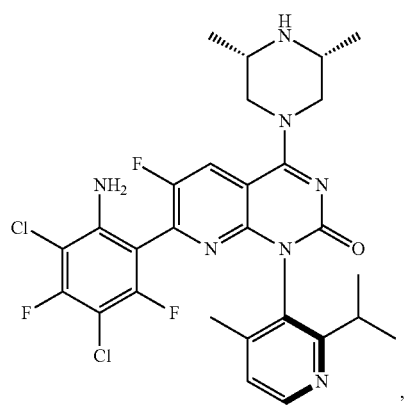

,

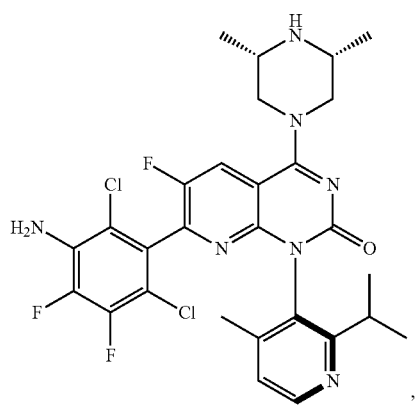

,

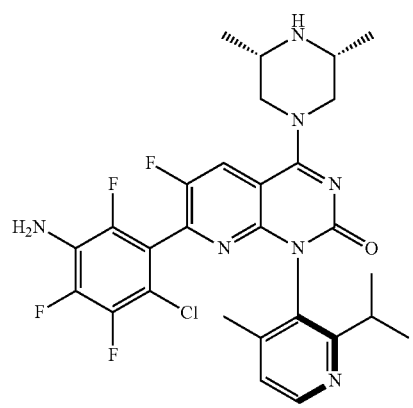

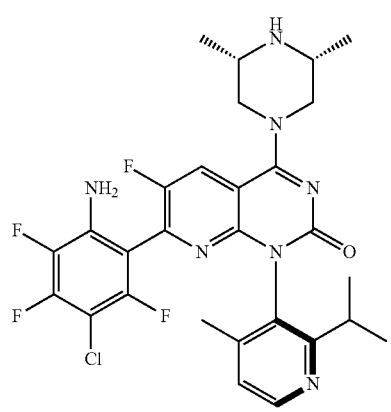

or

In another aspect, provided herein is a method for preparing the compound of formula (I'), the stereoisomer thereof, the atropisomer thereof, the pharmaceutically acceptable salt thereof, the pharmaceutically acceptable salt of the stereoisomer thereof or the pharmaceutically acceptable salt of the atropisomer thereof of the present invention, the method comprises a reaction between an intermediate of formula (IV') and a compound of formula(V') according to the following reaction Scheme 3 under a basic condition:

Scheme 3:

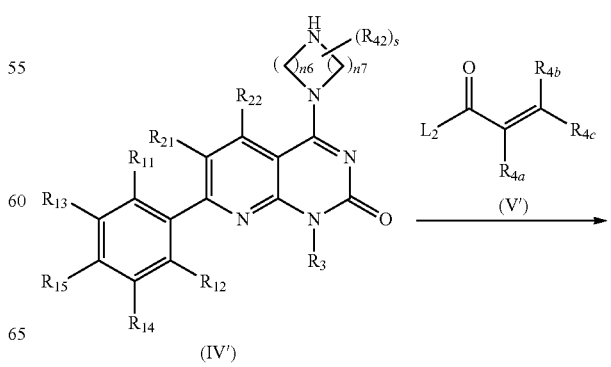

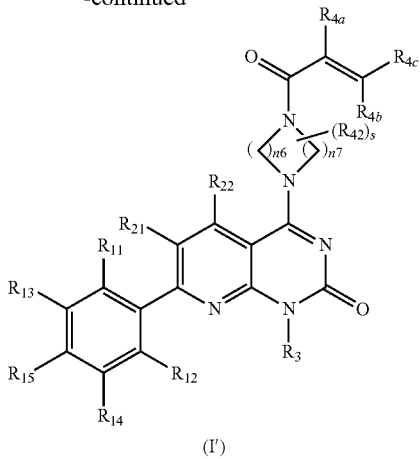

(I')

Wherein:

the $L_2$ in the compound of formula(V') is a leaving group; preferably, the leaving group is selected from halogen, —OS(O)$_2$CF$_3$ or -OTs; more preferably, the halogen is selected from —F, —Cl, —Br, or —I; more preferably, the leaving group is —Cl or —Br;

$R_{11}$, $R_{12}$, $R_{13}$, $R_{14}$, $R_{15}$, $R_{21}$, $R_{22}$, $R_3$, $R_{42}$, $n_6$, $n_7$ or s in the formula (IV') or formula (I') is defined as in the present invention; and $R_{4a}$, $R_{4b}$ or $R_{4c}$ in formula (IV') is defined as in the present invention; preferably, $R_{4a}$, $R_{4b}$ or $R_{4c}$ is hydrogen.

In another aspect, provided herein is a pharmaceutical composition comprising the compound of formula (I), the stereoisomer thereof, the atropisomer thereof, the pharmaceutically acceptable salt thereof, the pharmaceutically acceptable salt of the stereoisomer thereof or the pharmaceutically acceptable salt of the atropisomer thereof of the present invention, and at least one pharmaceutically acceptable excipient.

In some embodiments, the said compound in a weight ratio to the said excipient within the range from about 0.0001 to about 10. In some embodiments, the said compound in a weight ratio to the said excipient within the range from about 0.01 to about 0.8. In some embodiments, the said compound in a weight ratio to the said excipient within the range from about 0.02 to about 0.2. In some embodiments, the said compound in a weight ratio to the said excipient within the range from about 0.05 to about 0.15.

In another aspect, provided herein is use of the compound of formula (I), the stereoisomer thereof, the atropisomer thereof, the pharmaceutically acceptable salt thereof, the pharmaceutically acceptable salt of the stereoisomer thereof or the pharmaceutically acceptable salt of the atropisomer thereof of the present invention or the pharmaceutical composition of the present invention for the manufacture of a medicament for the treatment of cancer related to KRAS G12C mutant protein. In some embodiments, the cancer is selected from blood cancer, pancreatic cancer, colon cancer, rectal cancer, colorectal cancer or lung cancer. In some embodiments, the blood cancer is selected from acute myeloid leukemia or acute lymphocytic leukemia; the lung cancer is selected from non-small cell lung cancer or small cell lung cancer.

In another aspect, there is provided that a method of treating a subject having cancer related to KRAS G12C mutant protein, said method comprising administering to the subject a therapeutically effective amount of the compound of formula (I), the stereoisomer thereof, the atropisomer thereof, the pharmaceutically acceptable salt thereof, the pharmaceutically acceptable salt of the stereoisomer thereof or the pharmaceutically acceptable salt of the atropisomer thereof of the present invention; or the pharmaceutical composition of the present invention. In some embodiments, the cancer is selected from blood cancer, pancreatic cancer, colon cancer, rectal cancer, colorectal cancer or lung cancer. In some embodiments, the blood cancer is selected from acute myeloid leukemia or acute lymphocytic leukemia; the lung cancer is selected from non-small cell lung cancer or small cell lung cancer.

In another aspect, provided herein is a compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof of the present invention; or the pharmaceutical composition of the present invention for use in the treatment of cancer related into KRAS G12C mutant protein. In some embodiments, the cancer is selected from blood cancer, pancreatic cancer, colon cancer, rectal cancer, colorectal cancer or lung cancer. In some embodiments, the blood cancer is selected from acute myeloid leukemia or acute lymphocytic leukemia; the lung cancer is selected from non-small cell lung cancer or small cell lung cancer.

Definition

The term "halogen" or "halo", as used herein, unless otherwise indicated, means fluoro, chloro, bromo or iodo. The preferred halogen groups include —F, —Cl and —Br. The more preferred halogen groups include —F and —Cl.

The term "alkyl", as used herein, unless otherwise indicated, includes saturated monovalent hydrocarbon radicals having straight or branched. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Similarly, $C_{1-6}$, as in $C_{1-6}$alkyl is defined to identify the group as having 1, 2, 3, 4, 5 or 6 carbon atoms in a linear or branched arrangement.

The term "alkylene" means a difunctional group obtained by removal of a hydrogen atom from an alkyl group that is defined above. For example, methylene (i.e., —CH$_2$—), ethylene (i.e., —CH$_2$—CH$_2$— or —CH(CH$_3$)—) and propylene (i.e., —CH$_2$—CH$_2$, —CH$_2$—, —CH(—CH$_2$—CH$_3$)— or —CH$_2$—CH(CH$_3$)—).

The term "alkenyl" means a straight or branch-chained hydrocarbon radical containing one or more double bonds and typically from 2 to 20 carbon atoms in length. For example, "$C_{2-6}$alkenyl" contains from 2 to 6 carbon atoms. Alkenyl group include, but are not limited to, for example, ethenyl, propenyl, butenyl, 2-methyl-2-buten-1-yl, heptenyl, octenyl and the like.

The term "alkynyl" contains a straight or branch-chained hydrocarbon radical containing one or more triple bonds and typically from 2 to 20 carbon atoms in length. For example, "$C_{2-6}$alkynyl" contains from 2 to 6 carbon atoms. Representative alkynyl groups include, but are not limited to, for example, ethynyl, 1-propynyl, 1-butynyl, heptynyl, octynyl and the like.

The term "alkoxy" radicals are oxygen ethers formed from the previously described alkyl groups.

The term "aryl" or "aryl ring", as used herein, unless otherwise indicated, refers to an unsubstituted or substituted mono or polycyclic aromatic ring system only containing carbon ring atoms. The preferred aryls are mono cyclic or bicyclic 6-10 membered aromatic ring systems. Phenyl and naphthyl are preferred aryls.

The term "heterocyclic" or "heterocyclic ring", as used herein, unless otherwise indicated, refers to unsubstituted and substituted mono or polycyclic non-aromatic ring system containing one or more ring heteroatom(s), which comprising monocyclic heterocyclic (ring), bicyclic heterocyclic (ring), bridged heterocyclic (ring), fused heterocyclic (ring) or spiro heterocyclic (ring). Preferred heteroatoms include N, O, and S, including N-oxides, sulfur oxides, and dioxides. Preferably the heterocyclic (ring) is three to ten membered and is either fully saturated or has one or more degrees of unsaturation. Multiple degrees of substitution, preferably one, two or three, are included within the present definition of heterocyclic (ring). Examples of such heterocyclic groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl" or "heteroaryl ring", as used herein, unless otherwise indicated, represents an aromatic ring system containing carbon(s) and at least one heteroatom. Heteroaryl or heteroaryl ring may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junction, for example, bycyclic heteroaryl is a polycyclic heteroaryl. Bicyclic heteroaryl rings may contain from 8 to 12 member atoms. Monocyclic heteroaryl rings may contain from 5 to 8 member atoms (cabons and heteroatoms). Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "carbocyclic" or "carbocyclic ring" refers to a substituted or unsubstituted monocyclic ring, bicyclic ring, bridged ring, fused ring, sipiro ring non-aromatic ring system only containing carbon atoms.

The carbocyclic (ring) contain cycloalkyl without substituted degrees and carbocyclic with one or more substituted degrees. Examplary "cycloalkyl" groups includes but not limited to, cyclopropyl, cyclobutyl, cyclopentyl, cyclohexyl and so on.

The term "oxo" refers to oxygen atom together with the attached carbon atom forms the group

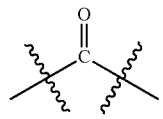 [SMILES: *C(*)=O]

The term "—$C_{1-6}$alkylene-N($C_{1-6}$alkyl)$_2$" refers to the —$C_{1-6}$alkyl as defined above substituted by —N($C_{1-6}$alkyl)$_2$.

The term "—$C_{1-6}$alkylene-CN" refers to the —$C_{1-6}$alkyl as defined above substituted by —CN.

The term "heteroalkyl" refers to the presence of heteroatoms between any two carbon atoms in the alkyl group as defined above, such as N or O atoms. For example, "hetero$C_{2-6}$alkyl" means that there are N atom or O atom between any two carbon atoms in the $C_{2-6}$ alkyl group, including but not limited to —$CH_2OCH_3$, —$CH_2CH_2OCH_3$, —$CH_2NHCH_3$, or —$CH_2N(CH_3)_2$ and the like.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention.

The compounds of the present invention may also be present in the form of pharmaceutically acceptable salt(s). For use in medicine, the salts of the compounds of this invention refer to non-toxic "pharmaceutically acceptable salt(s)". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The present invention includes all stereoisomers of the compound and pharmaceutically acceptable salts thereof. Further, mixtures of stereoisomers as well as isolated specific stereoisomers are also included. During the course of the synthetic procedures used to prepare such compounds or in using racemization or epimerization procedures known to those skilled in the art, the products of such procedures can be a mixture of stereoisomers.

The term "stereoisomer" as used in the present invention refers to an isomer in which atoms or groups of atoms in the molecule are connected to each other in the same order but differ in spatial arrangement, including conformational isomers and conformational isomers. The configuration isomers include geometric isomers and optical isomers, and optical isomers mainly include enantiomers and diastereomers. The invention includes all possible stereoisomers of the compound.

Certain of the compounds provided herein may exist as atropisomers, which are conformational stereoisomers that occur when rotation about a single bond in the molecule is prevented, or greatly slowed, as a result of steric interactions with other pails of the molecule. The compounds provided herein include all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^{1}H$(hydrogen), $^{2}H$(deuterium) and $^{3}H$(tritium). They are also commonly denoted as D for deuterium and T for tritium. In the application, $CD_3$ denotes a methyl group wherein all of the hydrogen atoms are deuterium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent.

When a tautomer of the compound exists, the present invention includes any possible tautomers and pharmaceutically acceptable salts thereof, and mixtures thereof, except where specifically stated otherwise.

The pharmaceutical compositions of the present invention comprise the compound (or the stereoisomer, the astropisomer thereof, the pharmaceutically acceptable salt thereof, the pharmaceutically acceptable salt of the stereoisomer, or the pharmaceutically acceptable salt of the astropisomer) as an active ingredient, and a pharmaceutically acceptable carrier and optionally other adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds or a prodrug or a metabolite or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The pharmaceutical carrier/excipient employed can be, for example, a solid, liquid or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 0.05 to about 95 percent of the total composition.

Unit dosage forms will generally contain between from about 0.01 mg to about 2 g of the active ingredient, typically 0.01 mg, 0.02 mg, 1 mg, 2 mg, 3 mg, 4 mg, 5 mg, 6 mg, 7 mg, 8 mg, 9 mg, 10 mg, 25 mg, 50 mg, 100 mg, 200 mg, 300 mg, 400 mg, 500 mg, 600 mg, 800 mg, 1000 mg, 1500 mg or 2000 mg.

Pharmaceutical compositions of the present invention suitable for parenteral administration may be prepared as solutions or suspensions of the active compounds in water. A suitable surfactant can be included such as, for example, hydroxypropyl cellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder or the like. Further, the compositions can be in a form suitable for use in transdermal devices. These formulations may be prepared, utilizing a compound of this invention or a pharmaceutically acceptable salt thereof, via conventional processing methods. As an example, a cream or ointment is prepared by admixing hydrophilic material and water, together with about 0.05 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound or pharmaceutically acceptable salts thereof, may also be prepared in powder or liquid concentrate form.

Generally, dosage levels on the order of from about 0.001 mg/kg to about 150 mg/kg of body weight per day are useful in the treatment of the above-indicated conditions or alternatively about 0.05 mg to about 7 g per patient per day. For example, inflammation, cancer, psoriasis, allergy/asthma, disease and conditions of the immune system, disease and conditions of the central nervous system (CNS), may be effectively treated by the administration of from about 0.001 to 50 mg of the compound per kilogram of body weight per day or alternatively about 0.05 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

EXAMPLES

Figure 1:
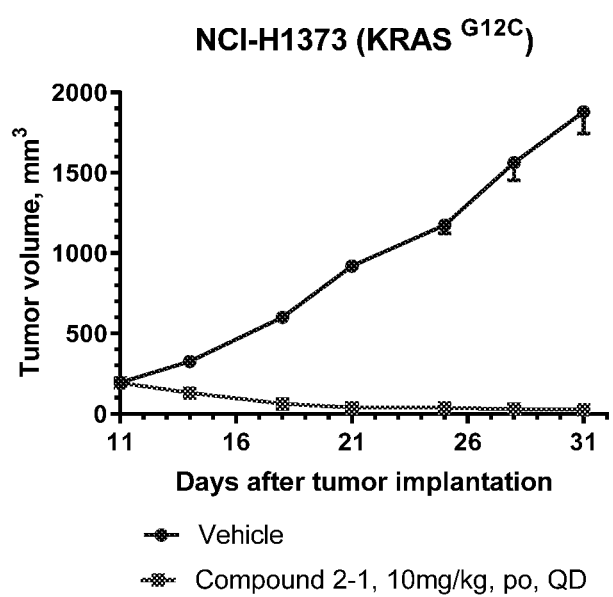
FIG. 1 is the graph of tumor volume varying with the days after tumor implantation after administration of Compound 2-1 or vehicle in NCI-H1373 (KRAS$^{G12C}$) xenograft model.

Compounds of the present invention can be synthesized from commercially available reagents using the synthetic methods described herein. The examples which outline specific synthetic route below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

The following Examples are provided to better illustrate the present invention. All parts and percentages are by weight and all temperatures are degrees Celsius, unless explicitly stated otherwise. The following abbreviations in Table 1 have been used in the examples:

TABLE 1

| | |
|---|---|
| MeOH | Methanol |
| EtOH | Ethanol |
| DCM | Dichloromethane |
| TEA | Triethylamine |
| TFA | Trifluoroacetic acid |
| DMF | N,N-Dimethylformamide |
| DMA | N,N-dimethylacetamide |
| THF | Tetrahydrofuran |
| MeCN/ACN | Acetonitrile |
| HATU | 2-(7-Azabenzotriazol-1-yl)-N,N,N',N'-tetramethyluronium hexafluorophosphate |
| EDCI | 1-Ethyl-3-(3-dimethylaminopropyl)carbodiimide hydrochloride |
| HOBT | 1-Hydroxybenzotriazole |
| LiHMDS | Lithium Hexamethyldisilazide |
| Hunig's base/ DIEA/DIPEA | N,N-Diisopropylethylamine |
| EA | Ethyl acetate |
| min | Minute(s) |
| h | Hour(s) |
| Pre-TLC | Preparative thin layer chromatography |
| prep-HPLC | Preparative High Performance Liquid Chromatography |
| SFC | Supercritical fluid chromatography |
| Pd(dppf)Cl$_2$ | [1,1'-Bis(diphenylphosphino)ferrocene]dichloropalladium(II) |
| R.T./r.t./RT | Room temperature(20° C.~30° C.) |
| AcOH | Acetic acid |
| Pd(PPh$_3$)$_4$ | Tetrakis(triphenylphosphine)palladium |
| NCS | N-Chlorosuccinimide |
| Hex | n-Hexane |
| PPTS | Pyridinium 4-toluenesulfonate |
| IPA | Isopropanol |
| DHP | 3,4-Dihydro-2H-pyran |
| a.q./aq | Aqueous |
| AcOK/KOAc | Potassium acetate |
| NMP | Methyl-2-pyrrolidinone |

Example 1

4-((S)-4-acryloyl-2-methylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (Compound 1); (M)-4-((S)-4-acryloyl-2-methylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one; and (P)-4-((S)-4-acryloyl-2-methylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one Compound 1

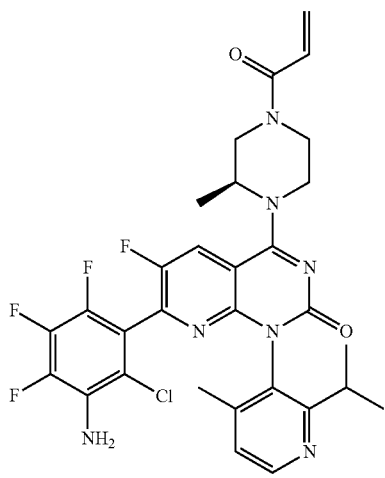

and

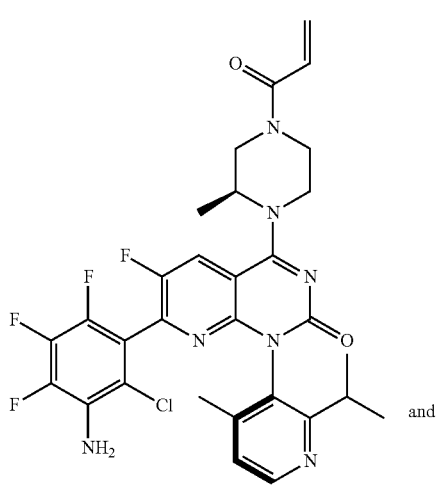

-continued

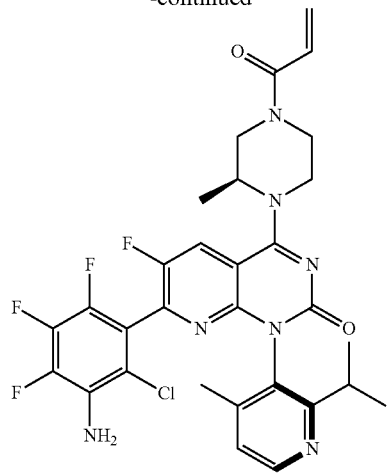

Step 1. 2,6-dichloro-5-fluoro-N-((2-isopropyl-4-methylpyridin-3-yl)carbamoyl)nicotinamide Into a 500-mL round-bottom flask purged with nitrogen and maintained with an inert atmosphere of nitrogen, was placed 2,6-dichloro-5-fluoronicotinic acid (25.218 g, 120.09 mmol) and $SOCl_2$ (100 mL).

The mixture was stirred at 80° C. for 2 h. The reaction was cooled to room temperature and concentrated under vacuum. The mixture was diluted by $CH_3CN$ (20 mL), this was followed by the addition of $NH_3 \cdot H_2O$ (100 mL) in dropwise at 0° C. The mixture was stirred at RT for 1 h. The solid was collected by filtration to give 25.101 g (crude) of 2,6-dichloro-5-fluoronicotinamide which was used directly in the next step.

Into a 500-mL round-bottom flask purged with nitrogen and maintained with an inert atmosphere of nitrogen, was placed 2,6-dichloro-5-fluoronicotinamide (25.101 g, crude) and THF (200 mL). This was followed by the addition of oxalyl chloride (21.884 g, 172.42 mmol) in dropwise. The mixture was stirred at 80° C. for 2 h. The resulting solution was concentrated under vacuum. This was followed by the addition of 2-isopropyl-4-methylpyridin-3-amine (19.830 g, 132.11 mmol) at 0° C. The mixture was stirred at RT for 1 h. The reaction was then quenched by the addition of water (200 mL). The resulting solution was extracted with dichloromethane (3×200 mL). The organic layers were combined and washed with brine (200 mL), dried over anhydrous $Na_2SO_4$. The residue was concentrated under vacuum and applied onto a silica gel column eluted with EA/hexane (v/v=1:2). This resulted in 42.01 g (91%) of 2,6-dichloro-5-fluoro-N-((2-isopropyl-4-methylpyridin-3-yl)carbamoyl)nicotinamide as red oil. LCMS: m/z=385 [M+1]$^+$.

Step 2. 7-chloro-6-fluoro-1-(2-isopropyl-4-methylpyridin-3-yl)pyrido[2,3-d]pyrimidine-2,4(1H,3H)-dione Into a 500-mL round-bottom flask purged with nitrogen and maintained with an inert atmosphere of nitrogen, was placed 2,6-dichloro-5-fluoro-N-((2-isopropyl-4-methylpyridin-3-yl)carbamoyl) nicotinamide (42.01 g, 109.83 mmol), THF (200 mL) and stirred at room temperature. NaH (9.493 g, 237.33 mmol) was added at −10° C. The mixture was stirred at RT for 2 h. The reaction was poured into water (200 mL). The resulting solution was extracted with dichloromethane (3×100 mL). The organic layers were combined and washed with brine (100 mL), dried over anhydrous Na$_2$SO$_4$. The residue was concentrated under vacuum and applied onto a silica gel column eluted with EA/hexane (v/v=61/4). This resulted in 25.11 g (65%) of 7-chloro-6-fluoro-1-(2-isopropyl-4-methylpyridin-3-yl)pyrido[2,3-d]pyrimidine-2,4(1H,3H)-dione as red oil. LCMS: m z=349 [M+1]$^+$.

Step 3. tert-butyl (S)-4-(7-chloro-6-fluoro-1-(2-isopropyl-4-methylpyridin-3-yl)-2-oxo-1,2-dihydro pyrido[2,3-d]pyrimidin-4-yl)-3-methylpiperazine-1-carboxylate Into a 500-mL round-bottom flask purged with nitrogen and maintained with an inert atmosphere of nitrogen, was placed 7-chloro-6-fluoro-1-(2-isopropyl-4-methylpyridin-3-yl)pyrido[2,3-d]pyrimidine-2,4(1H,3H)-dione (25.074 g, 74.96 mmol), acetonitrile (200 mL), POCl$_3$ (45.97 g, 299.81 mmol) and DIEA (58.12 g, 449.70 mmol). The mixture was stirred at 80° C. for 2 h. The reaction was cooled to room temperature and concentrated under vacuum. This resulted in 4,7-dichloro-6-fluoro-1-(2-isopropyl-4-methylpyridin-3-yl)pyrido[2,3-d]pyrimidin-2(1H)-one (30 g, crude) which was used directly in the next step.

Into a 500-mL round-bottom flask purged with nitrogen and maintained with an inert atmosphere of nitrogen, was placed 4,7-dichloro-6-fluoro-1-(2-isopropyl-4-methylpyridin-3-yl)pyrido[2,3-d]pyrimidin-2(1H)-one (30 g, crude), acetonitrile (200 mL), DIEA (58.12 g, 449.70 mmol) and tert-butyl (S)-3-methylpiperazine-1-carboxylate (15.801 g, 78.90 mmol). The reaction mixture was stirred for 2 h at room temperature. The reaction was then quenched by the addition of water (500 mL). The resulting solution was extracted with ethyl acetate (3×500 mL). The organic layers were combined and washed with brine (500 mL), dried over anhydrous Na$_2$SO$_4$, filtered and concentrated under vacuum. The residue was purified by silica gel column eluted with EA/hexane (v/v=4/1). This resulted in 15.18 g (38.14% in two steps) of tert-butyl (S)-4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate as yellow solid. LCMS: m z=531 [M+1]$^+$.

Step 4. (S)-4-(4-acryloyl-2-methylpiperazin-1-yl)-7-chloro-6-fluoro-1-(2-isopropyl-4-methylpyridin-3-yl)pyrido[2,3-d]pyrimidin-2(1H)-one Into a 250-mL round-bottom flask purged with nitrogen and maintained with an inert atmosphere of nitrogen, was placed tert-butyl (S)-4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (14.708 g, 27.698 mmol), DCM (20 mL) and TFA (4 ml). The reaction mixture was stirred at room temperature for 2 h. The reaction mixture was concentrated under vacuum. The residue was dissolved by DCM (20 mL) in a 250-mL round-bottom flask. This was followed by the addition of DIEA (4 mL). The reaction mixture was cooled to 0° C. and acryloyl chloride (6.756 g, 74.65 mmol) was added. The mixture stirred at room temperature for 1 h. The reaction was then quenched by the addition of water (100 mL). The resulting solution was extracted with ethyl acetate (3×100 mL). The organic layers were combined and washed with brine (100 mL), dried over anhydrous Na$_2$SO$_4$, filtered and concentrated under vacuum. The residue was purified by silica gel column eluted with EA/hexane (v/v=4/1). This resulted in 16.459 g of (S)-4-(4-acryloyl-2-methylpiperazin-1-yl)-7-chloro-6-fluoro-1-(2-isopropyl-4-methylpyridin-3-yl)pyrido[2,3-d]pyrimidin-2(1H)-one as red oil. LCMS: m z=485 [M+1]$^+$.

Step 5. (S)-4-(4-acryloyl-2-methylpiperazin-1-yl)-7-(5-amino-2,3,4-trifluorophenyl)-6-fluoro-1-(2-isopropyl-4-methylpyridin-3-yl)pyrido[2,3-d]pyrimidin-2(1H)-one Into a 20-mL sealed tube purged with nitrogen and maintained with an inert atmosphere of nitrogen, was placed (S)-4-(4-acryloyl-2-methylpiperazin-1-yl)-7-chloro-6-fluoro-1-(2-isopropyl-4-methylpyridin-3-yl) pyrido[2,3-d]pyrimidin-2(1H)-one (1.485 g, 3.06 mmol), (5-amino-2,3,4-trifluorophenyl)boronic acid (0.773 g, 4.09 mmol), Pd(PPh$_3$)$_4$ (0.356 g, 0.31 mmol), Na$_2$CO$_3$ (0.372 g, 3.51 mmol), dioxane (10 mL) and water (2 mL). The reaction mixture was stirred at 80° C. for 1 h. The reaction mixture was filtered and concentrated under vacuum. The residue was purified by silica gel column eluted with EA/hexane (v/v=2/1). This resulted in 1.386 g (76%) of (S)-4-(4-acryloyl-2-methylpiperazin-1-yl)-7-(5-amino-2,3,4-trifluorophenyl)-6-fluoro-1-(2-isopropyl-4-methylpyridin-3-yl)pyrido[2,3-d]pyrimidin-2(1H)-one as yellow solid. LCMS: m z=596 [M+1]$^+$.

Step 6. 4-((S)-4-acryloyl-2-methylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (Compound 1)

Into a 100-mL round-bottom flask purged with nitrogen and maintained with an inert atmosphere of nitrogen, was placed (S)-4-(4-acryloyl-2-methylpiperazin-1-yl)-7-(5-amino-2,3,4-trifluorophenyl)-6-fluoro-1-(2-isopropyl-4-methylpyridin-3-yl)pyrido[2,3-d]pyrimidin-2(1H)-one (1.444 g, 2.42 mmol), NCS (1.268 g, 9.50 mmol) and AcOH (20 mL). The mixture was stirred at r.t. for 1 d. The reaction was then quenched by the addition of water (10 mL). The resulting solution was extracted with ethyl acetate (3×10 mL). The organic layers were combined and washed with brine (1×50 mL), dried over anhydrous Na$_2$SO$_4$, filtered and concentrated under vacuum. The residue was purified by Prep-HPLC eluted with CH$_3$CN/H$_2$O (v/v=6/4). This resulted in 69 mg (5%) of 4-((S)-4-acryloyl-2-methylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (Compound 1) as yellow solid. LCMS: m z=630 [M+1]$^+$.

$^1$H NMR (400 MHz, CD$_3$OD) δ 8.38-8.222 (m, 2H), 7.16 (t, J=4.1 Hz, 1H), 6.87-6.60 (m, 1H), 6.23 (d, J=16.0 Hz, 1H), 5.75 (dd, J=10.6, 1.8 Hz, 1H), 5.13-4.89 (m, 1H), 4.59-4.26 (m, 2H), 4.22-3.94 (m, 1H), 3.92-3.44 (m, 3H), 2.75 (s, 1H), 1.93 (d, J=12.4 Hz, 3H), 1.50-1.32 (m, 3H), 1.10 (d, J=6.4 Hz, 3H), 1.01-0.82 (m, 3H).

Step 7. 4-((S)-4-acryloyl-2-methylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (the first eluting isomer, Compound 1-1) & 4-((S)-4-acryloyl-2-methylpiperazin-1-yl)-7-(3-amino-2-chloro-4,5,6-trifluorophenyl)-6-fluoro-1-(2-isopropyl-4-methylpyridin-3-yl) pyrido[2,3-d]pyrimidin-2(1H)-one (the second eluting isomer, Compound 1-2)

The mixture of 4-((S)-4-acryloyl-2-methylpiperazin-1-yl)-7-(3-amino-2-chloro-4,5,6-trifluorophenyl)-6-fluoro-1-

(2-isopropyl-4-methylpyridin-3-yl)pyrido[2,3-d]pyrimidin-2(1H)-one atropisomers (140 mg) was purified by Chiral-Prep-HPLC with the following conditions: Column: CHIRALPAK IF, 2 cm×25 cm, 5 um; mobile phase: (Hexane:DCM(v/v=3:1)):IPA(v/v=4:1); detected wavelength: UV 220 nm. This resulted in 29 mg (20.7%) of 4-((S)-4-acryloyl-2-methylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (the first eluting isomer, Compound 1-1) as a yellow solid. LCMS: m z=630 [M+1]$^+$.

$^1$H NMR (400 MHz, CD$_3$OD) δ 8.48 (t, J=8.6 Hz, 1H), 8.37 (t, J=10.0 Hz, 1H), 7.44 (d, J=5.2 Hz, 1H), 6.84 (td, J=16.5, 10.9 Hz, 1H), 6.30 (t, J=15.7 Hz, 1H), 5.88-5.77 (m, 1H), 5.06 (s, 1H), 4.49 (dd, J=38.5, 12.4 Hz, 2H), 4.15 (dd, J=49.6, 13.5 Hz, 1H), 3.95-3.57 (m, 2H), 3.51-3.32 (m, 1H), 2.96 (s, 1H), 2.11 (t, J=14.0 Hz, 3H), 1.51 (s, 3H), 1.24 (d, J=6.8 Hz, 3H), 1.06 (dd, J=11.4, 6.9 Hz, 3H). And 28 mg (20.0%) of 4-((S)-4-acryloyl-2-methylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (the second eluting isomer, Compound 1-2) as a yellow solid. LCMS: m z=630 [M+1]$^+$.

$^1$H NMR (400 MHz, CD$_3$OD) δ 8.48 (t, J=8.6 Hz, 1H), 8.37 (t, J=10.0 Hz, 1H), 7.44 (d, J=5.2 Hz, 1H), 6.84 (td, J=16.5, 10.9 Hz, 1H), 6.30 (t, J=15.7 Hz, 1H), 5.88-5.77 (m, 1H), 5.06 (s, 1H), 4.49 (dd, J=38.5, 12.4 Hz, 2H), 4.15 (dd, J=49.6, 13.5 Hz, 1H), 3.95-3.57 (m, 2H), 3.51-3.32 (m, 1H), 2.96 (s, 1H), 2.11 (t, J=14.0 Hz, 3H), 1.51 (s, 3H), 1.24 (d, J=6.8 Hz, 3H), 1.06 (dd, J=11.4, 6.9 Hz, 3H).

Example 2

4-((S)-4-acryloyl-2-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 2); (M)-4-((S)-4-acryloyl-2-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 2-1); and (P)-4-((S)-4-acryloyl-2-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 2-2)

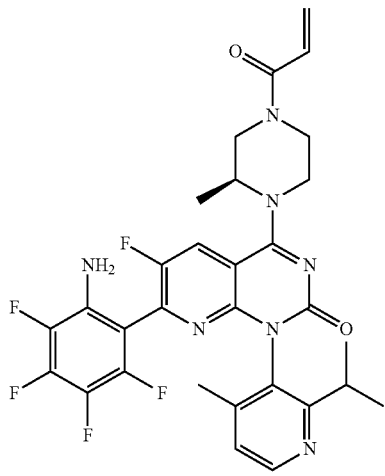

Compound 2

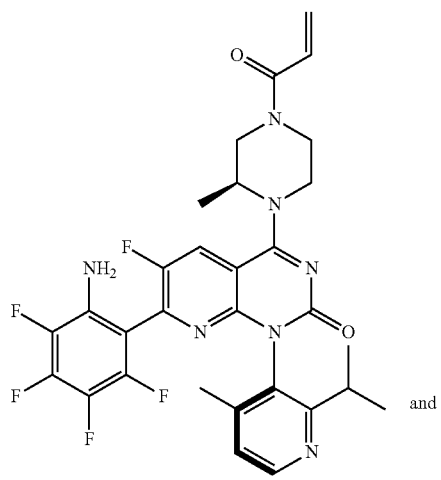

Compound 2-1 and

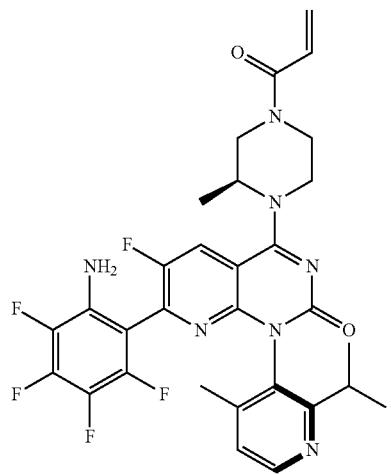

Compound 2-2

Step 1. 4-((S)-4-acryloyl-2-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 2)

Into a 20-mL round-bottom flask purged with nitrogen and maintained with an inert atmosphere of nitrogen was placed (S)-4-(4-acryloyl-2-methylpiperazin-1-yl)-7-chloro-6-fluoro-1-(2-isopropyl-4-methylpyridin-3-yl)pyrido[2,3-d]pyrimidin-2(1H)-one (0.71 g, 1.46 mmol), (2-amino-3,4,5,6-tetrafluorophenyl)boronic acid (1.512 g, 7.24 mmol), Pd(PPh$_3$)$_4$ (0.183 g, 0.16 mmol), Na$_2$CO$_3$ (0.491 g, 4.63 mmol), dioxane (8 mL) and water (2 mL). The reaction mixture was stirred at 80° C. for 1 h. The reaction mixture was filtered and concentrated under vacuum. The residue was purified by Prep-HPLC eluted with CH$_3$CN/H$_2$O (0.05% NH$_4$HCO$_3$) (v:v=2/1). This resulted in 0.181 g (30%) of 4-((S)-4-acryloyl-2-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 2) as yellow solid. LCMS: m/z=614 [M+1]$^+$.

$^1$H NMR (400 MHz, CD$_3$OD) δ 8.37 (d, J=4.4 Hz, 1H), 8.28 (s, 1H), 7.21 (s, 1H), 6.76 (d, J=12.2 Hz, 1H), 6.23 (d, J=15.6 Hz, 1H), 5.75 (d, J=10.4 Hz, 1H), 5.16-4.83 (m, 2H), 4.64-4.20 (m, 2H), 4.20-3.89 (m, 1H), 3.89-3.40 (m, 2H), 2.77 (s, 1H), 1.95 (s, 3H), 1.57-1.28 (m, 3H), 1.28-1.02 (m, 3H), 0.93 (d, J=5.5 Hz, 3H).

Step 2. (M)-tert-butyl (3S)-4-(7-(2-amino-3,4,5,6-tetrafluorophenyl)-6-fluoro-1-(2-isopropyl-4-methylpyridin-3-yl)-2-oxo-1,2-dihydropyrido[2,3-d]pyrimidin-4-yl)-3-methylpiperazine-1-carboxylate Into a reactor purged with nitrogen and maintained with an inert atmosphere of nitrogen was placed tert-butyl (3S)-4-{7-chloro-6-fluoro-(1M)-1-[4-methyl-2-(propan-2-yl)pyridin-3-yl]-2-oxo-1,2-dihydro pyrido[2,3-d]pyrimidin-4-yl}-3-methylpiperazine-1-carboxylate (1.0 eq) (which was on the page 64 and referred as "PIPAZOLINE" in the WO2020102730A1), Pd(dppf)Cl$_2$·CH$_2$Cl$_2$ (0.02 eq), NaOAc (4.0 eq) and dioxane (4.0V). This was followed by the addition of H$_2$O (3.0 V) at 65-85° C. Then (2-amino-3,4,5,6-tetrafluorophenyl)boronic acid (1.15 eq) in dioxane (2.70 V) and H$_2$O (0.30 V) was added. The reaction mixture was stirred at 75±5° C. for 1 h. Palladium was removed with sulfhydryl gel and crystallized with EA, MTBE and heptane to give (M)-tert-butyl (3S)-4-(7-(2-amino-3,4,5,6-tetrafluorophenyl)-6-fluoro-1-(2-isopropyl-4-methylpyridin-3-yl)-2-oxo-1,2-dihydropyrido[2,3-d]pyrimidin-4-yl)-3-methylpiperazine-1-carboxylate as light yellow solid. LCMS: m/z=660 [M+1]$^+$.

Step 3. (M)-4-((S)-4-acryloyl-2-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 2-1)

Into a reactor purged with nitrogen and maintained with an inert atmosphere of nitrogen was placed (M)-tert-butyl (3S)-4-(7-(2-amino-3,4,5,6-tetrafluorophenyl)-6-fluoro-1-(2-isopropyl-4-methylpyridin-3-yl)-2-oxo-1,2-dihydropyrido[2,3-d]pyrimidin-4-yl)-3-methylpiperazine-1-carboxylate (1.0 eq) and DCM (10 V). Trimethylsilyl trifluoromethanesulfonate (3.5 eq) was added at 5±5° C. The reaction was allowed to react for 1 h at 20±5° C. The reaction mixture was washed with K$_2$CO$_3$ aqueous solution and brine to give a solution of (M)-7-(2-amino-3,4,5,6-tetrafluorophenyl)-6-fluoro-1-(2-isopropyl-4-methylpyridin-3-yl)-4-((S)-2-methylpiperazin-1-yl)pyrido[2,3-d]pyrimidin-2(1H)-one. K$_3$PO$_4$ solution (5 V, 1.15 eq) was added to the solution of (M)-7-(2-amino-3,4,5,6-tetrafluorophenyl)-6-fluoro-1-(2-isopropyl-4-methyl pyridin-3-yl)-4-((S)-2-methylpiperazin-1-yl)pyrido[2,3-d]pyrimidin-2(1H)-one. This was followed by the addition of acryloyl chloride (1.15 eq) at 0-10° C. The reaction was separated, washed with 5% brine and concentrated under vacuum. The crude product was crystallized with EtOH to give (M)-4-((S)-4-acryloyl-2-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 2-1) LCMS: m/z=614 [M+1]$^+$.

$^1$H NMR (400 MHz, CD$_3$OD) δ 8.37 (d, J=4.8 Hz, 1H), 8.39-8.25 (m, 1H), 7.20 (d, J=4.6 Hz, 1H), 6.93-6.72 (m, 1H), 6.22 (d, J=15.9 Hz, 1H), 5.74 (d, J=10.5 Hz, 1H), 4.92 (s, 1H), 4.57-4.27 (m, 2H), 4.26-4.02 (m, 1H), 3.79-3.49 (m, 2H), 3.35-3.23 (m, 1H), 2.85-2.70 (m, 1H), 1.94 (s, 3H), 1.55-1.34 (m, 3H), 1.10 (d, J=6.6 Hz, 3H), 0.93 (d, J=6.5 Hz, 3H).

Step 4. (P)-4-((S)-4-acryloyl-2-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 2-2)

(P)-4-((S)-4-acryloyl-2-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 2-2) was afforded with the basically same procedure as the preparation of Compound 2-1 except that the tert-butyl (3S)-4-{7-chloro-6-fluoro-(1M)-1-[4-methyl-2-(propan-2-yl)pyridin-3-yl]-2-oxo-1,2-dihydropyrido[2,3-d]pyrimidin-4-yl}-3-methylpiperazine-1-carboxylate was replaced with tert-butyl (3S)-4-{7-chloro-6-fluoro-(1P)-1-[4-methyl-2-(propan-2-yl)pyridin-3-yl]-2-oxo-1,2-dihydropyrido[2,3-d]pyrimidin-4-yl}-3-methylpiperazine-1-carboxylate in the step 2. LCMS: m z=614 [M+1]$^+$.

$^1$H NMR (400 MHz, CD$_3$OD) δ 8.46 (d, J=5.0 Hz, 1H), 8.42-8.33 (m, 1H), 7.33-7.25 (m, 1H), 6.91-6.76 (m, 1H), 6.32 (dd, J=16.7, 4.7 Hz, 1H), 5.84 (dd, J=10.6, 1.9 Hz, 1H), 5.28-5.08 (m, 1H), 4.63-4.36 (m, 2H), 4.24-4.03 (m, 1H), 3.96-3.79 (m, 1H), 3.79-3.54 (m, 1H), 3.45-3.35 (m, 0.5H), 3.26-3.15 (m, 0.5H), 2.89-2.76 (m, 1H), 2.12-1.99 (m, 3H), 1.46 (d, J=6.6 Hz, 3H), 1.19 (d, J=6.8 Hz, 3H), 1.02 (d, J=6.7 Hz, 3H).

Example 3

4-(4-acryloylpiperazin-1-yl)-7-(2-amino-3,4,5,6-tetrafluorophenyl)-6-fluoro-1-(2-isopropyl-4-methyl pyridin-3-yl)pyrido[2,3-d]pyrimidin-2(1H)-one (Compound 3); (M)-4-(4-acryloylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one; and (P)-4-(4-acryloylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one

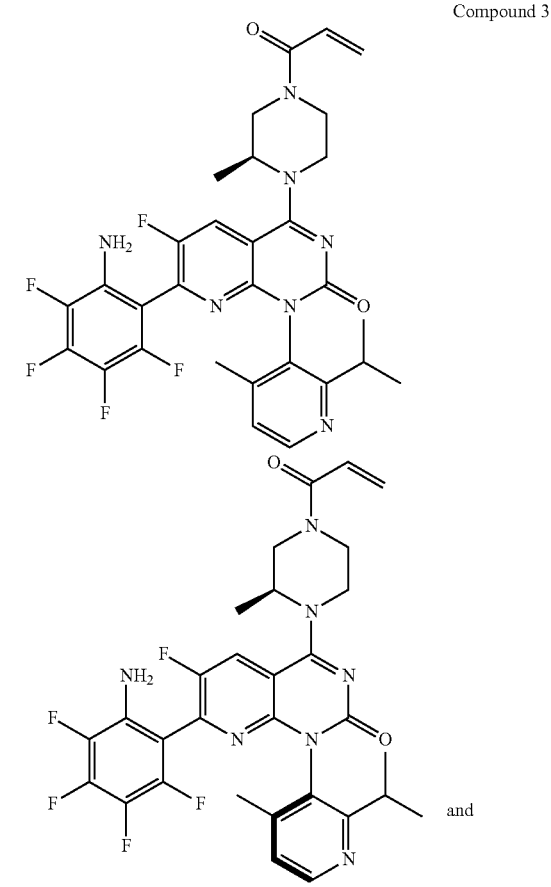

Compound 3 and

-continued

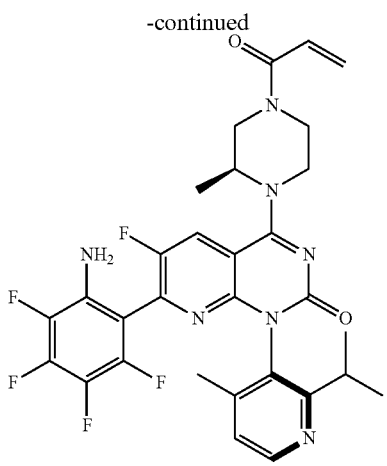

Step 1. tert-butyl 4-(7-chloro-6-fluoro-1-(2-isopropyl-4-methylpyridin-3-yl)-2-oxo-1,2-dihydro pyrido[2,3-d]pyrimidin-4-yl)piperazine-1-carboxylate Into a 500-mL round-bottom flask purged with nitrogen and maintained with an inert atmosphere of nitrogen, was placed 7-chloro-6-fluoro-4-hydroxy-1-(2-isopropyl-4-methylpyridin-3-yl)pyrido[2,3-d]pyrimidin-2(1H)-one (8.24 g, 23.63 mmol), POCl₃ (7.37 g, 48.06 mmol), DIEA (8.32 g, 64.37 mmol) and acetonitrile (80 mL). The mixture was stirred at 70° C. for 1 h. The reaction was cooled to room temperature and concentrated under vacuum. This resulted in 4,7-dichloro-6-fluoro-1-(2-isopropyl-4-methylpyridin-3-yl)pyrido[2,3-d]pyrimidin-2(1H)-one which was used directly in next step.

Into a 250-mL round-bottom flask purged with nitrogen and maintained with an inert atmosphere of nitrogen, was placed 4,7-dichloro-6-fluoro-1-(2-isopropyl-4-methylpyridin-3-yl)pyrido[2,3-d]pyrimidin-2(1H)-one (crude) and acetonitrile (80 mL). DIEA (6.01 g, 46.50 mmol) and tert-butyl piperazine-1-carboxylate (544 g, 29.21 mmol) were added. The reaction mixture was stirred for 1 h at room temperature. The reaction was then quenched by the addition of water (50 mL). The reaction was concentrated under vacuum. The residue was purified by silica gel column eluted with EA/hexane(v/v=3/2). This resulted in 4.38 g (36% in two steps) of tert-butyl 4-(7-chloro-6-fluoro-1-(2-isopropyl-4-methylpyridin-3-yl)-2-oxo-1,2-dihydropyrido[2,3-d]pyrimidin-4-yl)piperazine-1-carboxylate as yellow solid. LCMS: m z=517 [M+1]⁺.

Step 2. 4-(4-acryloylpiperazin-1-yl)-7-chloro-6-fluoro-1-(2-isopropyl-4-methylpyridin-3-yl)pyrido[2,3-d]pyrimidin-2(1H)-one Into a 250-mL round-bottom flask purged with nitrogen and maintained with an inert atmosphere of nitrogen, was placed tert-butyl 4-(7-chloro-6-fluoro-1-(2-isopropyl-4-methylpyridin-3-yl)-2-oxo-1,2-dihydropyrido[2,3-d]pyrimidin-4-yl)piperazine-1-carboxylate (4.37 g, 8.45 mmol), TFA (15 ml) and DCM (40 mL). The reaction mixture was stirred at room temperature for 0.5 h. The reaction mixture was concentrated under vacuum. The residue was dissolved by DCM (40 mL) in 100-mL round-bottom flask. TEA (5.30 g, 52.37 mmol) was added. The reaction mixture was cooled to 0° C. and acryloyl chloride (0.90 g, 9.94 mmol) was added. The mixture stirred at room temperature for 1 h. The reaction was concentrated under vacuum. The residue was purified by silica gel column eluted with EA/hexane (v/v=1/1). This resulted in 1.50 g (23%) of 4-(4-acryloylpiperazin-1-yl)-7-chloro-6-fluoro-1-(2-isopropyl-4-methylpyridin-3-yl)pyrido[2,3-d]pyrimidin-2(1H)-one as yellow solid. LCMS: m z=471 [M+1]⁺.

Step 3. 4-(4-acryloylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 3)

Into a 40-mL sealed tube purged with nitrogen and maintained with an inert atmosphere of nitrogen, was placed 4-(4-acryloylpiperazin-1-yl)-7-chloro-6-fluoro-1-(2-isopropyl-4-methylpyridin-3-yl)pyrido[2,3-d]pyrimidin-2(1H)-one (1.42 g, 3.02 mmol), 2,3,4,5-tetrafluoro-6-(4,4,5,5-tetramethyl-1,3,2-dioxaborolan-2-yl)aniline (3.32 g, 9.68 mmol), Pd(PPh₃)₄ (0.77 g, 0.67 mmol), Na₂CO₃ (1.04 g, 9.81 mmol), dioxane (15 mL) and water (1.5 mL). The reaction mixture was stirred at 80° C. for 1 h. The reaction mixture was filtered and concentrated under vacuum. The reaction mixture was concentrated under vacuum. The residue was purified by Prep-HPLC eluted with CH₃CN/H₂O (v/v=7/3)). This resulted in 535 mg (30% yield) of 4-(4-acryloylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 3) as yellow solid. LCMS: m/z=600 [M+1]⁺.

¹H NMR (400 MHz, CD₃OD) δ 8.50-8.43 (m, 2H), 7.29 (dd, J=5.0, 0.8 Hz, 1H), 6.82 (dd, J=16.8, 10.6 Hz, 1H), 6.30 (dd, J=16.8, 2.0 Hz, 1H), 5.83 (dd, J=10.6, 2.0 Hz, 1H), 4.26-4.09 (m, 4H), 4.03-3.85 (m, 4H), 2.91-2.78 (m, 1H), 2.04 (d, J=3.6 Hz, 3H), 1.19 (d, J=6.8 Hz, 3H), 1.02 (d, J=6.8 Hz, 3H).

Step 4. 4-(4-acryloylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (the first eluting isomer, Compound 3-1) & 4-(4-acryloylpiperazin-1-yl)-7-(2-amino-3,4,5,6-tetrafluorophenyl)-6-fluoro-1-(2-isopropyl-4-methyl pyridin-3-yl)pyrido[2,3-d]pyrimidin-2(1H)-one (the second eluting isomer, Compound 3-2)

The mixture of 4-(4-acryloylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one atropisomers (550 mg) was purified by Chiral-Prep-HPLC with the following conditions: Column: CHIRALPAK IF, 2 cm×25 cm, 5 um; mobile phase: (Hex:DCM(v/v=3:1)):EtOH(v/v=9:1); detected wavelength: UV 220 nm. This resulted in 255 mg (46.36%) of 4-(4-acryloylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (the first eluting isomer, Compound 3-1) as a yellow solid. LCMS: m/z=600 [M+1]⁺.

¹H NMR (400 MHz, CD₃OD) δ 8.50-8.43 (m, 2H), 7.32-7.26 (m, 1H), 6.82 (dd, J=16.8, 10.6 Hz, 1H), 6.30 (dd, J=16.8, 2.0 Hz, 1H), 5.83 (dd, J=10.6, 2.0 Hz, 1H), 4.26-4.09 (m, 4H), 4.03-3.86 (m, 4H), 2.93-2.78 (m, 1H), 2.04 (s, 3H), 1.19 (d, J=6.8 Hz, 3H), 1.02 (d, J=6.8 Hz, 3H).

And 247 mg (44.91%) of 4-(4-acryloylpiperazin-1-yl)-7-(2-amino-3,4,5,6-tetrafluoro phenyl)-6-fluoro-1-(2-isopropyl-4-methylpyridin-3-yl)pyrido[2,3-d]pyrimidin-2(1H)-one (the second eluting isomer, Compound 3-2) as a yellow solid. LCMS: m/z=600 [M+1]⁺.

<sup>1</sup>H NMR (400 MHz, CD<sub>3</sub>OD) δ 8.50-8.43 (m, 2H), 7.29 (dd, J=5.0, 0.8 Hz, 1H), 6.82 (dd, J=16.8, 10.6 Hz, 1H), 6.30 (dd, J=16.7, 1.9 Hz, 1H), 5.83 (dd, J=10.6, 2.0 Hz, 1H), 4.26-4.09 (m, 4H), 4.04-3.85 (m, 4H), 2.94-2.78 (m, 1H), 2.04 (s, 3H), 1.19 (d, J=6.8 Hz, 3H), 1.02 (d, J=6.8 Hz, 3H).

Example 4

4-((R)-4-acryloyl-3-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one ("Compound 4"); (M)-4-((R)-4-acryloyl-3-methylpiperazin-1-yl)-7-(2-amino-3,4,5, 6-tetrafluorophenyl)-6-fluoro-1-(2-isopropyl-4-methylpyridin-3-yl)pyrido[2,3-d]pyrimidin-2(1H)-one; (P)-4-((R)-4-acryloyl-3-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one Compound 4

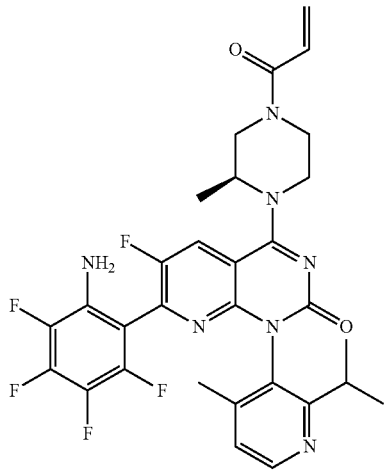

and

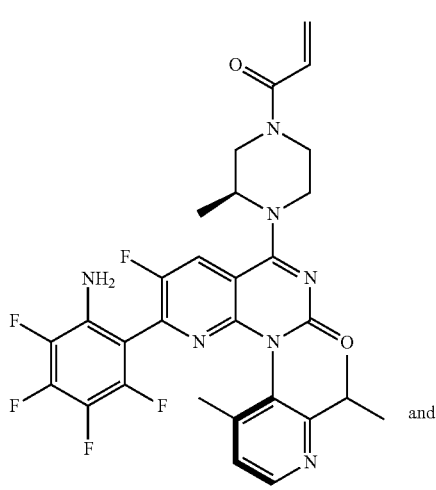

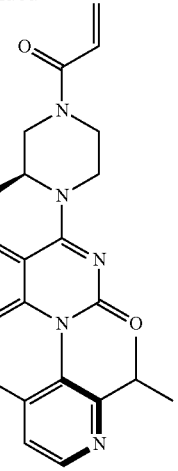

Step 1. 2,2,2-trifluoro-N-(2,3,4,5-tetrafluorophenyl) acetamide

Into a 1000-mL three-neck bottom flask purged with nitrogen and maintained with an inert atmosphere of nitrogen, was placed 2,3,4,5-tetrafluoroaniline (29.64 g, 179.54 mmol), TEA (49.02 g, 484.43 mmol), DCM (300 mL) and stirred. The mixture was cooled to 0° C. and then trifluoroacetic anhydride (61.67 g, 293.62 mmol) was added. The resulting solution was stirred for further 2 h at room temperature. The solution was concentrated under vacuum. The crude was then quenched by the addition of water (500 mL). The resulting solution was extracted with EA (3×200 mL). The organic layers were combined, then washed with sodium bicarbonate solution (200 mL) and brine (300 mL), dried over anhydrous Na<sub>2</sub>SO<sub>4</sub>. the residue was concentrated under vacuum. This resulted in 53.45 g (crude) of 2,2,2-trifluoro-N-(2,3,4,5-tetrafluoro phenyl)acetamide. LCMS: m z=260 [M-H]<sup>−</sup>.

Step 2. (2-amino-3,4,5,6-tetrafluorophenyl)boronic acid

Into a 1000-mL round-bottom flask purged with nitrogen and maintained with an inert atmosphere of nitrogen, was placed 2,2,2-trifluoro-N-(2,3,4,5-tetrafluorophenyl)acetamide (25.03 g, 95.90 mmol) and THF (250 mL). The mixture was cooled to −65° C. and then n-butyl lithium solution (88 mL, 223.46 mmol) was added. The mixture was stirred at −50° C. for 1 h. Then trimethyl borate (30.24 g, 290.95 mmol) was added dropwise at −70° C. The mixture was stirred at room temperature for 1 h. The reaction was then quenched by the addition of 4N HCl solution (200 mL). The mixture was stirred at room temperature for 0.5 h. The resulting solution was extracted with EA (2×200 mL). The organic layers were combined, then washed with sodium bicarbonate solution (200 mL) and brine (200 mL), dried over anhydrous Na<sub>2</sub>SO<sub>4</sub>. The residue was concentrated under vacuum. The crude was stirred with the mixture of Hex/EA (v/v=20/1)(70 mL) for 1 h. The resulting solid was filtered to provide 5.10 g (25.50% yield) of (2-amino-3,4, 5,6-tetrafluorophenyl)boronic acid as off-white solid. LCMS: m z=210 [M+1]<sup>+</sup>.

Step 3. 2,3,4,5-tetrafluoro-6-((3aR,4R,6R)-3a,5,5-trimethylhexahydro-4,6-methanobenzo[d][1,3,2]dioxaborol-2-yl)aniline Into a 250-mL round-bottom flask was placed (2-amino-3,4,5,6-tetrafluorophenyl) boronic acid (11.82 g, 56.58 mmol), (1S,3R,4S,5S)-4,6,6-trimethylbicyclo[3.1.1]heptane-3,4-diol (9.56 g, 56.58 mmol) and toluene (120 mL). The mixture was stirred for 3 h at 55° C. The residue was concentrated under vacuum and purified by a silica gel column eluted with Hex/EA (v/v=20/1). This resulted 17.08 g (87.98% yield) of 2,3,4,5-tetrafluoro-6-((3aR,4R,6R)-3a,5,5-trimethylhexahydro-4,6-methanobenzo[d][1,3,2]dioxaborol-2-yl)aniline as brown solid. LCMS: m z=344 [M+1]$^+$.

Step 4. tert-butyl (R)-4-(7-chloro-6-fluoro-1-(2-isopropyl-4-methylpyridin-3-yl)-2-oxo-1,2-dihydropyrido[2,3-d]pyrimidin-4-yl)-2-methylpiperazine-1-carboxylate Into a 50-mL round-bottom flask purged with nitrogen and maintained with an inert atmosphere of nitrogen, was placed 7-chloro-6-fluoro-1-(2-isopropyl-4-methylpyridin-3-yl)pyrido[2,3-d]pyrimidine-2,4(1H,3H)-dione (7.24 g, 0.02 mol), POCl$_3$ (7.95 g, 0.05 mol), DIEA (12.12 g, 0.12 mol) and acetonitrile (30 mL). The mixture was stirred at 80° C. for 2 h. The reaction was cooled to room temperature and concentrated under vacuum. This resulted in 4,7-dichloro-6-fluoro-1-(2-isopropyl-4-methylpyridin-3-yl) pyrido[2,3-d]pyrimidin-2(1H)-one which was used directly in next step.

Into a 100-mL round-bottom flask purged with nitrogen and maintained with an inert atmosphere of nitrogen, was placed 4,7-dichloro-6-fluoro-1-(2-isopropyl-4-methylpyridin-3-yl)pyrido[2,3-d]pyrimidin-2(1H)-one (crude) and acetonitrile (80 mL), followed by the addition of DIEA (12.12 g, 0.12 mol) and tert-butyl (R)-2-methylpiperazine-1-carboxylate (4.01 g, 0.02 mol). The reaction mixture was stirred for 0.5 h at room temperature. The reaction was then quenched by the addition of water (300 mL). The resulting solution was extracted with ethyl acetate (2×300 mL). The organic layers were combined and washed with brine (50 mL), dried over anhydrous Na$_2$SO$_4$, filtered and concentrated under vacuum. The residue was purified by silica gel column eluted with EA/hexane (v:v=9/1). This resulted in 3.208 g (30% in two steps) of tert-butyl (R)-4-(7-chloro-6-fluoro-1-(2-isopropyl-4-methylpyridin-3-yl)-2-oxo-1,2-dihydropyrido[2,3-d]pyrimidin-4-yl)-2-methylpiperazine-1-carboxylate as yellow solid. LCMS: m z=531 [M+1]$^+$.

Step 5. (R)-4-(4-acryloyl-3-methylpiperazin-1-yl)-7-chloro-6-fluoro-1-(2-isopropyl-4-methyl pyridin-3-yl)pyrido[2,3-d]pyrimidin-2(1H)-one Into a 50-mL round-bottom flask purged with nitrogen and maintained with an inert atmosphere of nitrogen, was placed tert-butyl (R)-4-(7-chloro-6-fluoro-1-(2-isopropyl-4-methylpyridin-3-yl)-2-oxo-1,2-dihydropyrido[2,3-d]pyrimidin-4-yl)-2-methylpiperazine-1-carboxylate (3.208 g, 6.04 mol), TFA (25 ml) and DCM (75 mL). The reaction mixture was stirred for 1 h at room temperature and concentrated under vacuum. This resulted in (R)-7-chloro-6-fluoro-1-(2-isopropyl-4-methylpyridin-3-yl)-4-(3-methyl piperazin-1-yl)pyrido[2,3-d]pyrimidin-2(1H)-one as crude, which was used directly in the next step.

Into a 50-mL round-bottom flask and maintained with an inert atmosphere of nitrogen, was placed (R)-7-chloro-6-fluoro-1-(2-isopropyl-4-methylpyridin-3-yl)-4-(3-methylpiperazin-1-yl)pyrido[2,3-d]pyrimidin-2(1H)-one (crude), ACN (75 mL), DIEA (1.45 g, 12.08 mmol) and acryloyl chloride (0.549 g, 6.06 mmol). The reaction mixture was stirred at room temperature for 0.5 h. The reaction was then quenched by the addition of water (100 mL), extracted with ethyl acetate (3×200 mL). The organic layers were combined and washed with brine (100 mL), dried over anhydrous Na$_2$SO$_4$, filtered and concentrated under vacuum. The residue was purified by silica gel column eluted with EA/hexane (v:v=4/1). This resulted in 2.38 g (82% in two steps) of (R)-4-(4-acryloyl-3-methylpiperazin-1-yl)-7-chloro-6-fluoro-1-(2-isopropyl-4-methylpyridin-3-yl)pyrido[2,3-d]pyrimidin-2(1H)-one as yellow solid. LCMS: m z=485[M+1]$^+$.

Step 6. 4-((R)-4-acryloyl-3-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 4)

Into a 20-mL sealed tube purged with nitrogen and maintained with an inert atmosphere of nitrogen, was placed (R)-4-(4-acryloyl-3-methylpiperazin-1-yl)-7-chloro-6-fluoro-1-(2-isopropyl-4-methylpyridin-3-yl) pyrido[2,3-d]pyrimidin-2(1H)-one (1.224 g, 2.52 mmol), 2,3,4,5-tetrafluoro-6-((3aR,4R,6R)-3a,5,5-trimethylhexahydro-4,6-methanobenzo[d][1,3,2]dioxaborol-2-yl)aniline (1.794 g, 5.223 mmol), Pd(PPh$_3$)$_4$ (0.614 g, 0.53 mmol), Na$_2$CO$_3$ (0.72 g, 6.79 mmol), dioxane (12 mL) and water (1 mL). The reaction mixture was stirred at 80° C. for 2 h. The reaction mixture was filtered and concentrated under vacuum. The residue was purified by Prep-HPLC eluted with ACN/H$_2$O (1% NH$_4$HCO$_3$) (v:v=7/3). This resulted in 740 mg (47.8% in two steps) of 4-((R)-4-acryloyl-3-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 4) as yellow solid. LCMS: m z=614 [M+1]$^+$.

$^1$H NMR (400 MHz, CD$_3$OD) δ 8.52-8.43 (m, 2H), 7.29 (d, J=5.0 Hz, 1H), 6.81 (dd, J=16.8, 10.6 Hz, 1H), 6.29 (d, J=16.5 Hz, 1H), 5.81 (d, J=10.4 Hz, 1H), 4.58-4.26 (m, 3H), 4.11-3.72 (m, 4H), 2.81-2.83 (m, 1H), 2.05 (d, J=18.6 Hz, 3H), 1.39 (s, 3H), 1.18 (d, J=6.8 Hz, 3H), 1.01-1.02 (m, 3H).

Step 7. 4-((R)-4-acryloyl-3-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (the first eluting isomer, Compound 4-1) & 4-((R)-4-acryloyl-3-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (the second eluting isomer, Compound 4-2)

The mixture of 4-((R)-4-acryloyl-3-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2

(1H)-one atropisomers (710 mg) was purified by Chiral-Prep-HPLC with the following conditions: Column: CHIRAL ART Amylose-SA, 3 cm×25 cm, 5 um; mobile phase: CO$_2$: IPA(v/v=62:38); detected wavelength: UV 220 nm. This resulted in 223 mg (40.58%) of 4-((R)-4-acryloyl-3-methylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (the first eluting isomer, Compound 4-1) as a yellow solid. LCMS: m z=614 [M+1]$^+$.

$^1$H NMR (400 MHz, CD$_3$OD) δ 8.46 (dd, J=7.3, 5.0 Hz, 2H), 7.34-7.21 (m, 1H), 6.81 (dd, J=16.7, 10.6 Hz, 1H), 6.29 (d, J=16.7 Hz, 1H), 5.81 (d, J=11.0 Hz, 1H), 4.58-4.32 (m, 3H), 3.98-3.77 (m, 4H), 2.75-2.77 (m, 1H), 2.07 (s, 3H), 1.50-1.30 (m, 3H), 1.18 (d, J=6.8 Hz, 3H), 1.00 (d, J=6.8 Hz, 3H).

And 236 mg (38.84%) of 4-((R)-4-acryloyl-3-methylpiperazin-1-yl)-7-(2-amino-3,4,5,6-tetrafluoro phenyl)-6-fluoro-1-(2-isopropyl-4-methylpyridin-3-yl)pyrido[2,3-d]pyrimidin-2(1H)-one (the second eluting isomer, Compound 4-2) as a yellow solid. LCMS: m z=614 [M+1]$^+$.

$^1$H NMR (400 MHz, CD$_3$OD) δ 8.50 (d, J=8.9 Hz, 1H), 8.40 (d, J=5.0 Hz, 1H), 7.24 (d, J=4.5 Hz, 1H), 6.81 (dd, J=16.9, 10.4 Hz, 1H), 6.29 (d, J=16.9 Hz, 1H), 5.81 (d, J=10.5 Hz, 1H), 4.40-4.42 (m, 3H), 4.08-3.80 (m, 4H), 2.87-2.69 (m, 1H), 2.02 (s, 3H), 1.48-1.32 (m, 3H), 1.20-1.16 (m, 3H), 1.00 (d, J=6.8 Hz, 3H).

Example 5

4-((3S,5R)-4-acryloyl-3,5-dimethylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 5); (M)-4-((3S,5R)-4-acryloyl-3,5-dimethylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one; and (P)-4-((3S,5R)-4-acryloyl-3,5-dimethylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one Compound 5

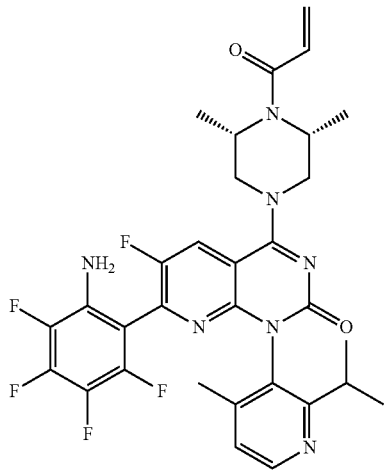

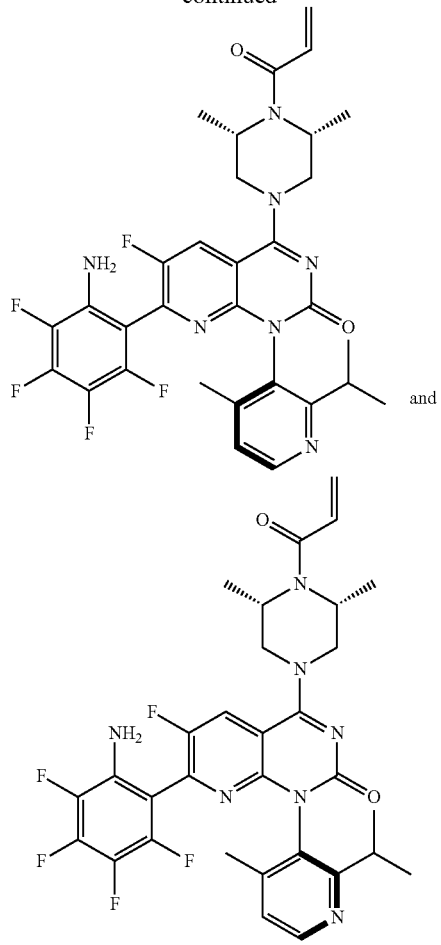

and

Step 1. 4-((3S,5R)-4-acryloyl-3,5-dimethylpiperazin-1-yl)-7-chloro-6-fluoro-1-(2-isopropyl-4-methyl pyridin-3-yl)pyrido[2,3-d]pyrimidin-2(1H)-one Into a 250-mL round-bottom flask purged with nitrogen and maintained with an inert atmosphere of nitrogen, was placed 7-chloro-6-fluoro-4-hydroxy-1-(2-isopropyl-4-methylpyridin-3-yl)pyrido[2,3-d]pyrimidin-2(1H)-one (7.75 g, 22.22 mmol), POCl$_3$ (8.75 g, 57.08 mmol), DIEA (10.00 g, 77.35 mmol) and acetonitrile (80 mL). The mixture was stirred at 80° C. for 1 h. The reaction was cooled to room temperature and concentrated under vacuum. Into a 250-mL round-bottom flask purged with nitrogen and maintained with an inert atmosphere of nitrogen, was placed 4,7-dichloro-6-fluoro-1-(2-isopropyl-4-methylpyridin-3-yl)pyrido[2,3-d]pyrimidin-2(1H)-one (8.17 g, 22.22 mmol) and acetonitrile (80 mL). DIEA (3.24 g, 25.09 mmol) and (2R,6S)-2,6-dimethylpiperazine (2.36 g, 20.69 mmol) were added. The reaction mixture was stirred for 0.5 h at room temperature. The reaction mixture was cooled to 0° C. and acryloyl chloride (1.65 g, 18.21 mmol) was added. The reaction was then quenched by the addition of water (50 mL). The resulting solution was extracted with ethyl acetate (3×150 mL). The organic layers were combined and washed with brine (50 mL), dried over anhydrous Na$_2$SO$_4$, filtered and concentrated under vacuum. The residues was purified by silica gel column eluted with MeOH/EA (v/v=1/10). This resulted in 3.70 g (33% in two steps) of 4-((3S,5R)-4- acryloyl-3,5-dimethylpiperazin-1-yl)-7-chloro-6-fluoro-1-(2-isopropyl-4-methylpyridin-3-yl)pyrido[2,3-d]pyrimidin-2(1H)-one as yellow oil. LCMS: m z=499 [M+1]+.

Step 2. 4-((3S,5R)-4-acryloyl-3,5-dimethylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 5)

Into a 20-mL round-bottom flask was placed 4-((3S,5R)-4-acryloyl-3,5-dimethylpiperazin-1-yl)-7-chloro-6-fluoro-1-(2-isopropyl-4-methylpyridin-3-yl)pyrido[2,3-d]pyrimidin-2(1H)-one (0.295 g, 0.59 mmol), (2-amino-3,4,5,6-tetrafluorophenyl)boronic acid (0.348 g, 1.67 mmol), Pd(PPh$_3$)$_4$ (0.140 g, 0.12 mmol), Na$_2$CO$_3$ (0.214 g, 2.02 mmol), dioxane (5 mL) and water (1 mL). The reaction mixture was stirred at 80° C. for 1 h. The reaction mixture was filtered and concentrated under vacuum. The residue was purified by Prep-HPLC eluted with CH$_3$CN/H$_2$O (0.05% NH$_4$HCO$_3$) (v:v=2/1). This resulted in 0.111 g (30%) of 4-((3S,5R)-4-acryloyl-3,5-dimethylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (Compound 5) as yellow solid. LCMS: m z=628 [M+1]+.

$^1$H NMR (400 MHz, CD$_3$OD) δ 8.39-8.32 (m, 2H), 7.21 (d, J=5.0 Hz, 1H), 6.77-6.70 (m, 1H), 6.24-6.18 (m, 1H), 5.78-5.69 (m, 1H), 4.60 (s, 2H), 4.46-4.35 (m, 2H), 3.77-3.67 (m, 2H), 2.74-2.66 (m, 1H), 1.97 (s, 3H), 1.43 (d, J=6.9 Hz, 3H), 1.37 (d, J=7.0 Hz, 3H), 1.09 (d, J=6.8 Hz, 3H), 0.93 (d, J=6.8 Hz, 3H).

Step 3. 4-((3S,5R)-4-acryloyl-3,5-dimethylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (the first eluting isomer, Compound 5-1) & 4-((3S,5R)-4-acryloyl-3,5-dimethylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (the second eluting isomer, Compound 5-2)

The mixture of 4-((3S,5R)-4-acryloyl-3,5-dimethylpiperazin-1-yl)-7-(2-amino-3,4,5,6-tetrafluoro phenyl)-6-fluoro-1-(2-isopropyl-4-methylpyridin-3-yl)pyrido[2,3-d]pyrimidin-2(1H)-one atropisomers (408 mg) was purified by Chiral-Prep-HPLC with the following conditions: Column: CHIRALPAK IG, 3 cm×25 cm, 5 um; mobile phase: (Hex:DCM=3:1(v/v)):EtOH(v/v=92:8); detected wavelength: UV 220 nm. This resulted in 148 mg (36.27%) of 4-((3S,5R)-4-acryloyl-3,5-dimethylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (the first eluting isomer, Compound 5-1) as a yellow solid. LCMS: m z=628 [M+1]+.

$^1$H NMR (400 MHz, CD$_3$OD) δ 8.39-8.31 (m, 2H), 7.20 (d, J=5.0 Hz, 1H), 6.79-6.68 (m, 1H), 6.24-6.16 (m, 1H), 5.75-5.68 (m, 1H), 4.56 (d, J=40.4 Hz, 2H), 4.48-4.26 (m, 2H), 3.89-3.61 (m, 2H), 2.76-2.64 (m, 1H), 1.96 (s, 3H), 1.54-1.28 (m, 6H), 1.09 (d, J=6.8 Hz, 3H), 0.97-0.81 (m, 3H).

And 159 mg (38.97%) of 4-((3S,5R)-4-acryloyl-3,5-dimethylpiperazin-1-yl)-7-(2-amino-3,4,5,6-tetrafluorophenyl)-6-fluoro-1-(2-isopropyl-4-methylpyridin-3-yl)pyrido[2,3-d]pyrimidin-2(1H)-one (the second eluting isomer, Compound 5-2) as a yellow solid. LCMS: m z=628 [M+1]+.

$^1$H NMR (400 MHz, CD$_3$OD) δ 8.40-8.30 (m, 2H), 7.20 (d, J=5.0 Hz, 1H), 6.78-6.67 (m, 1H), 6.25-6.16 (m, 1H), 5.78-5.67 (m, 1H), 4.56 (d, J=38.1 Hz, 2H), 4.51-4.33 (m, 2H), 3.83-3.66 (m, 2H), 2.78-2.70 (m, 1H), 1.96 (s, 3H), 1.48-1.38 (m, 3H), 1.36 (d, J=6.9 Hz, 3H), 1.09 (d, J=6.8 Hz, 3H), 0.92 (d, J=6.8 Hz, 3H).

Example 6

4-((R)-4-acryloyl-3-methylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (Compound 6)

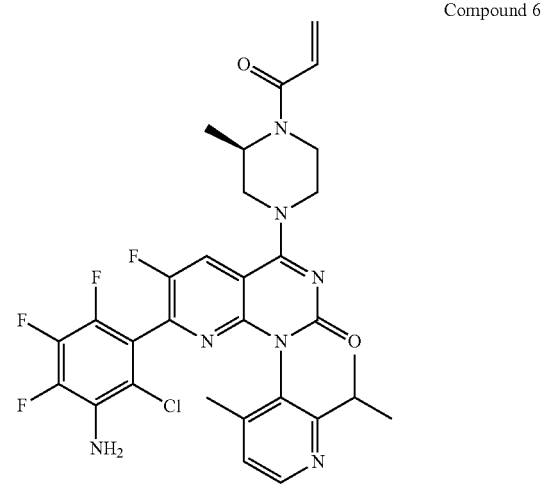 [SMILES: C=CC(=O)N1CCN(c2nc(=O)n(-c3c(C)ccnc3C(C)C)c3nc(-c4c(F)c(F)c(F)c(N)c4Cl)c(F)cc23)C[C@H]1C]

Compound 6

Step 1. (R)-4-(4-acryloyl-3-methylpiperazin-1-yl)-7-(5-amino-2,3,4-trifluorophenyl)-6-fluoro-1-(2-isopropyl-4-methylpyridin-3-yl)pyrido[2,3-d]pyrimidin-2(1H)-one Into a 20-mL sealed tube purged with nitrogen and maintained with an inert atmosphere of nitrogen, was placed (R)-4-(4-acryloyl-3-methylpiperazin-1-yl)-7-chloro-6-fluoro-1-(2-isopropyl-4-methylpyridin-3-yl)pyrido[2,3-d]pyrimidin-2(1H)-one (1.02 g, 2.47 mmol), (5-amino-2,3,4-trifluorophenyl)boronic acid (0.94 g, 4.92 mmol), Pd(PPh$_3$)$_4$ (0.59 g, 0.51 mmol), Na$_2$CO$_3$ (0.738 g, 6.96 mmol), dioxane (30 mL) and water (2 mL). The reaction mixture was stirred at 80° C. for 4 h. The reaction mixture was filtered and concentrated under vacuum. The residue was purified by silica gel column eluted with ACN/H$_2$O (v/v=7/3). This resulted in 200 mg (crude) of (R)-4-(4-acryloyl-3-methylpiperazin-1-yl)-7-(5-amino-2,3,4-trifluorophenyl)-6-fluoro-1-(2-isopropyl-4-methylpyridin-3-yl)pyrido[2,3-d]pyrimidin-2(1H)-one as yellow solid. LCMS: m z=596 [M+1]+.

Step 2. 4-((R)-4-acryloyl-3-methylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (Compound 6)

Into a 50-mL round-bottom flask purged with nitrogen and maintained with an inert atmosphere of nitrogen, was placed (R)-4-(4-acryloyl-3-methylpiperazin-1-yl)-7-(5- amino-2,3,4-trifluorophenyl)-6-fluoro-1-(2-isopropyl-4-methylpyridin-3-yl)pyrido[2,3-d]pyrimidin-2(1H)-one (200 mg, 0.34 mmol), NCS (111 mg, 0.83 mmol) and AcOH (3 mL). The reaction mixture was stirred for 48 h at room temperature. The reaction was then quenched by the addition of water (100 mL). The resulting solution was extracted with ethyl acetate (2×100 mL). The organic layers were combined and washed with brine (10 mL), dried over anhydrous Na$_2$SO$_4$, filtered and concentrated under vacuum. The residues was purified by Prep-HPLC eluted with ACN/H$_2$O (0.5% NH$_4$HCO$_3$) (v/v=7/3)). This resulted in 17 mg of 4-((R)-4-acryloyl-3-methylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (Compound 6) as yellow solid. LCMS: m z=630[M+1]$^+$.

$^1$H NMR (400 MHz, CD$_3$OD) δ 8.50 (d, J=8.9 Hz, 1H), 8.40 (d, J=5.0 Hz, 1H), 7.24 (d, J=4.5 Hz, 1H), 6.81 (dd, J=16.9, 10.4 Hz, 1H), 6.29 (d, J=16.9 Hz, 1H), 5.81 (d, J=10.5 Hz, 1H), 4.40-4.41 (m, 3H), 4.15-3.55 (m, 4H), 2.87-2.69 (m, 1H), 2.07-1.94 (m, 3H), 1.49-1.33 (m, 3H), 1.20-1.16 (m, 3H), 1.01-1.03 (m, 3H).

Example 7

4-((3S,5R)-4-acryloyl-3,5-dimethylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (Compound 7); (M)-4-((3S,5R)-4-acryloyl-3,5-dimethylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one; and (P)-4-((3S,5R)-4-acryloyl-3,5-dimethylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one Compound 7

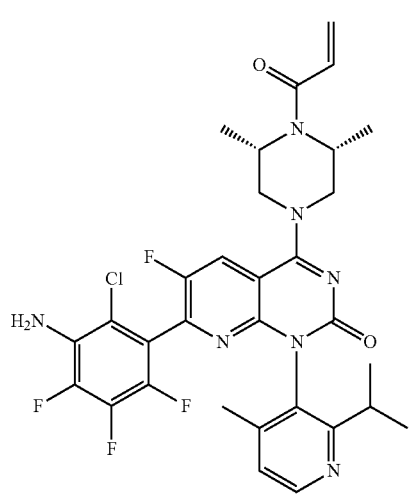

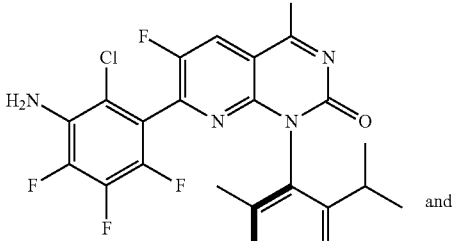

and

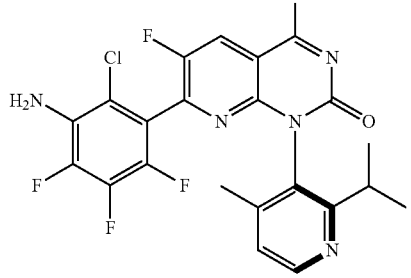

Step 1. 4-((3S,5R)-4-acryloyl-3,5-dimethylpiperazin-1-yl)-7-(5-amino-2,3,4-trifluorophenyl)-6-fluoro-1-(2-isopropyl-4-methylpyridin-3-yl)pyrido[2,3-d]pyrimidin-2(1H)-one Into a 20-mL round-bottom flask was placed 4-((3S,5R)-4-acryloyl-3,5-dimethylpiperazin-1-yl)-7-chloro-6-fluoro-1-(2-isopropyl-4-methylpyridin-3-yl)pyrido[2,3-d]pyrimidin-2(1H)-one (2.50 g, 5.01 mmol), (5-amino-2,3,4-trifluorophenyl)boronic acid (3.08 g, 16.15 mmol), Pd(PPh$_3$)$_4$ (0.45 g, 0.39 mmol), Na$_2$CO$_3$ (0.98 g, 9.21 mmol), dioxane (20 mL) and water (4 mL). The reaction mixture was stirred at 80° C. for 1 h. The reaction mixture was filtered and concentrated under vacuum. The residue was purified by C$_{18}$ column eluted with CH$_3$CN/H$_2$O (v/v=2/1). This resulted in 0.476 g of 4-((3S,5R)-4-acryloyl-3,5-dimethylpiperazin-1-yl)-7-(5-amino-2,3,4-trifluorophenyl)-6-fluoro-1-(2-isopropyl-4-methylpyridin-3-yl)pyrido[2,3-d]pyrimidin-2(1H)-one as yellow solid. LCMS: m z=610 [M+1]$^+$.

Step 2. 4-((3S,5R)-4-acryloyl-3,5-dimethylpiperazin-1-yl)-7-(3-amino-2-chloro-4,5,6-trifluoro phenyl)-6-fluoro-1-(2-isopropyl-4-methylpyridin-3-yl)pyrido[2,3-d]pyrimidin-2(1H)-one Into a 20-mL round-bottom flask was placed 4-((3S,5R)-4-acryloyl-3,5-dimethylpiperazin-1-yl)-7-(5-amino-2,3,4- trifluorophenyl)-6-fluoro-1-(2-isopropyl-4-methylpyridin-3-yl)pyrido[2,3-d]pyrimidin-2(1H)-one (0.476 g, 0.78 mmol), NCS (0.212 g, 1.59 mmol) and HOAc (5 mL). The reaction mixture was stirred at room temperature for 1 day. The reaction mixture was filtered and concentrated under vacuum.

The residue was purified by $C_{18}$ eluted with $CH_3CN/H_2O$ (0.05% $NH_4HCO_3$) (v/v=1/1). This resulted in 181 mg (37%) of 4-((3S,5R)-4-acryloyl-3,5-dimethylpiperazin-1-yl)-7-(3-amino-2-chloro-4,5,6-trifluoro phenyl)-6-fluoro-1-(2-isopropyl-4-methylpyridin-3-yl)pyrido[2,3-d]pyrimidin-2(1H)-one as off-white solid. LCMS: m z=644 [M+1]$^+$.

$^1$H NMR (400 MHz, CD$_3$OD) δ 8.47 (d, J=8.9 Hz, 1H), 8.40 (d, J=5.0 Hz, 1H), 7.27-7.22 (m, 1H), 6.92-6.77 (m, 1H), 6.37-6.22 (m, 1H), 5.84-5.75 (m, 1H), 4.70 (s, 2H), 4.60-4.40 (m, 2H), 3.91-3.71 (m, 2H), 2.87-2.74 (m, 1H), 2.11-1.99 (m, 3H), 1.60-1.37 (m, 6H), 1.18 (d, J=6.8 Hz, 3H), 1.04-0.93 (m, 3H).

Step 3. 4-((3S,5R)-4-acryloyl-3,5-dimethylpiperazin-1-yl)-7-(3-amino-2-chloro-4,5,6-trifluoro phenyl)-6-fluoro-1-(2-isopropyl-4-methylpyridin-3-yl)pyrido[2,3-d]pyrimidin-2(1H)-one (the first eluting, Compound 7-1) & 4-((3S,5R)-4-acryloyl-3,5-dimethylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (the second eluting isomer, Compound 7-2)

The mixture of 4-((3S,5R)-4-acryloyl-3,5-dimethylpiperazin-1-yl)-7-(3-amino-2-chloro-4,5,6-trifluoro phenyl)-6-fluoro-1-(2-isopropyl-4-methylpyridin-3-yl)pyrido[2,3-d]pyrimidin-2(1H)-one atropisomers (180 mg) was purified by Chiral-Prep-HPLC with the following conditions: Column: CHIRALPAK IF, 2 cm×25 cm, 5 um; mobile phase: (Hex:DCM(v/v=3:1)):IPA(v/v=90:10); detected wavelength: UV 220 nm. This resulted in 81 mg (45%) of 4-((3S,5R)-4-acryloyl-3,5-dimethylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (the first eluting isomer, Compound 7-1) as off-white solid. LCMS: m z=644 [M+1]$^+$.

$^1$H NMR (400 MHz, CD$_3$OD) δ 8.47 (d, J=8.9 Hz, 1H), 8.40 (d, J=5.0 Hz, 1H), 7.31-7.20 (m, 1H), 6.86-6.77 (m, 1H), 6.34-6.25 (m, 1H), 5.87-5.76 (m, 1H), 4.81-4.62 (m, 2H), 4.62-4.39 (m, 2H), 3.92-3.75 (m, 2H), 2.85-2.72 (m, 1H), 2.03 (d, J=10.7 Hz, 3H), 1.56-1.39 (m, 6H), 1.18 (d, J=6.8 Hz, 3H), 1.04-0.95 (m, 3H).

And 79 mg (43.89%) of 4-((3S,5R)-4-acryloyl-3,5-dimethylpiperazin-1-yl)-7-(3-amino-2-chloro-4,5,6-trifluorophenyl)-6-fluoro-1-(2-isopropyl-4-methylpyridin-3-yl)pyrido[2,3-d]pyrimidin-2(1H)-one (the second eluting isomer, Compound 7-2) as off-white solid. LCMS: m z=644 [M+1]$^+$.

$^1$H NMR (400 MHz, CD$_3$OD) δ 8.47 (d, J=8.9 Hz, 1H), 8.40 (d, J=5.0 Hz, 1H), 7.32-7.18 (m, 1H), 6.86-6.75 (m, 1H), 6.32-6.22 (m, 1H), 5.86-5.75 (m, 1H), 4.70 (s, 2H), 4.60-4.38 (m, 2H), 3.87-3.76 (m, 2H), 2.86-2.71 (m, 1H), 2.03 (d, J=10.7 Hz, 3H), 1.60-1.42 (m, 6H), 1.18 (d, J=6.8 Hz, 3H), 1.07-0.92 (m, 3H).

The following compound can be synthesized:

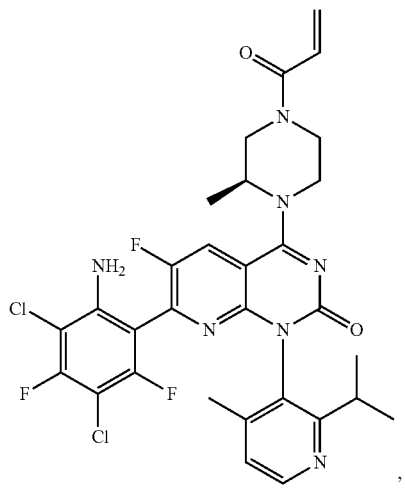
,

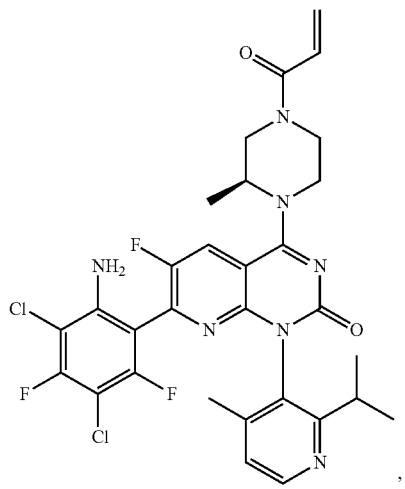
,

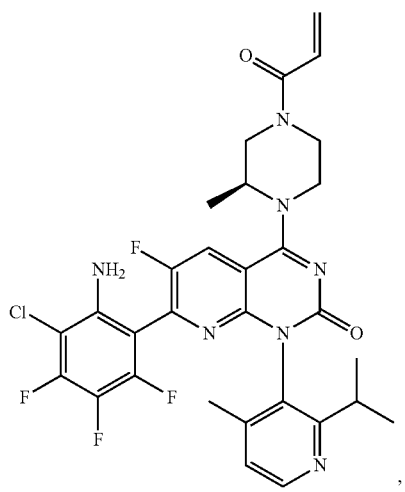
,

109
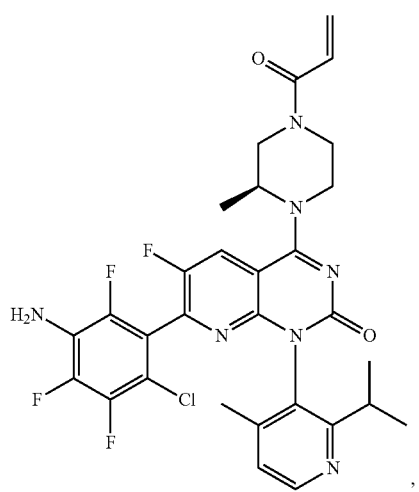
,
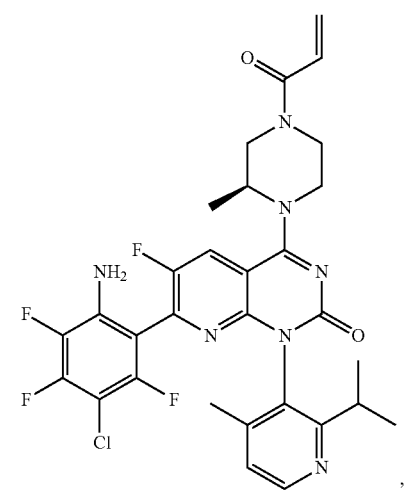
,
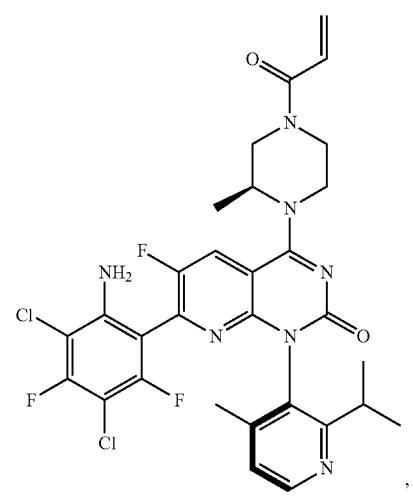
,
110
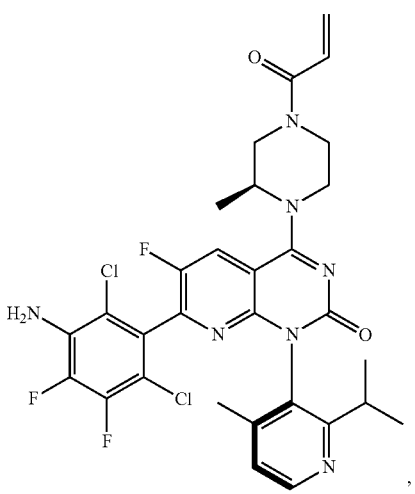
,
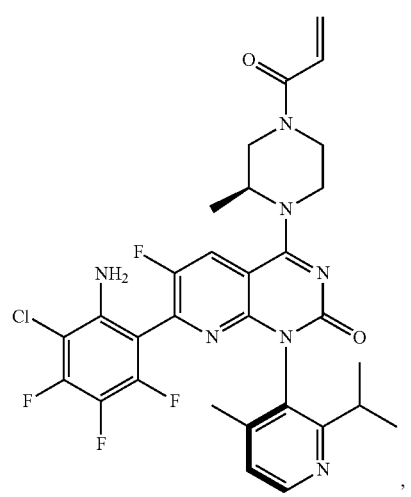
,
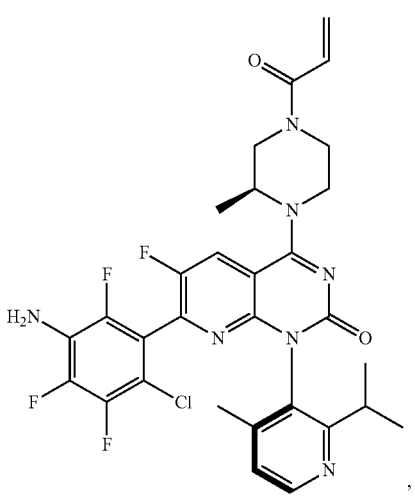
, 111
-continued
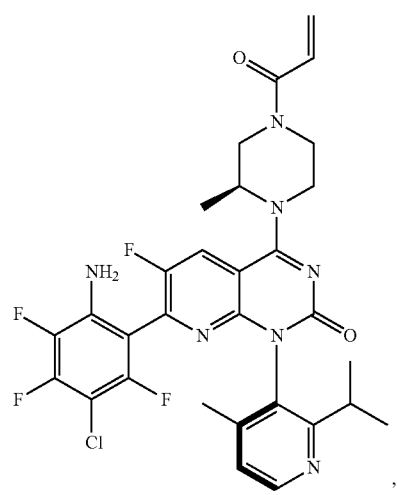
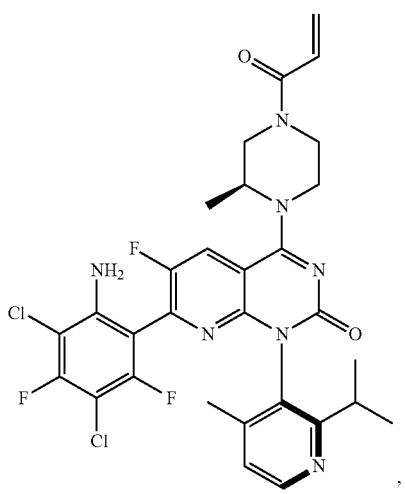
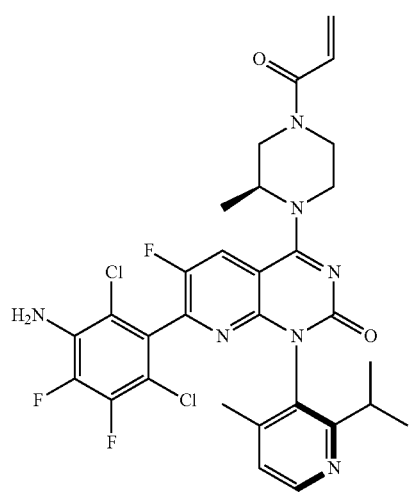
112
-continued
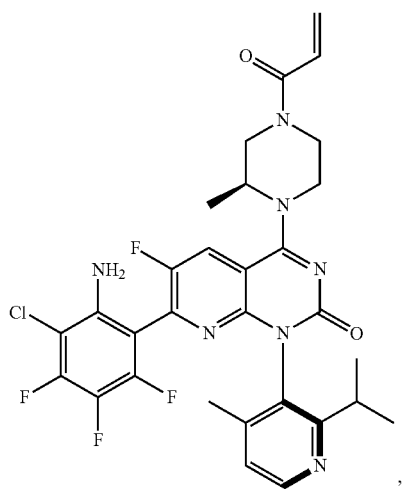
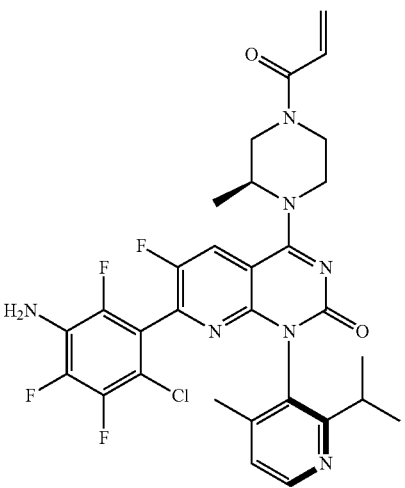
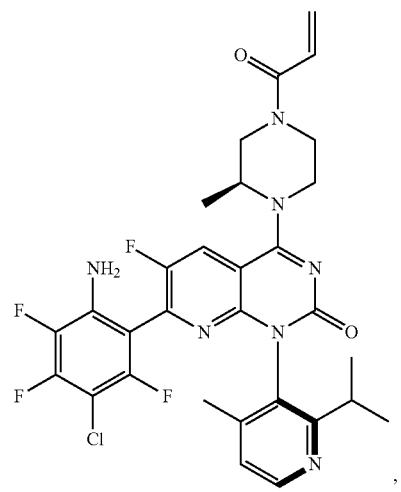

113
-continued
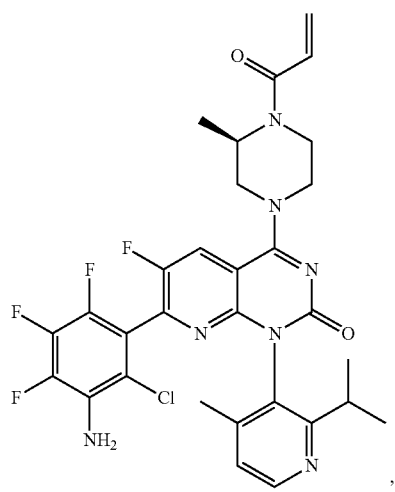
,
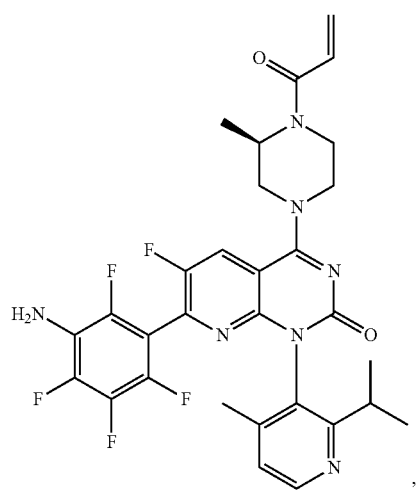
,
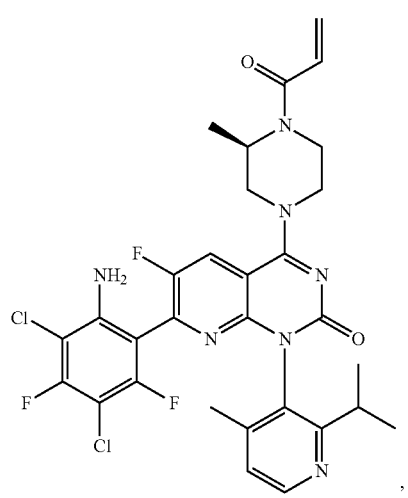
,
114
-continued
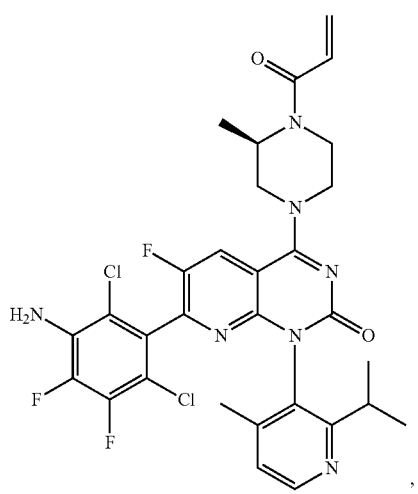
,
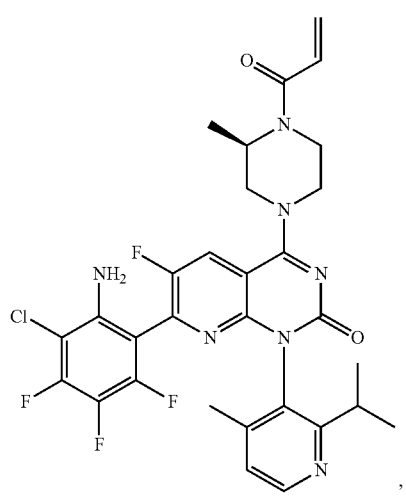
,
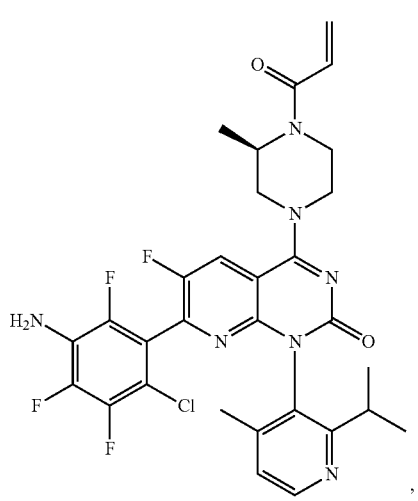
, 115
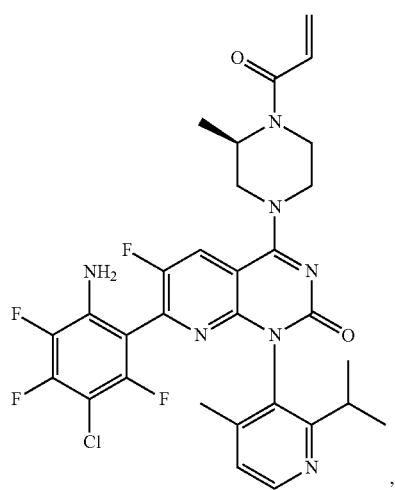
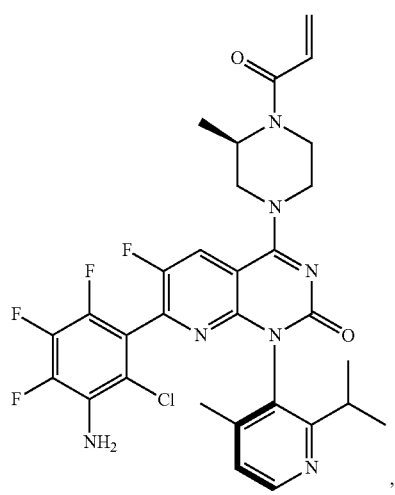
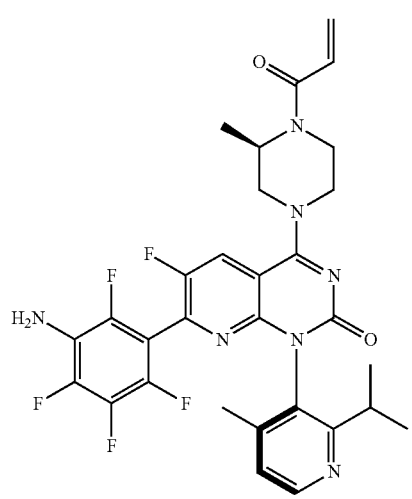
116
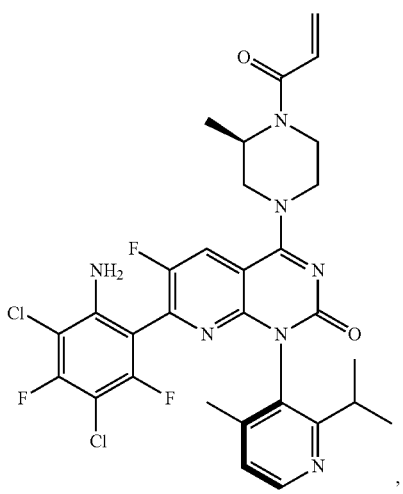
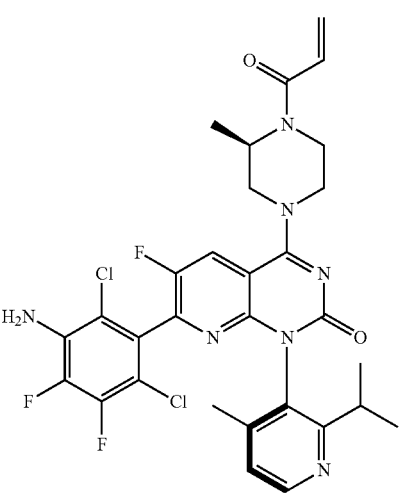
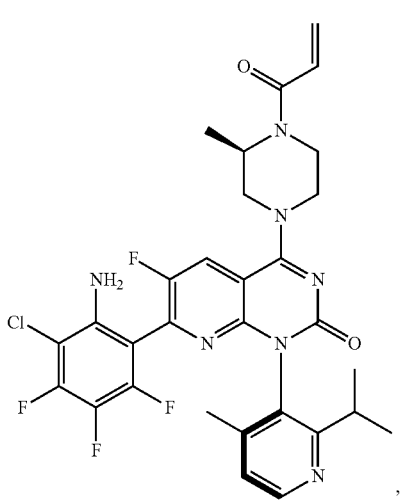

117
-continued
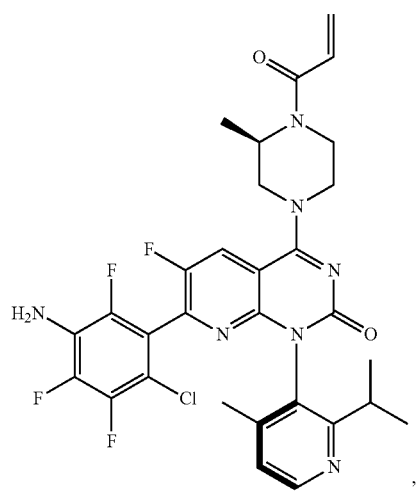
,
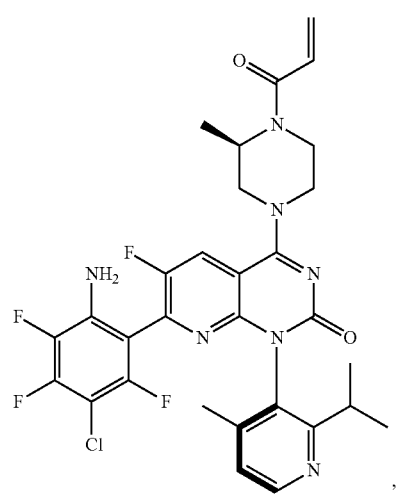
,
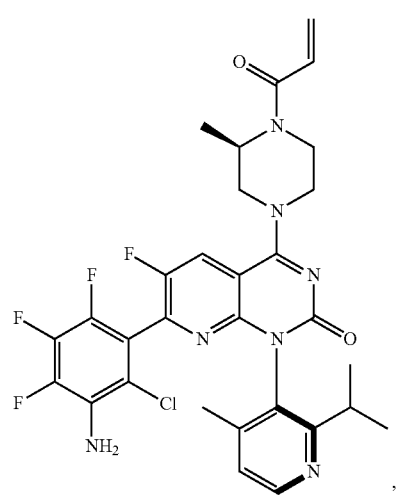
,
118
-continued
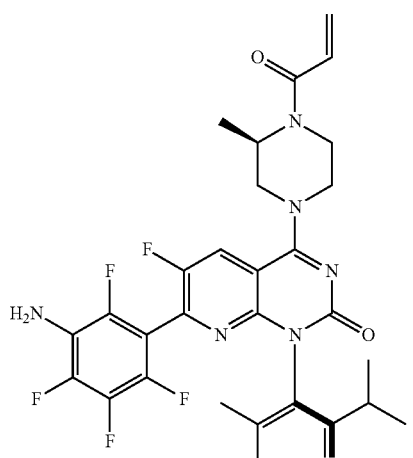
,
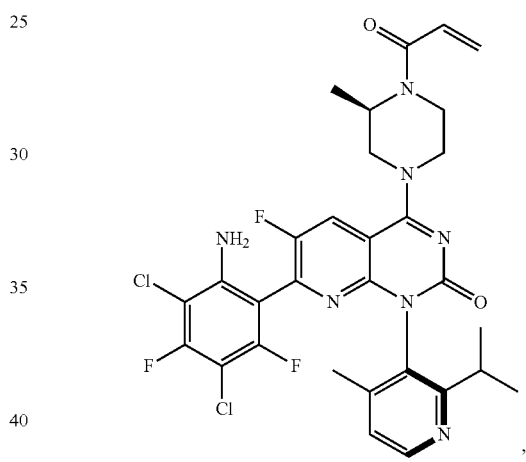
,
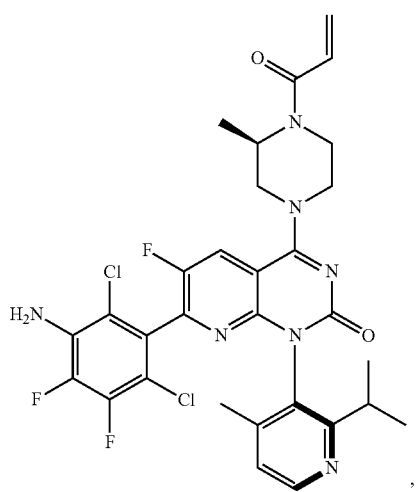
, 119
-continued
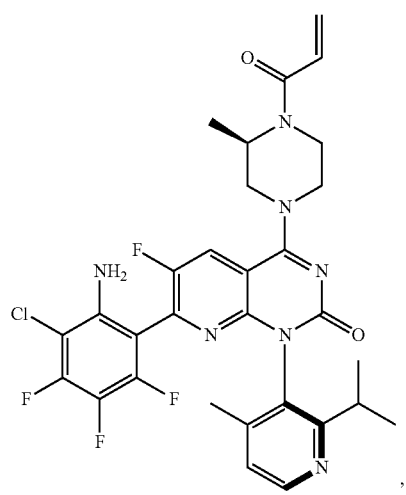
,
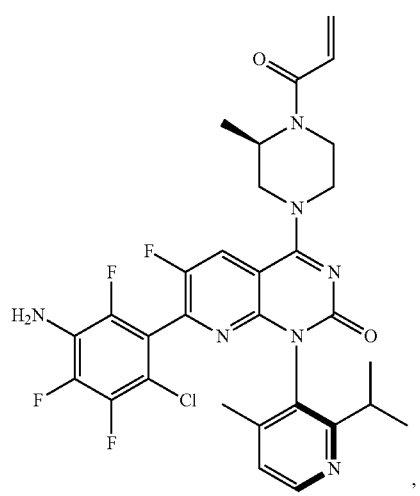
,
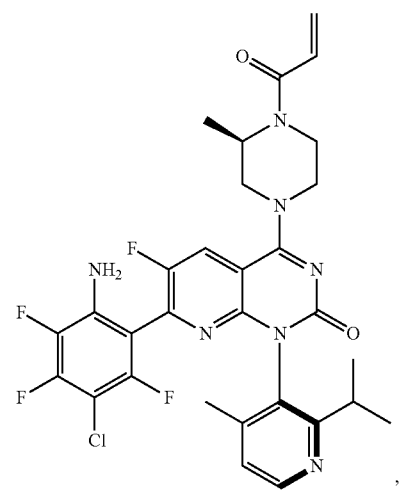
,
120
-continued
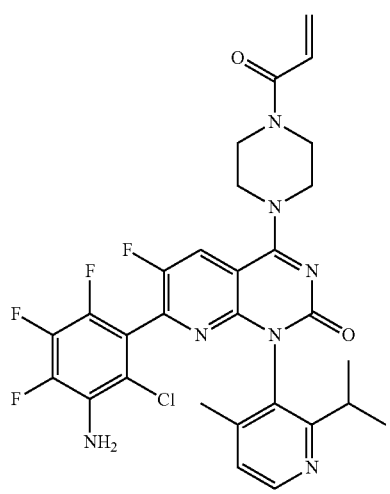
,
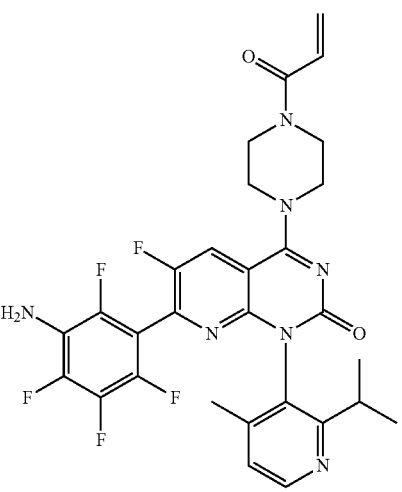
,
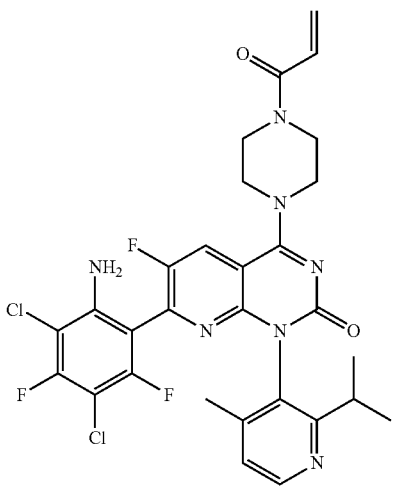
, 121
-continued
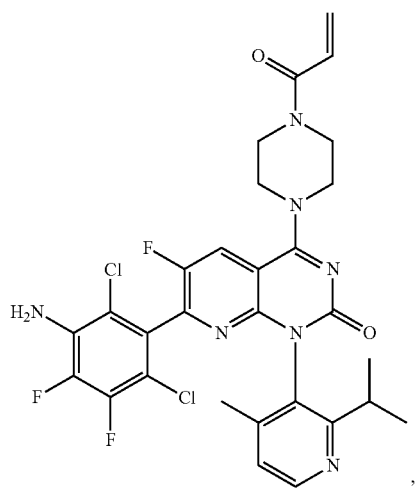
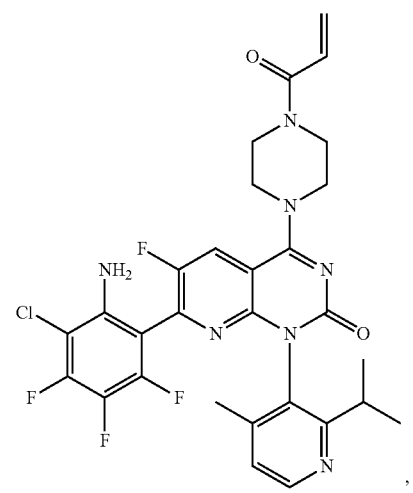
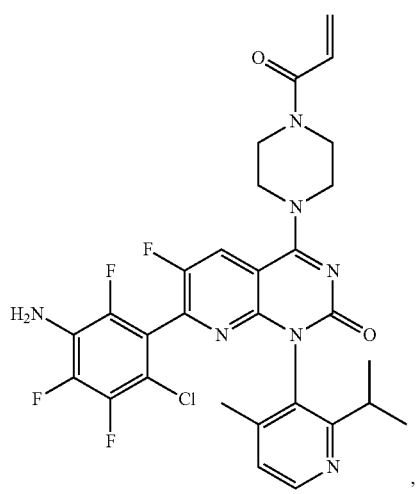
122
-continued
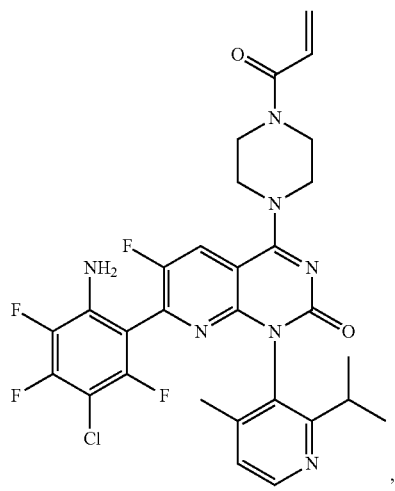
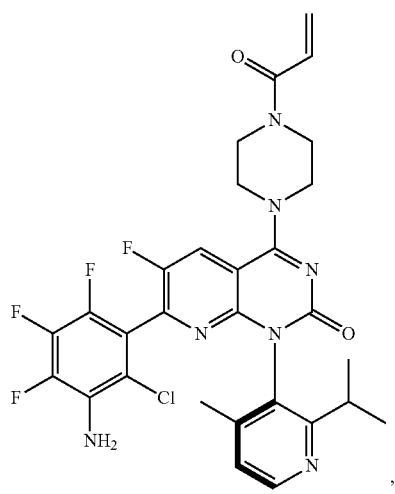
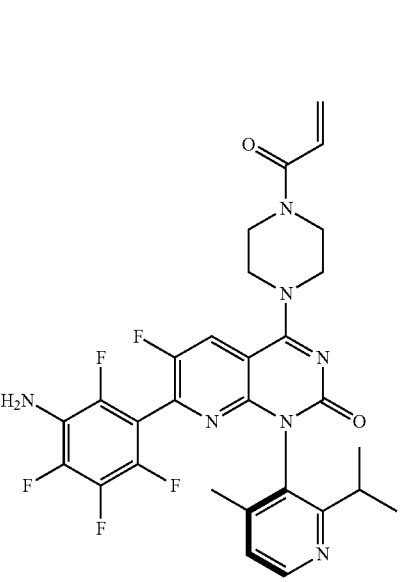

123
-continued
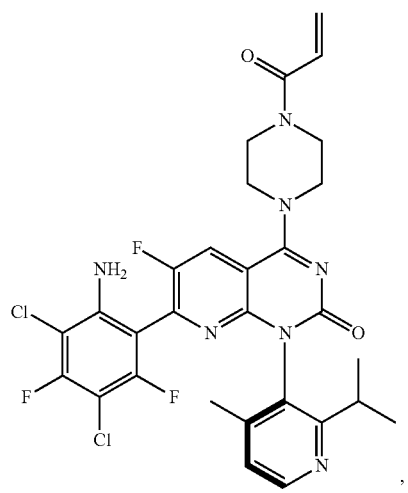
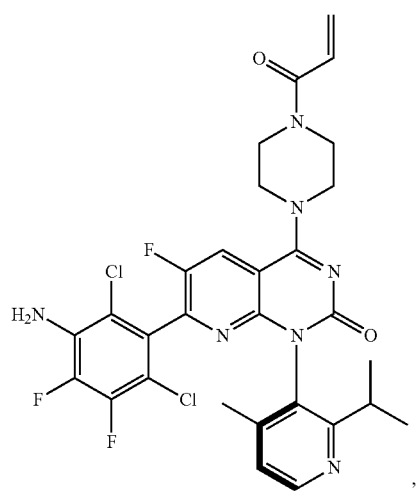
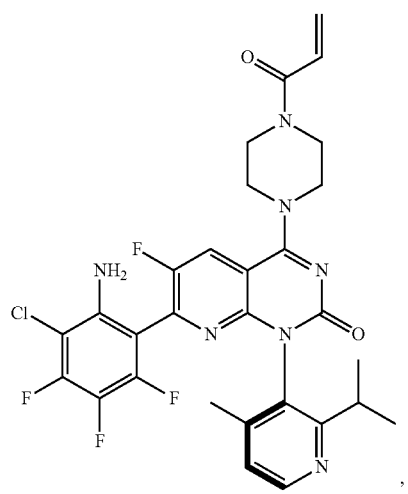
124
-continued
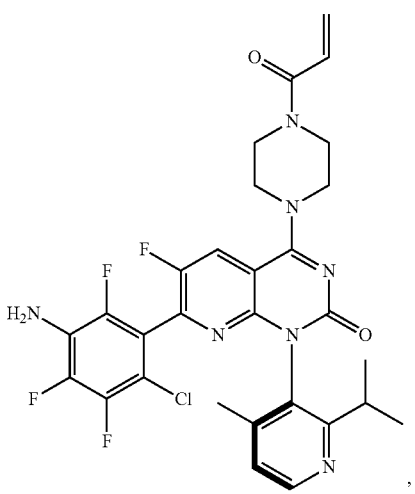
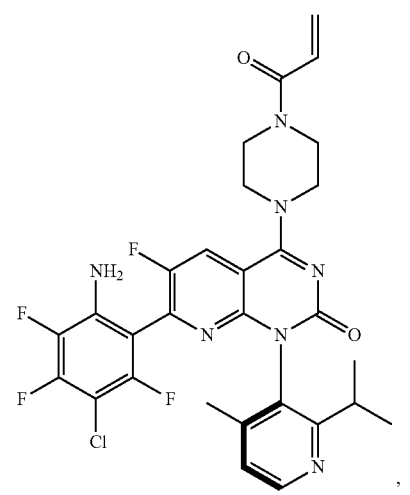
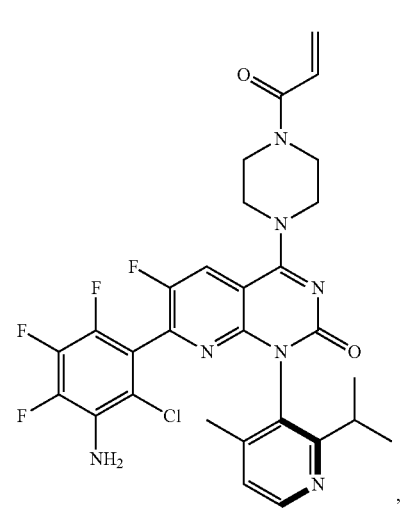

-continued
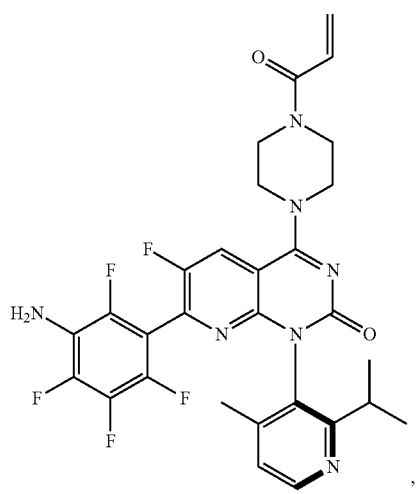
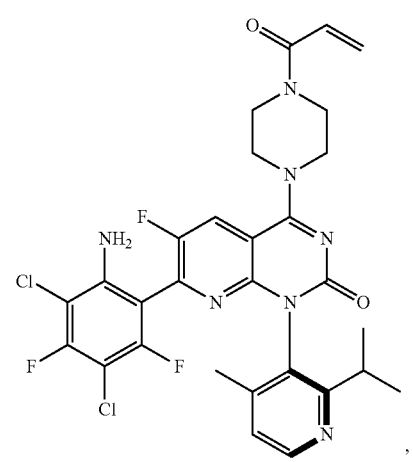
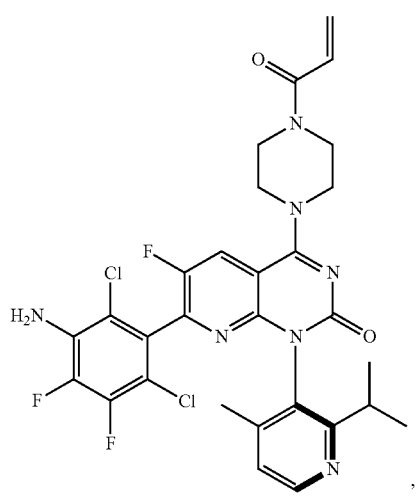
-continued
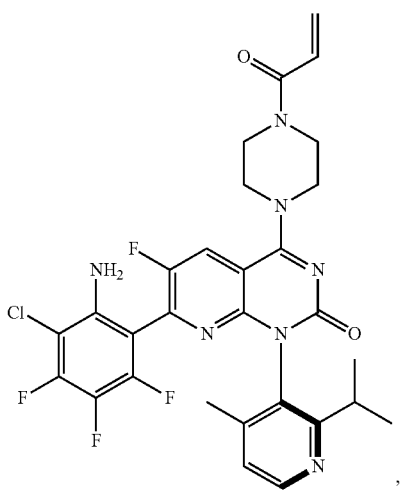
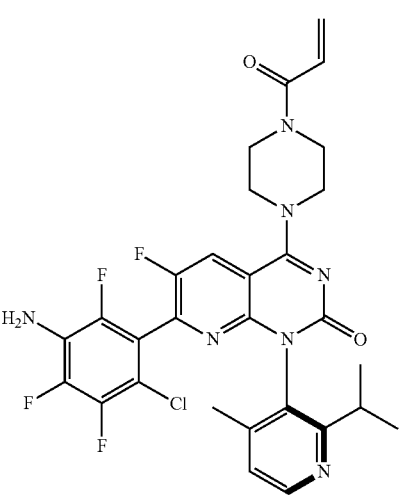
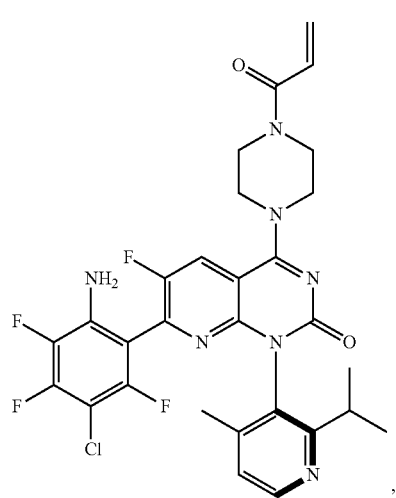

127
-continued
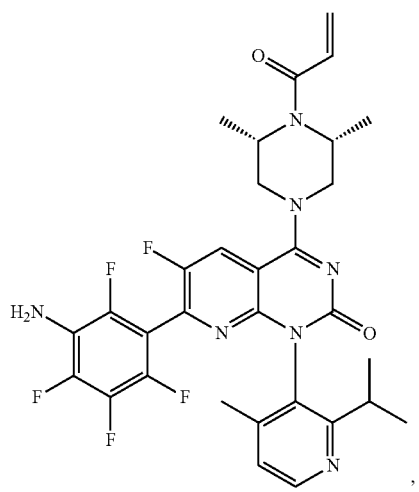
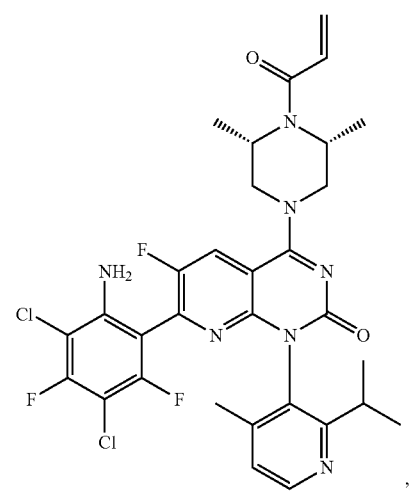
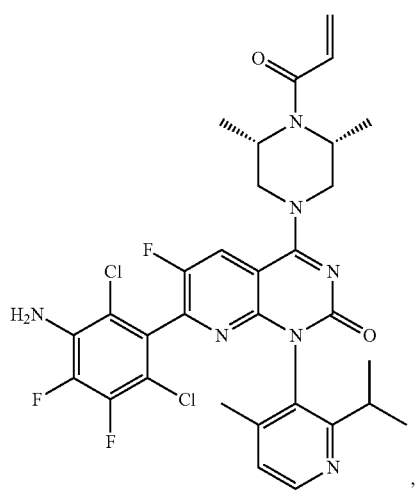
128
-continued
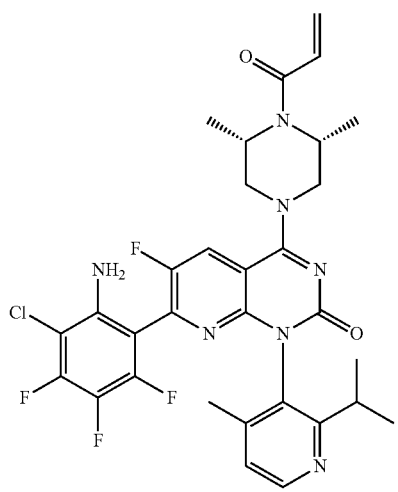
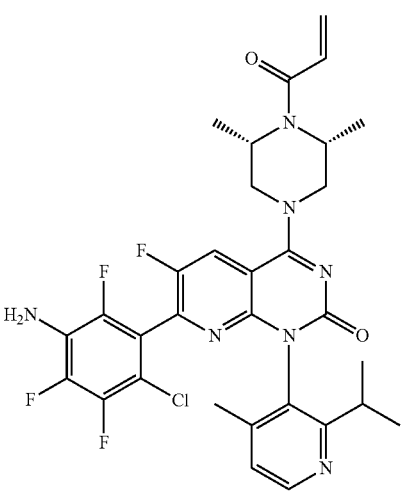
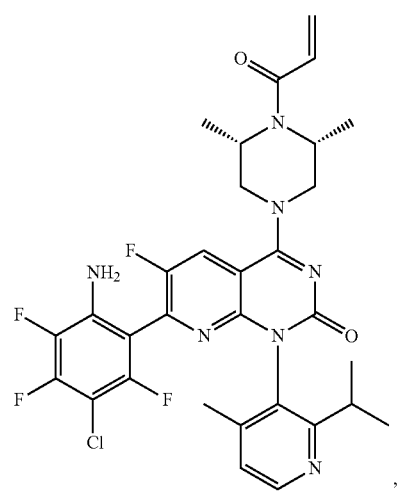

129
-continued
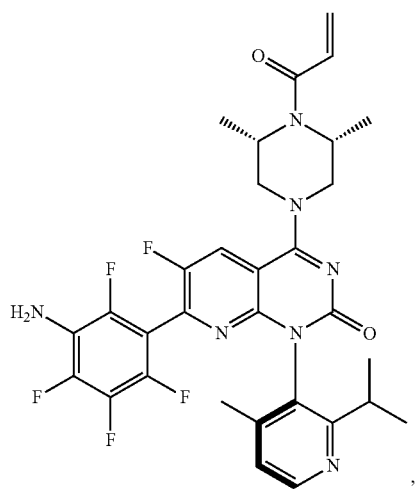
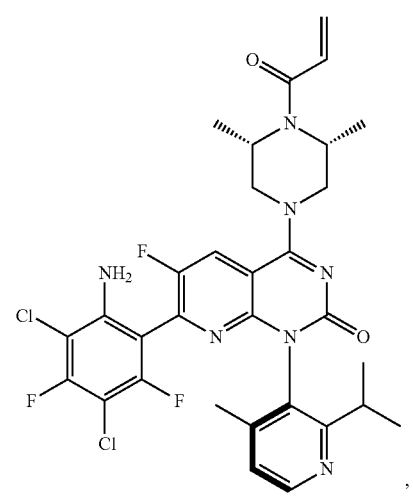
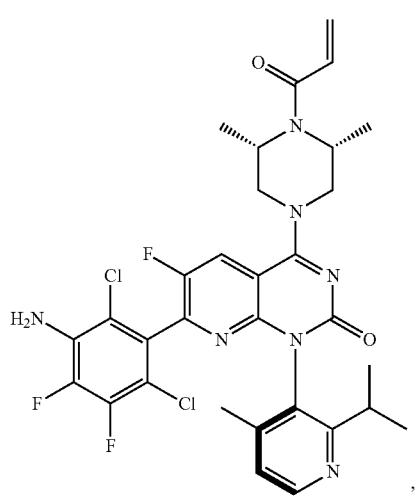
130
-continued
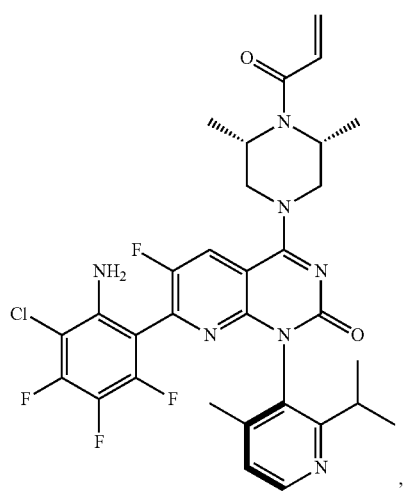
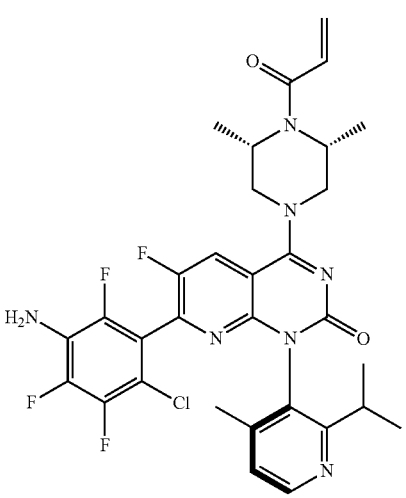
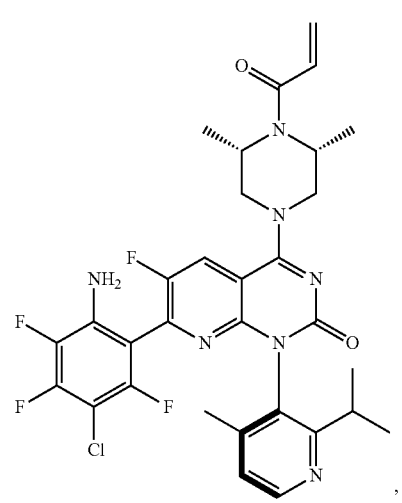

131
-continued
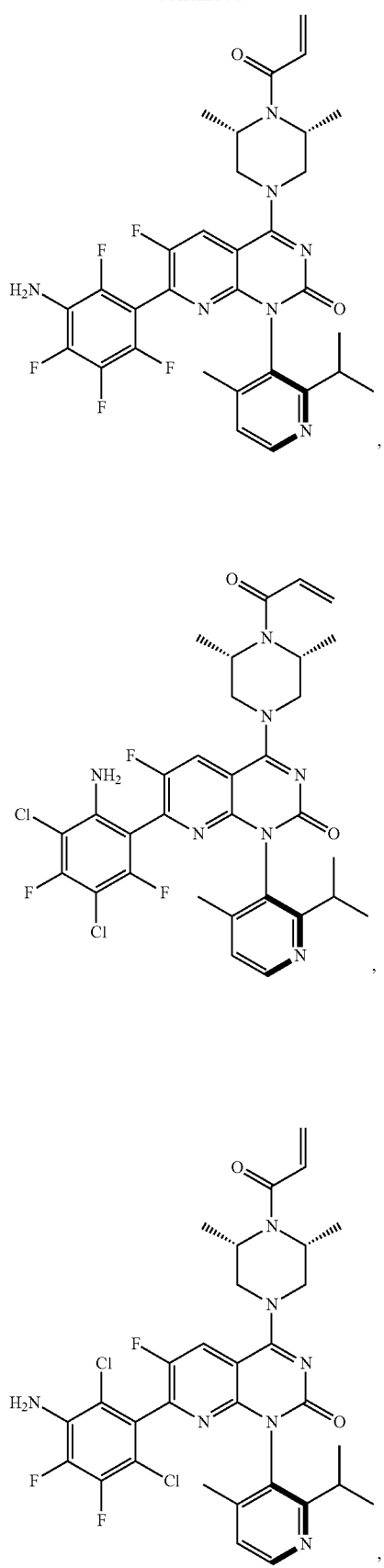
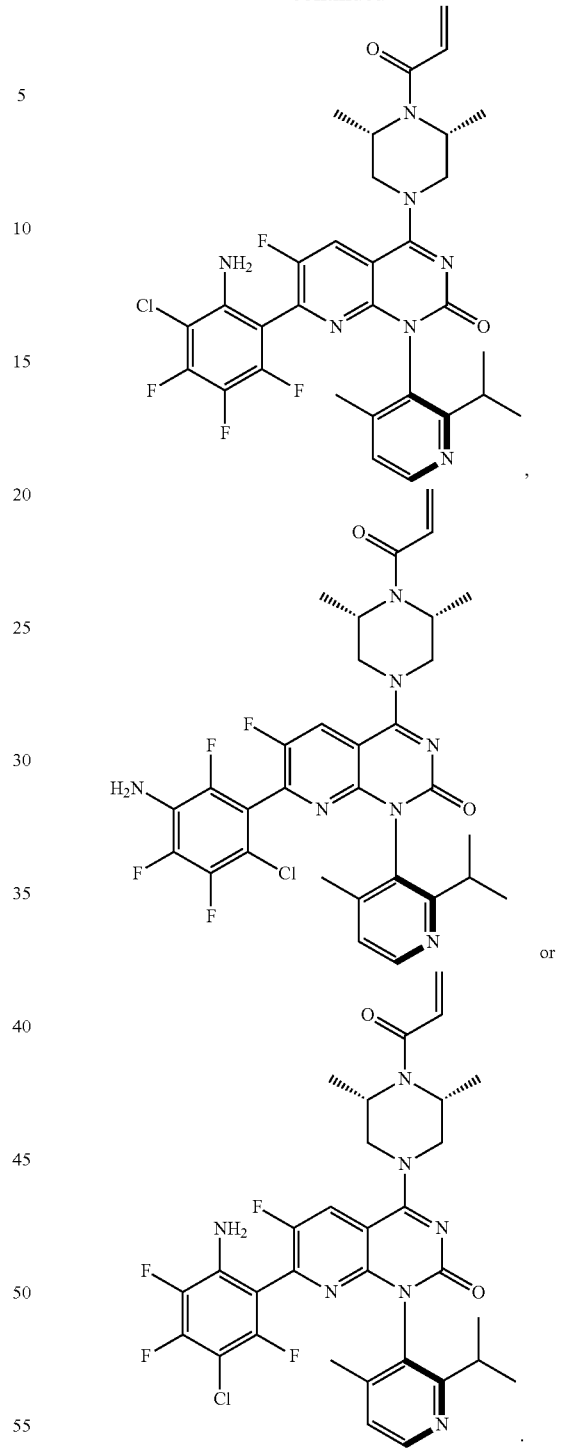
Pharmacological Testing
1. SOS1 Catalyzed Nucleotide Exchange Assay
HIS-KRAS(G12C, a4 2-185, Sino biological) was diluted to 5 M in EDTA buffer (20 mM HEPES, pH 7.4, 50 mM NaCl, 10 mM EDTA, 0.01% (v/v) Tween-20) and incubated for 30 min at 25° C. The EDTA pretreated HIS-KRAS (G12C) was diluted to 12 nM in assay buffer (25 mM HEPES, pH 7.4, 120 mM NaCl, 5 mM $MgCl_2$, 1 mM DTT, 0.01% (v/v) Tween 20, 0.1% (w/v) BSA) containing 120 nM GDP(Sigma) and MAb Anti 6HIS-Tb cryptate Gold(Cisbio) and incubated for 1 hour at 25° C. to prepare GDP-loaded HIS-KRAS(G12C). The GDP-loaded HIS-KRAS(G12C) was pre-incubation with diluted compounds in a 384-well plate (Greiner) for 1 hour, then purified SOS1 ExD(Flag tag, aa 564-1049) and BODIPY™ FL GTP (Invitrogen) were added to the assay wells (Final concentration: 3 nM HIS-KRAS(G12C), 2 µM SOS1 ExD, 80 nM BODIPY™ FL GTP, 21 ng/mL MAb Anti 6HIS-Tb cryptate Gold) and incubated for 4 hours at 25° C. TR-FRET signals were then read on Tecan Spark multimode microplate reader. The parameters were F486: Excitation 340 nm, Emission 486 nm, Lag time 100 is, Integration time 200 is; F515: Excitation 340 nm, Emission 515 nm, Lag time 100 is, Integration time 200 is. TR-FRET ratios for each individual wells were calculated by equation: TR-FRET ratio=(Signal F515/Signal F486)*10000. Then the data were analyzed using a 4-parameter logistic model to calculate $IC_{50}$ values. The results of the SOS1 catalyzed nucleotide exchange assay are in the following Table 2:

TABLE 2

| Compound | SOS1 catalyzed nucleotide exchange $IC_{50}$(nM) |
|---|---|
| Compound 1 | 7.25 |
| Compound 1-1 | 4.08 |
| Compound 1-2 | 121 |
| Compound 2 | 2.04 |
| Compound 2-1 | 1.19 |
| Compound 2-2 | 61.8 |
| Compound 3 | 5.51 |
| Compound 3-1 | 3.14 |
| Compound 3-2 | 234 |
| Compound 4 | 10.3 |
| Compound 4-1 | 3.31 |
| Compound 4-2 | 278 |
| Compound 5 | 5.41 |
| Compound 5-1 | 3.30 |
| Compound 5-2 | 96.1 |
| Compound 6 | 40.1 |
| Compound 7 | 17.5 |
| Compound 7-1 | 6.54 |
| Compound 7-2 | 307 |
| Amg-510 | 2.12 |

Amg-510 has the following structure:

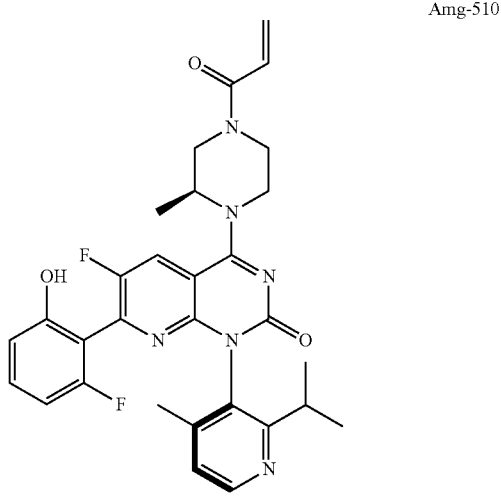

Amg-510

From the Table 2, it can be seen that the representative compounds in the present invention have good inhibitory activity under the SOS1 catalyzed nucleotide exchange assay, especially the Compound 2-1. The inhibitory activity of the Compound 2-1 can reach about 2 times as much as that of the control compound Amg-510.

2. Phospho-ERK1/2(THR202/TYR204) HTRF Assay

NCI-H358 cells expressing KRAS G12C mutant protein were cultured in RPMI 1640 medium (Gibco) containing 10% fetal bovine serum (Gibco). The NCI-H358 cells in culture medium were seeded in 96-well plates at a concentration of 40,000 cells/well and then put in a 37° C./5% $CO_2$ cell incubator to incubate overnight. In the next day, the culture medium was removed and the compound diluted in assay medium (RPMI 1640, 0.1% FBS) was added in each well. After 2 hours incubation in a 37° C./5% $CO_2$ cell incubator, the assay medium in 96-well plates was removed, then 50 µL of 1× blocking reagent-supplemented lysis buffer (Cisbio) was added and the plates were incubated at 25° C. for 45 min with shaking. 10 µL of cell lysates from the 96-well plates were transferred to a 384-well plate (Greiner) containing 2.5 µL/well HTRF® pre-mixed antibodies (Cisbio 64AERPEH). Incubate 4 hours at 25° C. and then read HTRF signals on Tecan Spark multimode microplate reader. The data were analyzed using a 4-parameter logistic model to calculate $IC_{50}$ values. The results of the Phospho-ERK1/2(THR202/TYR204) HTRF assay are in the following Table 3:

TABLE 3

| Compound | p-ERK $IC_{50}$(nM) |
|---|---|
| Compound 1 | 70.1 |
| Compound 1-1 | 16.6 |
| Compound 1-2 | ND |
| Compound 2 | 30.7 |
| Compound 2-1 | 14.5 |
| Compound 2-2 | 681 |
| Compound 3 | ND |
| Compound 3-1 | 25.4 |
| Compound 3-2 | ND |
| Compound 4 | ND |
| Compound 4-1 | 40.9 |
| Compound 4-2 | ND |
| Compound 5 | 48.8 |
| Compound 5-1 | 17.8 |
| Compound 5-2 | 774 |
| Compound 6 | ND |
| Compound 7 | ND |
| Compound 7-1 | 36.7 |
| Compound 7-2 | ND |
| Amg-510 | 24.5 |

ND refers to Not Detected.

ND refers to Not Detected.

From the Table 3, it can be seen that the representative compounds in the present invention have good inhibition activity under phospho-ERK1/2(THR202/TYR204) HTRF assay, especially the Compound 2-1. The inhibitory activity of the Compound 2-1 can reach about 2 times as much as that of the control compound Amg-510.

3. Mouse Pharmacokinetic Study

The purpose of this study was to evaluate the pharmacokinetic properties of compounds in Balb/c mouse (♀) following single dose administration. The day before administration, mice were fasted overnight and free access to water. Six mice were needed for each compound and the six mice were divided into two groups (n=3/group), group A and group B. Mice in group A were treated with a single 3 mg/kg dose of compound (iv). Mice in group B were treated with a single 10 mg/kg dose of compound (po). For each mouse in group A, blood samples were collected at pre-dose, and at the time point of 0.083, 0.25, 0.5, 1, 2, 4, 6, 8 and 24 h post-dose. For each mouse in group B, blood samples were collected at pre-dose, and at the time point of 0.25, 0.5, 1, 2, 3, 4, 6, 8 and 24 h post-dose. Blood samples were placed on ice until centrifugation to obtain plasma samples. The plasma samples were stored at −80° C. until analysis. The concentration of compound in plasma samples was determined using a LC-MS/MS method. The results are in the following Table 4:

TABLE 4

| Compound | 3 mg/kg, iv | | 10 mg/kg, po | | |
|---|---|---|---|---|---|
| | CL (mL/min/kg) | Vss (L/kg) | $C_{max}$ (ng/mL) | $AUC_{0-24\,h}$ (ng · h/mL) | Oral BA (F %) |
| Compound 2 | 65.2 | 2.31 | 1437 | 1147 | 44.7 |
| Compound 2-1 | 38.9 | 1.28 | 2440 | 2618 | 58.9 |
| Amg-510 | 40.5 | 1.64 | 1603 | 1812 | 43.9 |

From Table 4, it can be seen that the representative Compound 2 and Compound 2-1 have good pharmacokinetic properties in mouse model, especially the Compound 2-1 which has the higher $C_{max}$ and $AUC_{0-24\,h}$ comparative with the Amg-510, which makes Compound 2-1 more suitable for treating cancers with KRAS G12C mutation as an orally therapeutic active ingredient in clinic.

4. Dog Pharmacokinetic Study

The purpose of this study was to evaluate the pharmacokinetic properties of compounds in beagle dog following single dose administration. The day before administration, dogs were fasted overnight and free access to water. Four beagle dogs were needed for each compound and the four dogs were divided into two groups, group A and group B (one male(♂) and one female (♀) in each group). Dogs in group A were treated with a single 1 mg/kg dose of compound (iv). Dogs in group B were treated with a single 3 mg/kg dose of compound (po). For dogs in group A, blood samples were collected at pre-dose, and at the time point of 0.083, 0.25, 0.5, 1, 2, 4, 6, 8 and 24 h post-dose. For dogs in group B, blood samples were collected at pre-dose, and at the time point of 0.25, 0.5, 1, 2, 4, 6, 8 and 24 h post-dose. Blood samples were placed on ice until centrifugation to obtain plasma samples. The plasma samples were stored at −80° C. until analysis. The concentration of compound in plasma samples was determined using a LC-MS/MS method. The results are in following Table 5:

TABLE 5

| Compound | Sex | 1 mg/kg, iv | | 3 mg/kg, po | | |
|---|---|---|---|---|---|---|
| | | CL (mL/min/kg) | $V_{SS}$ (L/kg) | $C_{max}$ (ng/mL) | $AUC_{0-24h}$ (ng · h/mL) | Oral BA (F %) |
| Compound 2-1 | ♂ | 4.15 | 0.255 | 4080 | 7308 | 60.9 |
| | ♀ | 4.40 | 0.295 | 2330 | 5022 | 44.3 |
| Amg-510 | ♂ | 21.1 | 0.535 | 1840 | 1994 | 84.4 |
| | ♀ | 20.1 | 0.543 | 450 | 404 | 16.4 |

From Table 5, it can be seen that Compound 2-1 has excellent pharmacokinetic properties in beagle dog model comparative with the Amg-510. The $C_{max}$ and $AUC_{0-24\,h}$ of Compound 2-1 are both significantly more than Amg-510, for example, the $AUC_{0-24\,h}$ of the Compound 2-1 in male beagle dog can reach more than 3 times as much as that of the control compound Amg-510, and the $AUC_{0-24\,h}$ of Compound 2-1 in female beagle dog can reach more than 12 times as much as that of the control compound Amg-510, which makes the Compound 2-1 more suitable for treating cancers with KRAS G12C mutation as an orally therapeutic active ingredient in clinic.

5. Cynomolgus Monkey Pharmacokinetic Study

The purpose of this study was to evaluate the pharmacokinetic properties of compounds in cynomolgus monkey following single dose administration. The day before administration, monkeys were fasted overnight and free access to water. Four monkeys are needed for each compound and the four monkeys were divided into two groups, group A and group B (one male (♂) and one female (♀) in each group). Monkeys in group A were treated with a single 1 mg/kg dose of compound (iv). Monkeys in group B were treated with a single 3 mg/kg dose of compound (po). For monkeys in group A, blood samples were collected at pre-dose, and at the time point of 0.083, 0.25, 0.5, 1, 2, 4, 6, 8 and 24 h post-dose. For monkeys in group B, blood samples were collected at pre-dose, and at the time point of 0.25, 0.5, 1, 2, 4, 6, 8 and 24 h post-dose. Blood samples were placed on ice until centrifugation to obtain plasma samples. The plasma samples were stored at −80° C. until analysis. The concentration of compound in plasma samples was determined using a LC-MS/MS method. The results are in following Table 6:

TABLE 6

| Compound | Sex | 1 mg/kg, iv | | 3 mg/kg, po | | |
|---|---|---|---|---|---|---|
| | | CL (mL/min/kg) | $V_{SS}$ (L/kg) | $C_{max}$ (ng/mL) | $AUC_{0-24h}$ (ng · h/mL) | Oral BA (F %) |
| Compound 2-1 | ♂ | 8.26 | 0.555 | 1580 | 3253 | 54.1 |
| | ♀ | 8.20 | 0.507 | 1060 | 2494 | 41.2 |
| Amg-510 | ♂ | 25.5 | 0.775 | 133 | 214 | 11.0 |
| | ♀ | 84.3 | 2.01 | 100 | 241 | 41.3 |

From Table 6, it can be seen that Compound 2-1 has excellent pharmacokinetic properties in monkey model. The $C_{max}$ and $AUC_{0-24\,h}$ of Compound 2-1 are significantly more than Amg-510, for example, the $AUC_{0-24\,h}$ of the Compound 2-1 in male cynomolgus monkey can reach more than 15 times as much as that of the control compound Amg-510, and the $AUC_{0-24\,h}$ of Compound 2-1 in female cynomolgus monkey can reach more than 10 times as much as that of the control compound Amg-510, which makes the Compound 2-1 more suitable for treating cancers with KRAS G12C mutation as an orally therapeutic active ingredient in clinic.

6. The Efficacy in NCI-H1373 ($KRAS^{G12C}$) Xenograft Model

NCI-H1373 ($KRAS^{G12C}$) cells (5.0E+06 cells) were injected subcutaneously into the right flank of female BALB/c nude mice (6-8 weeks) in a mixture with PBS and Matrigel (Corning) (PBS/Matrigel=1:1(v/v)). Mice were monitored daily and caliper measurements began when tumors became visible. Tumor volume was calculated by measuring two perpendicular diameters using the formula: $(L*W^2)/2$ in which L and W refer to the length and width tumor diameter respectively. When the average tumor volume reached 150-200 mm³, mice were grouped randomly (n=6/group) and treated with compounds. Tumor volume and mice weight was measured twice a week during treatment (~ 3 weeks). Tumor growth inhibition rates were calculated by TGI %=(1−(Vt−Vt₀)/(Vc−Vc₀))*100%, wherein Vc and Vt are the mean tumor volume of control and treated groups at the end of the study respectively, and $Vc_0$ and $Vt_0$ are the mean tumor volume of control and treated groups at the start respectively. The results are in the following Table 7 and FIG. 1:

TABLE 7

| Groups | Tumor volume at the start, mm³ | Tumor volume at the end (Day 21), mm³ | TGI % |
|---|---|---|---|
| Vehicle | 193 | 1879 | — |
| Compound 2-1, 10 mg/kg, QD | 192 | 27 | 110 |

From Table 7 and FIG. 1, it can be seen that the Compound 2-1 has excellent efficacy in vivo and the regression of the tumor has been observed.

7. Safety Exploration in SW837 (KRAS$^{G12C}$) xenograft model

Figure 2:
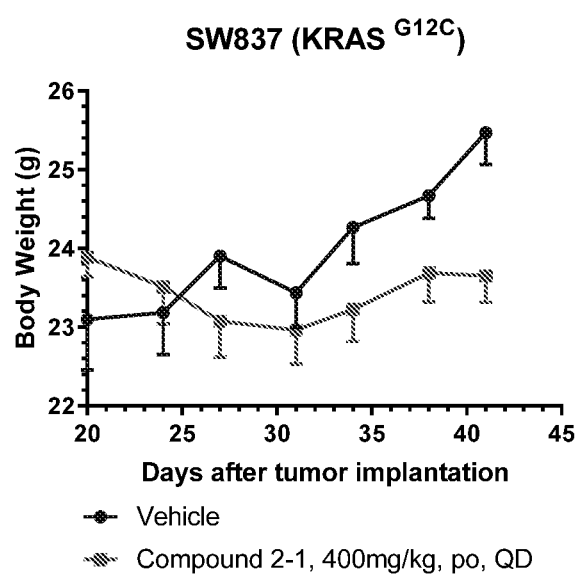
FIG. 2 is the graph of body weight varying with the days after tumor implantation after administration of compound 2-1 or vehicle in SW837 (KRAS$^{G12C}$) xenograft model.

SW837 (KRAS$^{G12C}$) cells (1.0E+07 cells) were injected subcutaneously into the right flank of female NOD SCID mice (6-8 weeks) in a mixture with PBS and Matrigel (Corning) (PBS/Matrigel=1:1(v/v)). Mice were monitored daily and caliper measurements began when tumors became visible. Tumor volume was calculated by measuring two perpendicular diameters using the following formula: (L*W²)/2 in which L and W refer to the length and width tumor diameter respectively. After mice were grouped to study the efficacy, the remaining mice (n=8) were used to explore the safety. The mice were treated with 400 mg/kg Compound 2-1 (po, QD) for 22 days, and mice body weight was measured twice a week during treatment. The weight of mice varies with the number of days after cell inoculation is shown in FIG. 2. From FIG. 2, it can be seen that the Compound 2-1 has good safety.

It is to be understood that, if any prior art publication is referred to herein; such reference does not constitute an admission that the publication forms a part of the common general knowledge in the art in any country. Although the foregoing invention has been described in some detail by way of illustration and example for purposes of clarity of understanding, it is apparent to those skilled in the art that certain minor changes and modifications will be practiced. Therefore, the description and Examples should not be construed as limiting the scope of the invention.

What is claimed is:

1. A compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof:

(I)

Wherein:

the

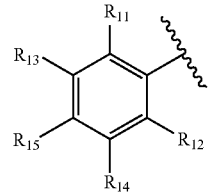

in the formula (I) is selected from:

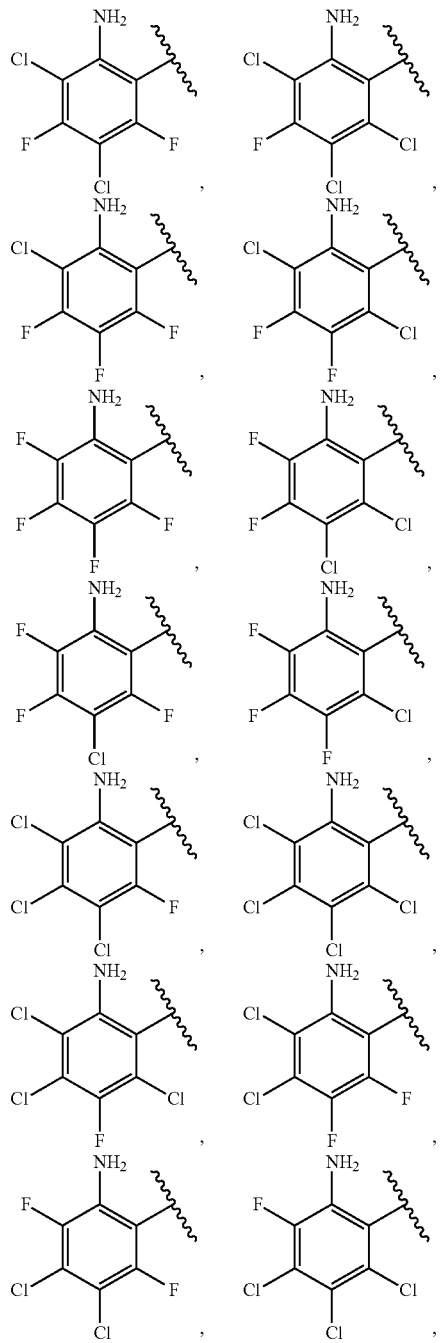

-continued
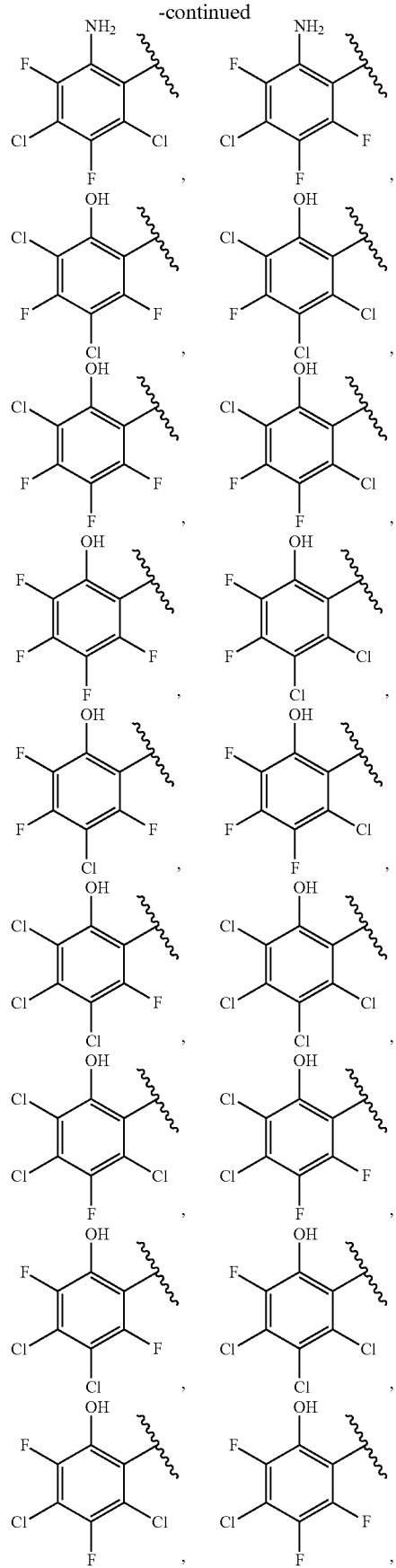
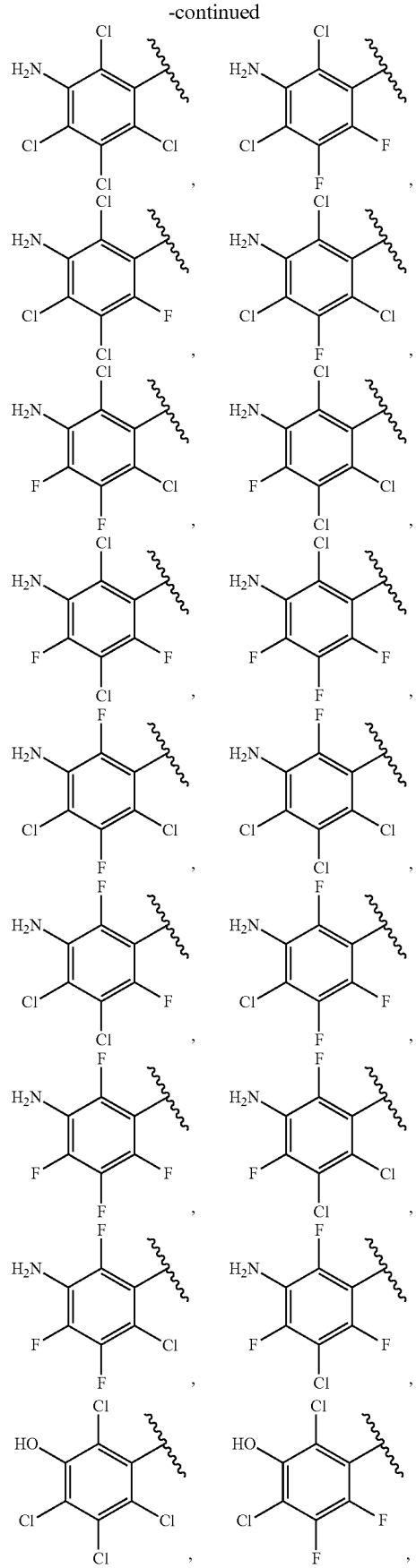

-continued

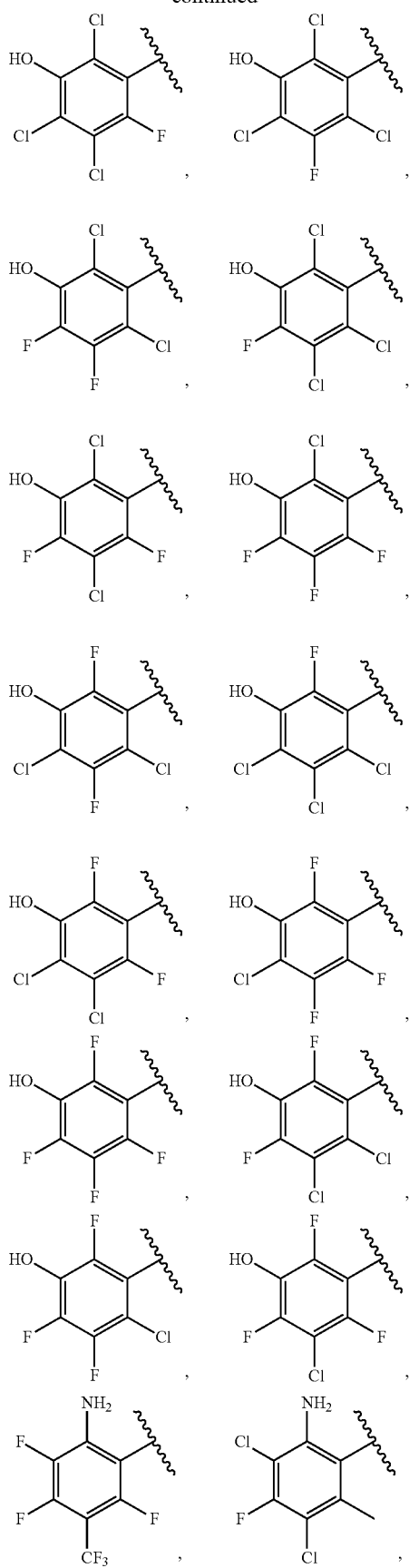

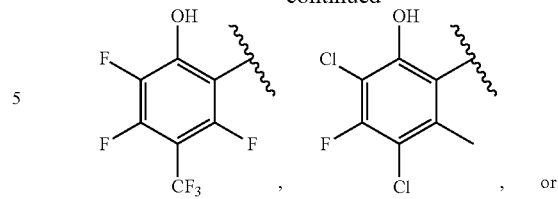

$R_{21}$ is selected from halogen;
$R_{22}$ is selected from hydrogen;
$R_3$ is selected from

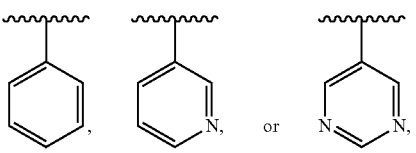

each hydrogen in the $R_3$ at each occurrence is independently optionally substituted by 1 $R_{31}$ or 2 $R_{31}$;
Each $R_{31}$ at each occurrence is independently selected from —$C_{1-6}$alkyl;
$R_4$ is selected from

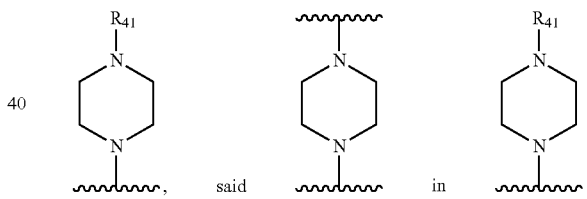

is independently optionally substituted by 1 $R_{42}$ or 2 $R_{42}$;
$R_{41}$ is selected from

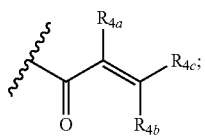

$R_{4a}$, $R_{4b}$ or $R_{4c}$ is independently selected from hydrogen or halogen;
Each $R_{42}$ at each occurrence is independently selected from —$C_{1-6}$alkyl or —$C_{1-6}$alkylene-CN.

2. The compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof according to claim 1, wherein:
$R_{21}$ is selected from —F.

3. The compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof according to claim 1, wherein:

R$_3$ is selected from

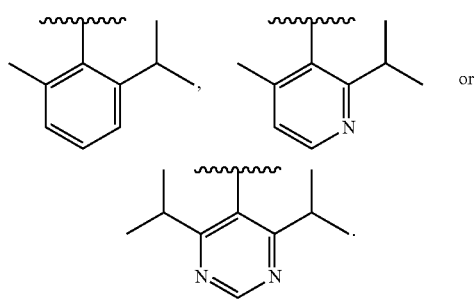

4. The compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof according to claim 3, wherein:

R$_3$ is selected from

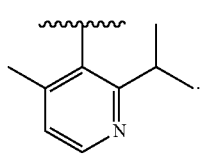 [SMILES: *c1c(C)ccnc1C(C)C]

5. The compound of formula (I), the stereoisomer thereof, the atropisomer thereof, the pharmaceutically acceptable salt thereof, the pharmaceutically acceptable salt of the stereoisomer thereof or the pharmaceutically acceptable salt of the atropisomer thereof according to claim 1, wherein:

R$_4$ is selected from:

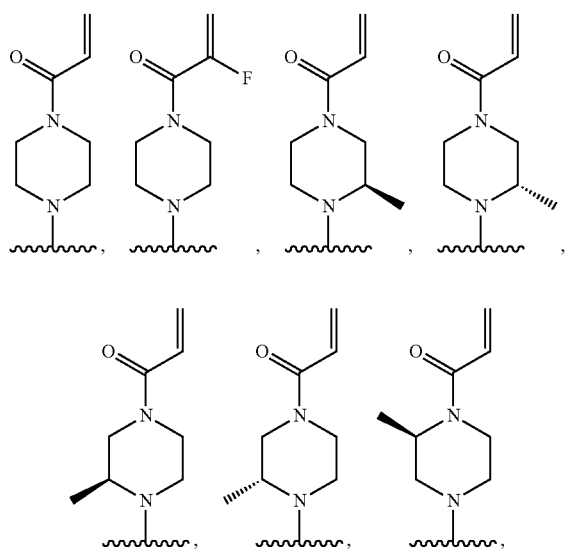

-continued

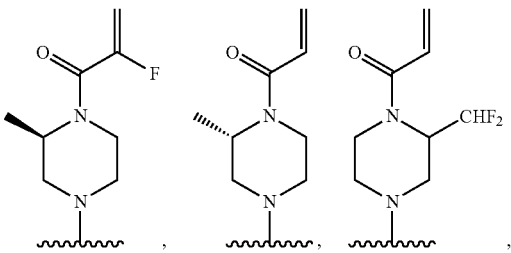

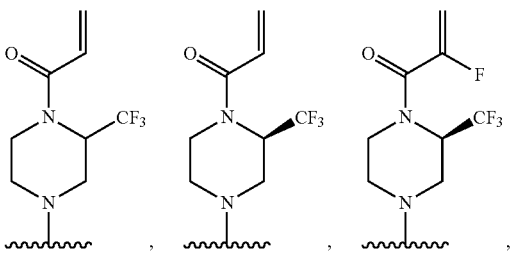

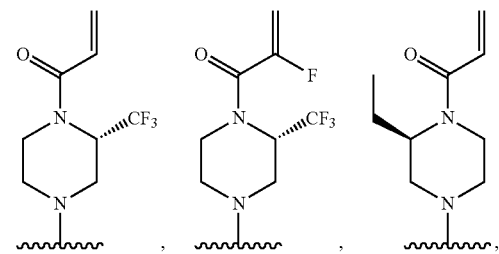

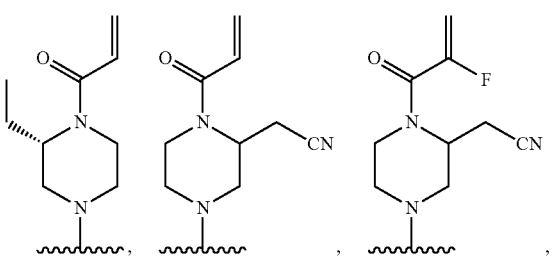

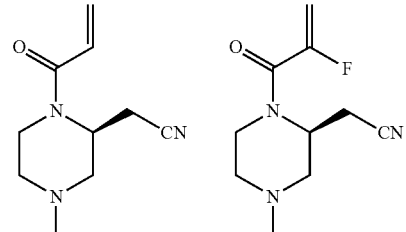

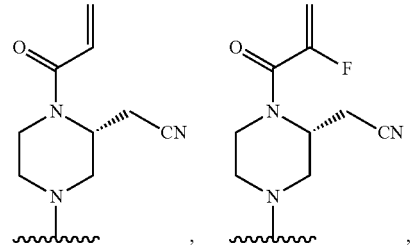

-continued

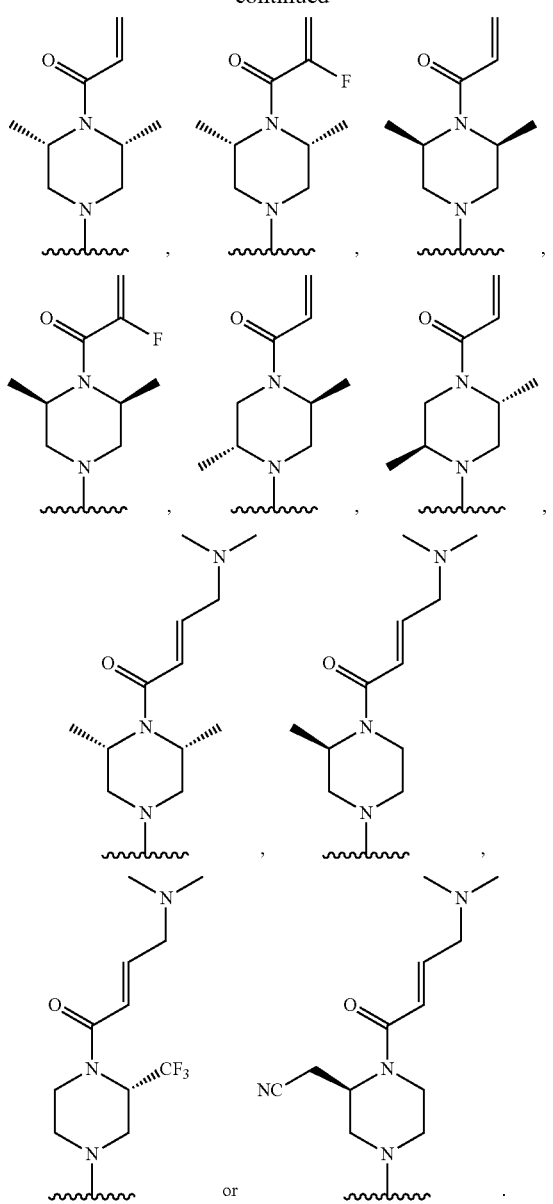

6. The compound of formula (I), the stereoisomer thereof, the atropisomer thereof, the pharmaceutically acceptable salt thereof, the pharmaceutically acceptable salt of the stereoisomer thereof or the pharmaceutically acceptable salt of the atropisomer thereof according to claim 5, wherein:

R$_4$ is selected from:

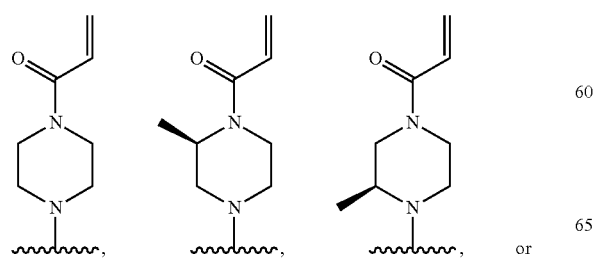

-continued

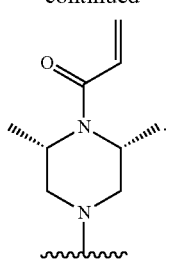

7. The compound of formula (I), the stereoisomer thereof, the atropisomer thereof, the pharmaceutically acceptable salt thereof, the pharmaceutically acceptable salt of the stereoisomer thereof or the pharmaceutically acceptable salt of the atropisomer thereof according to claim 6, wherein:

R$_4$ is selected from:

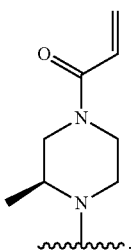

8. The compound of formula (I), the stereoisomer thereof, the atropisomer thereof, the pharmaceutically acceptable salt thereof, the pharmaceutically acceptable salt of the stereoisomer thereof or the pharmaceutically acceptable salt of the atropisomer thereof according to claim 1, wherein:

the compound is selected from:

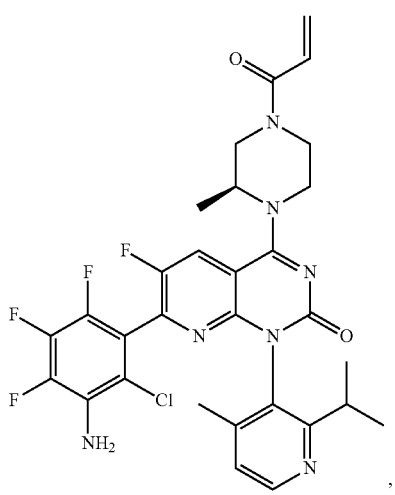

147
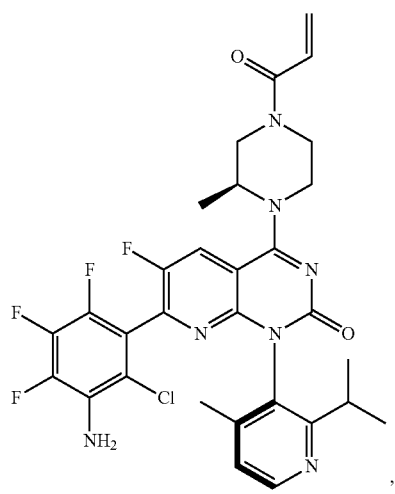
,
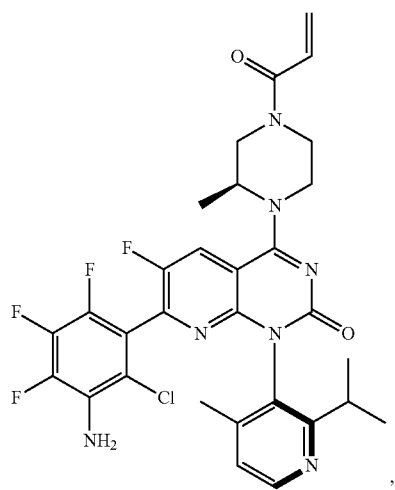
,
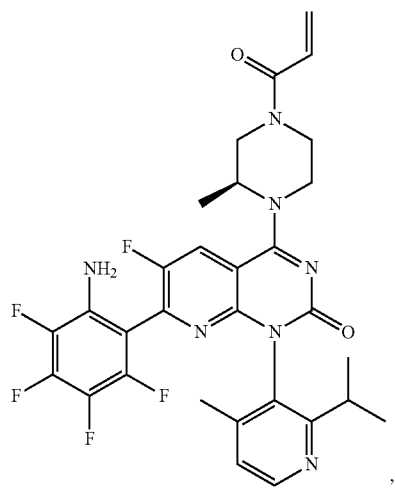
,
148
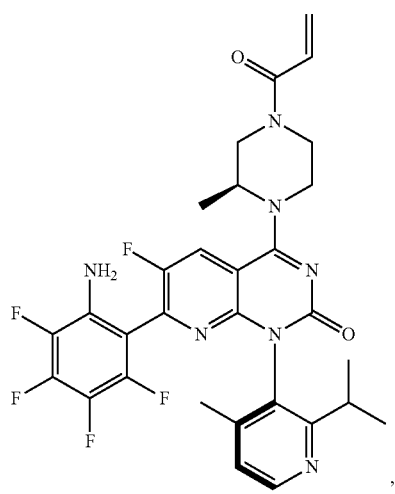
,
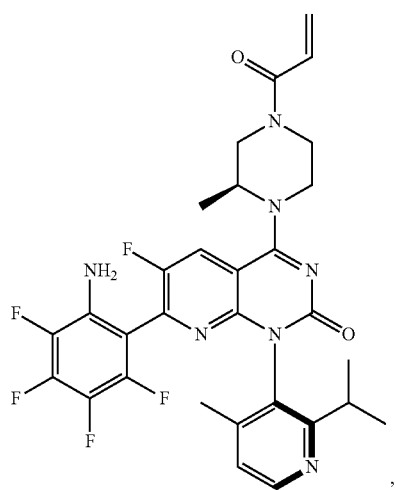
,
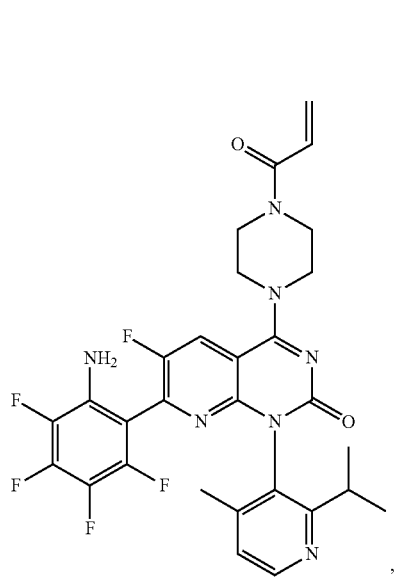
, 149
-continued
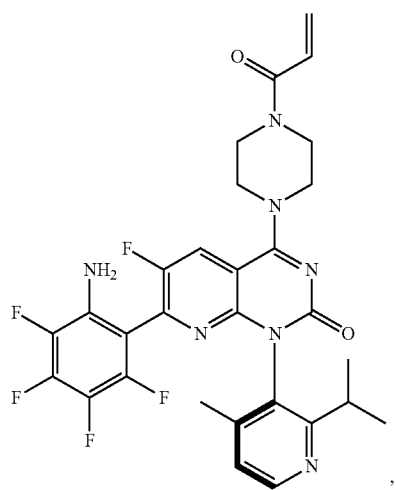
,
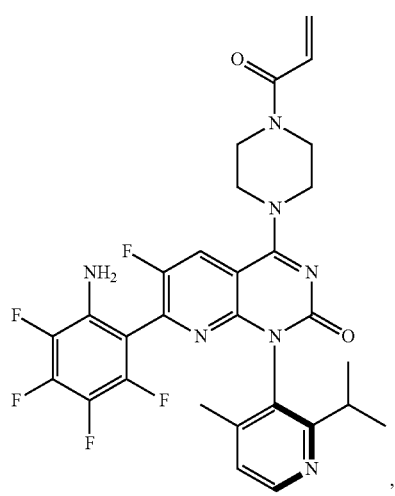
,
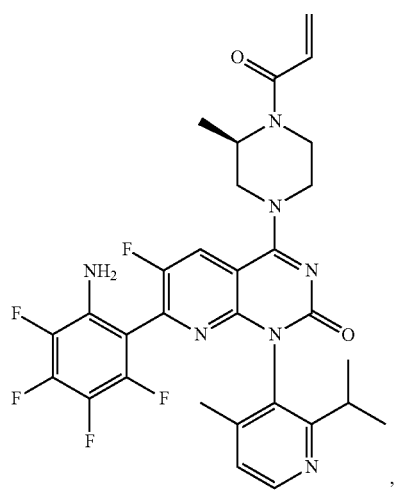
,
150
-continued
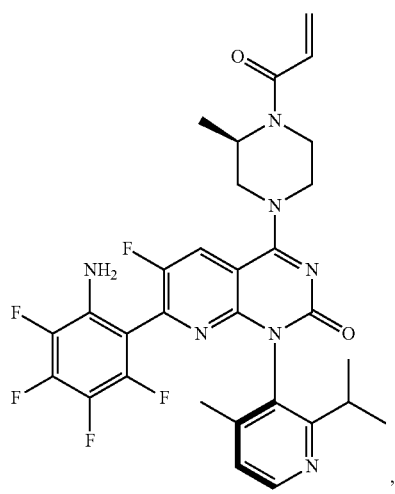
,
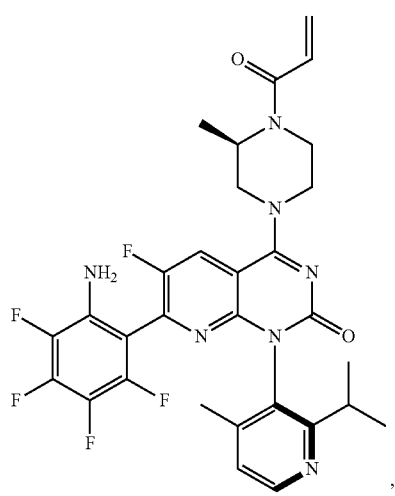
,
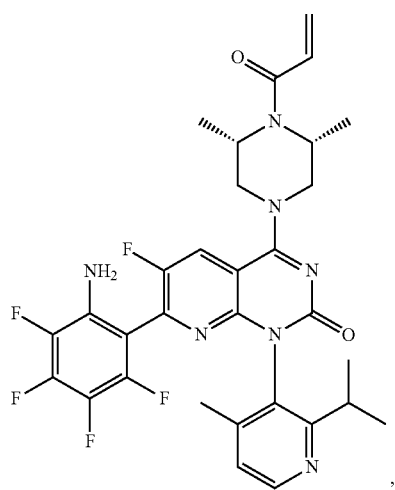
, 151
-continued
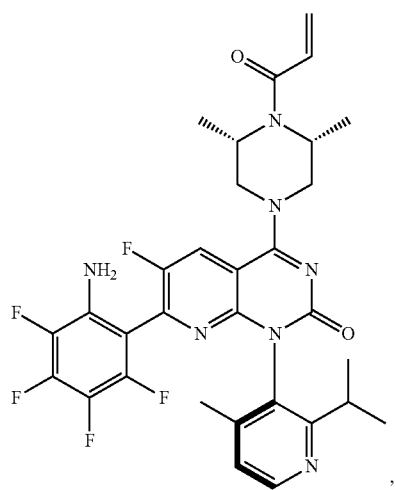
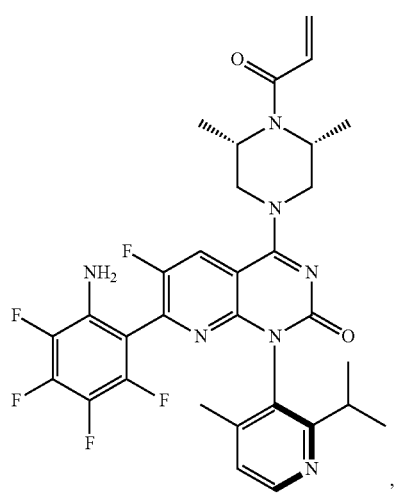
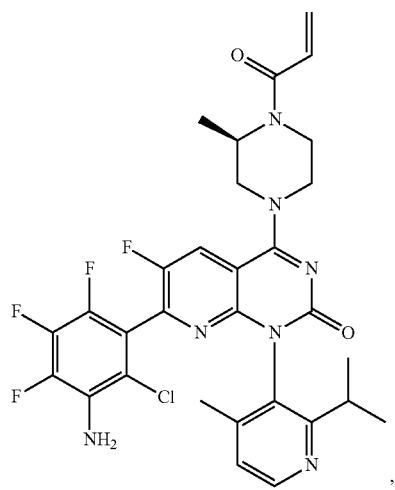
152
-continued
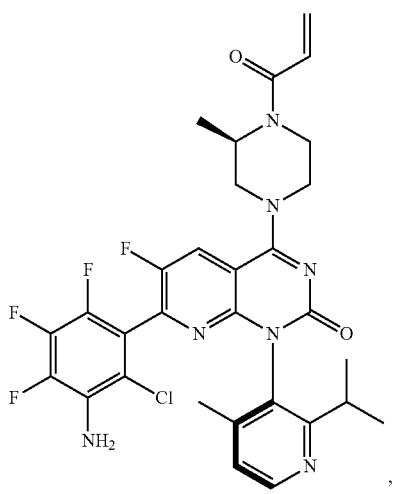
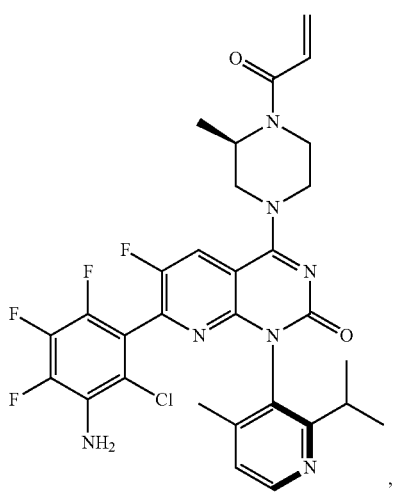
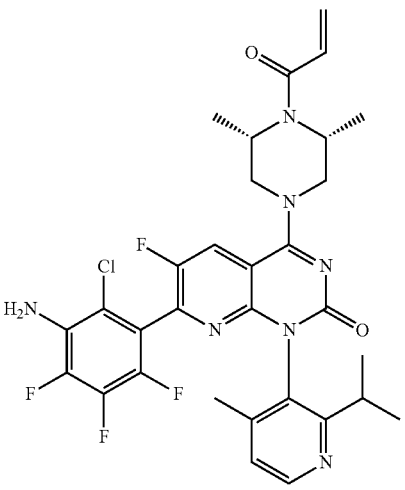

153
-continued
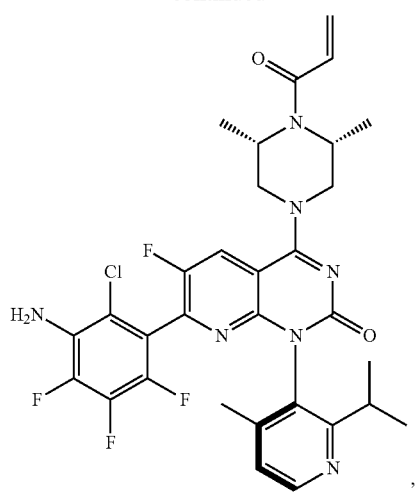
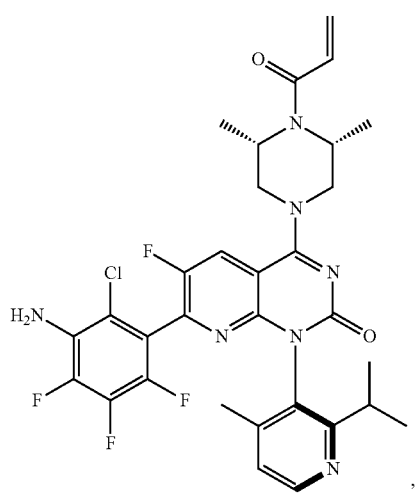
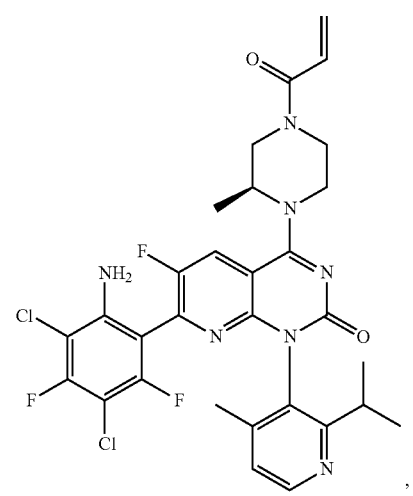
154
-continued
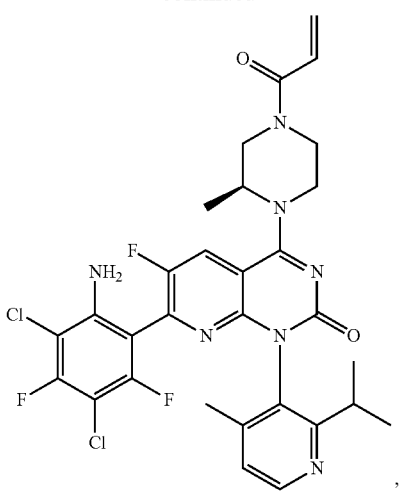
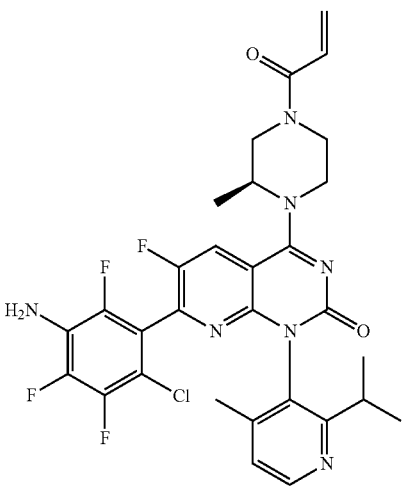

155
-continued
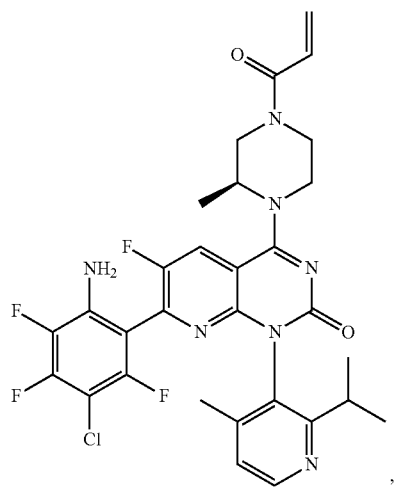
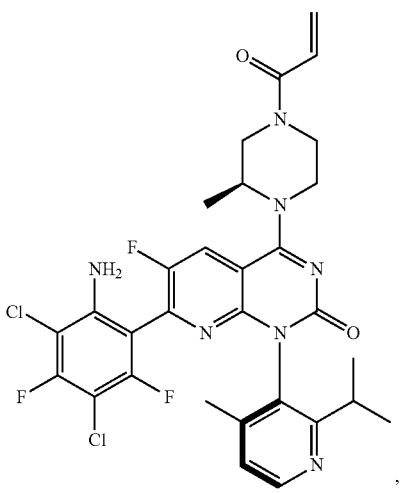
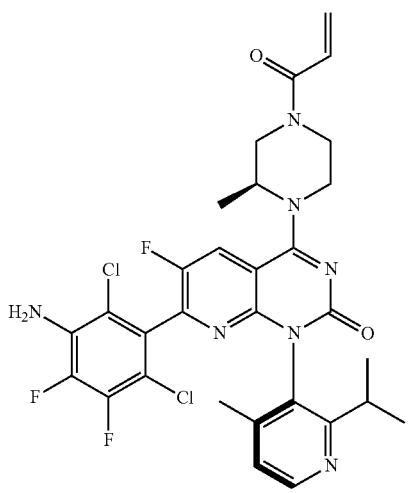
156
-continued
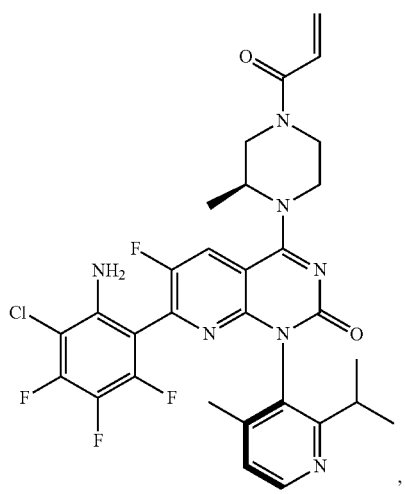
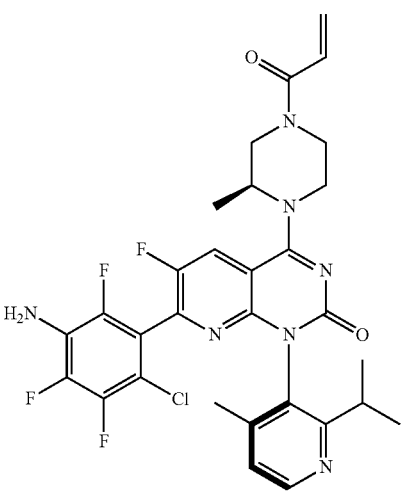
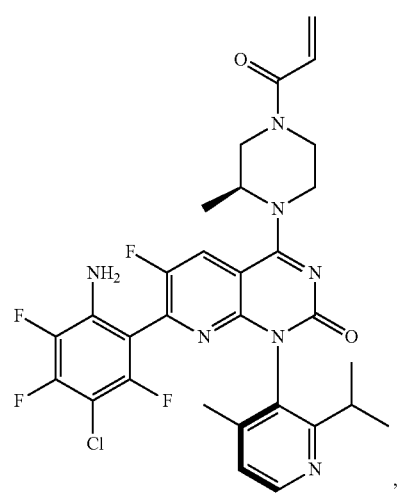

157
-continued
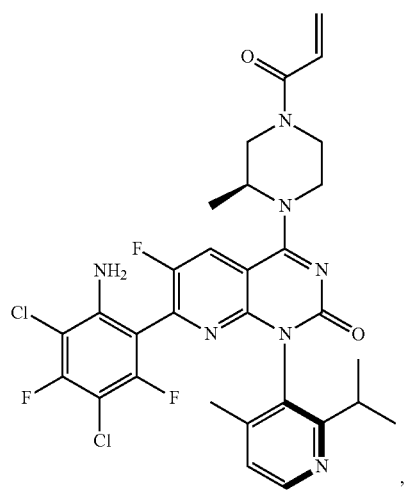
,
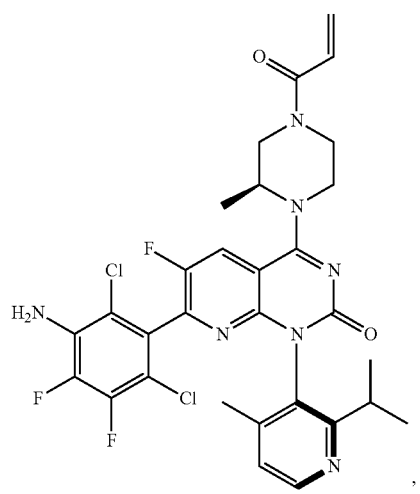
,
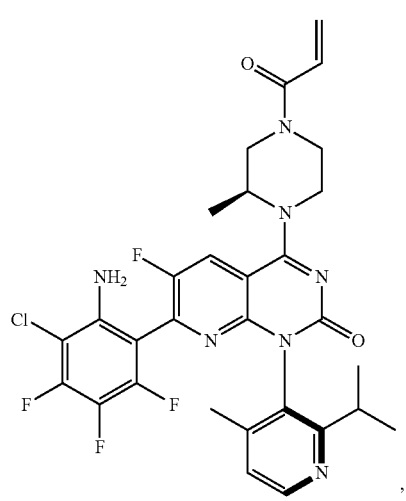
,
158
-continued
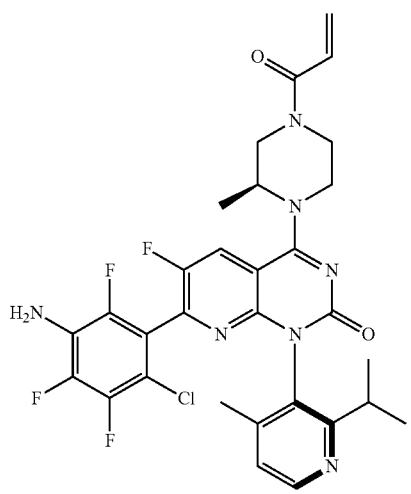
,
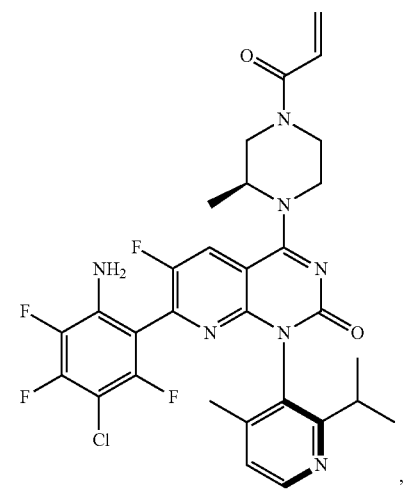
,
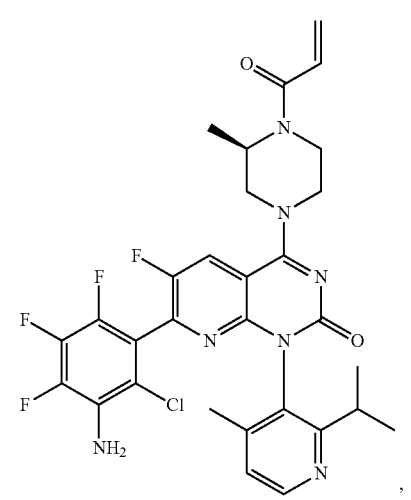
, 159
-continued
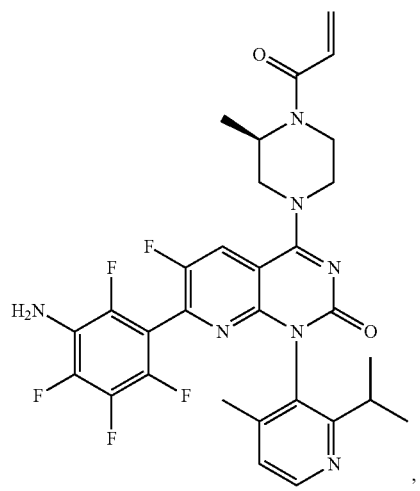
,
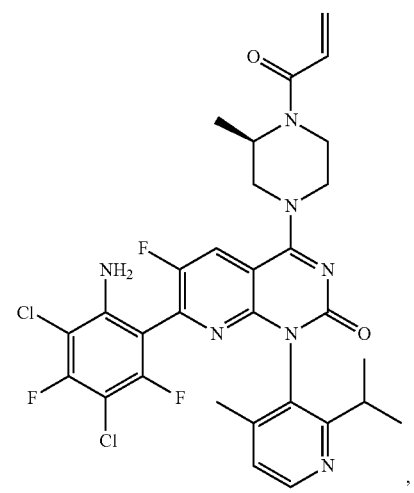
,
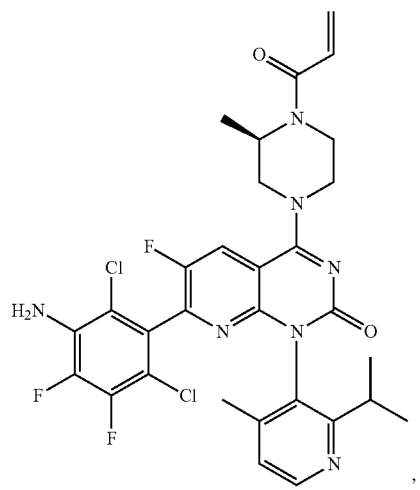
,
160
-continued
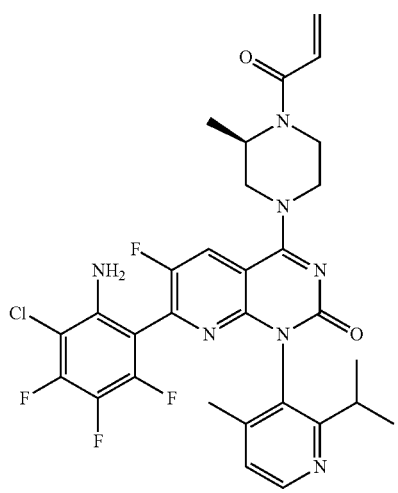
,
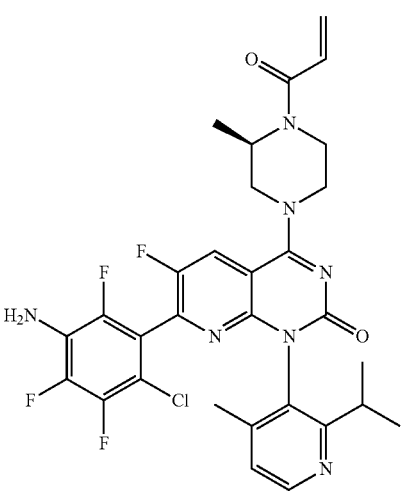
,
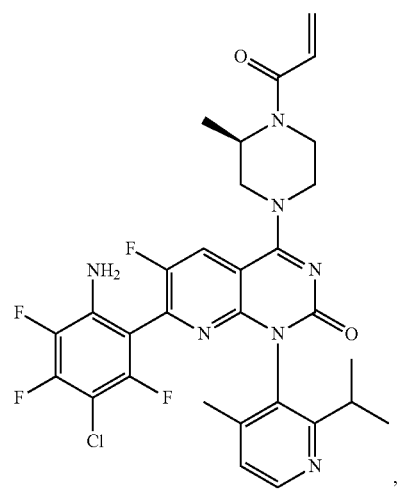
, 161
-continued
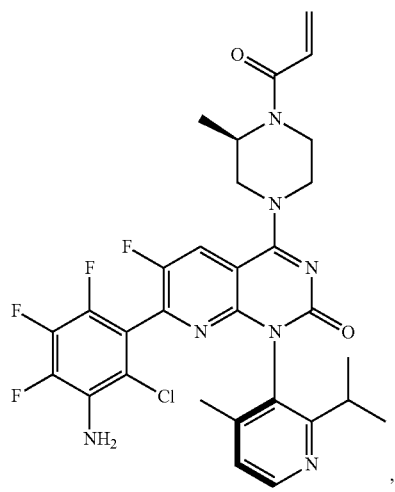
,
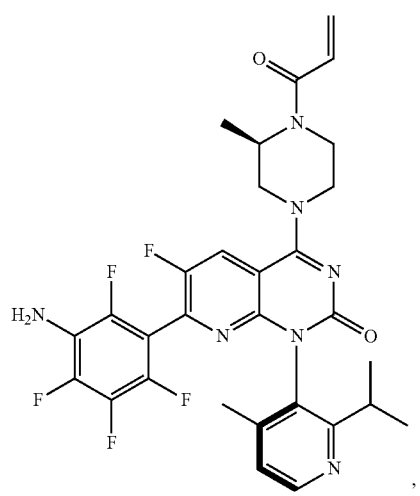
,
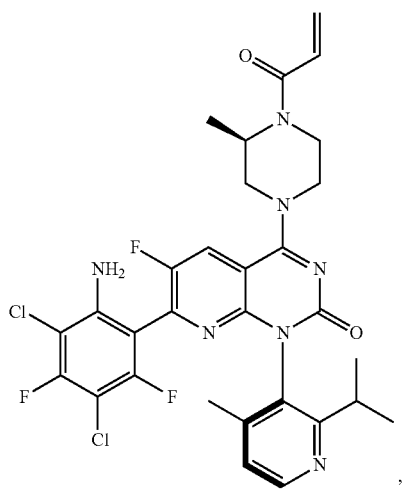
,
162
-continued
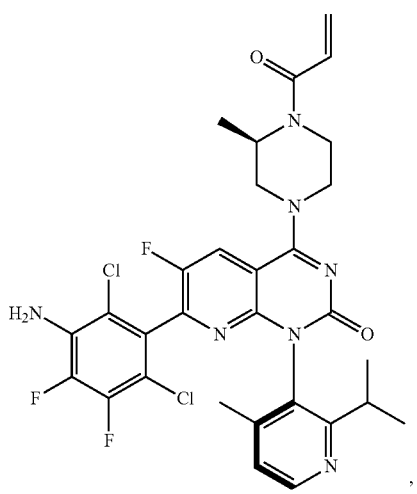
,
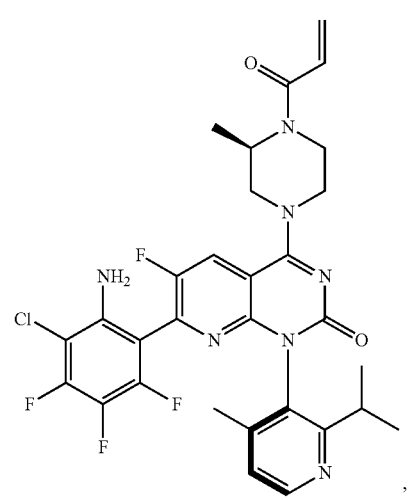
,
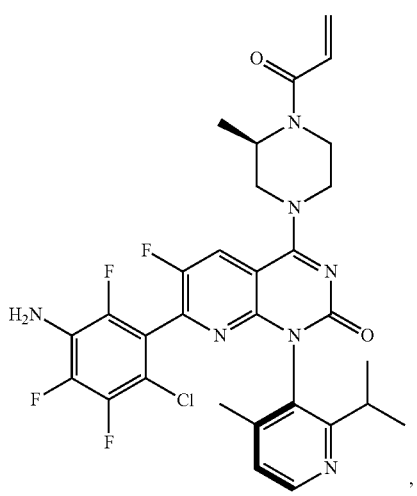
, 163
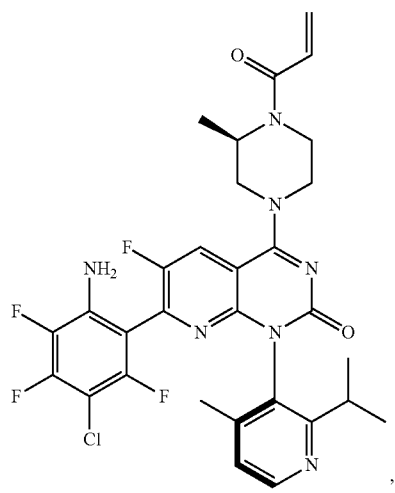
,
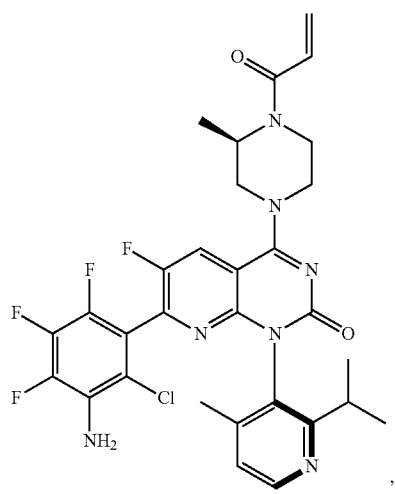
,
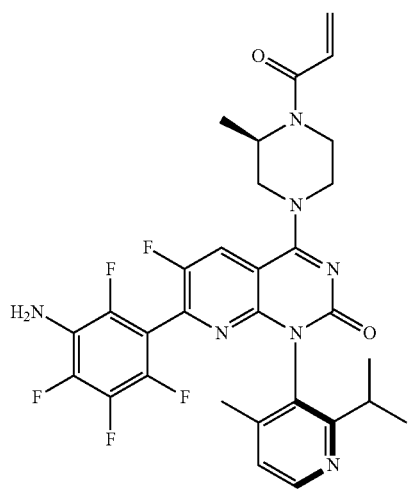
,
164
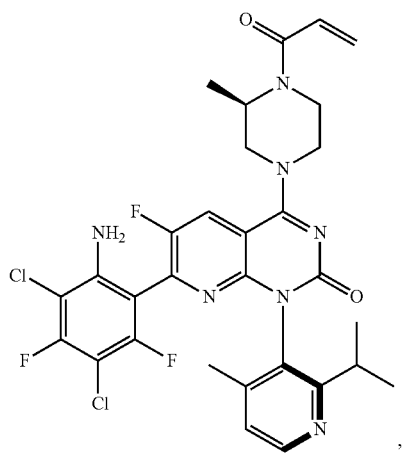
,
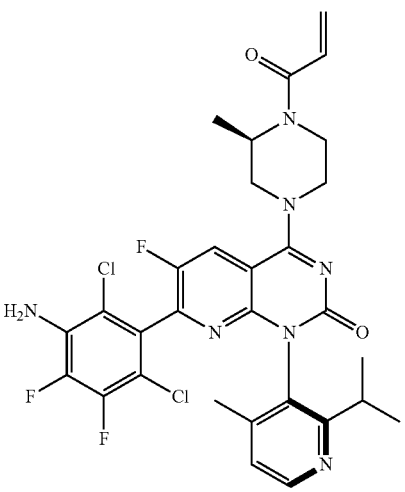
,
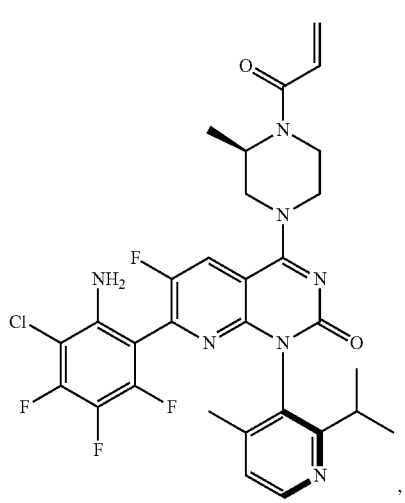
, 165
-continued
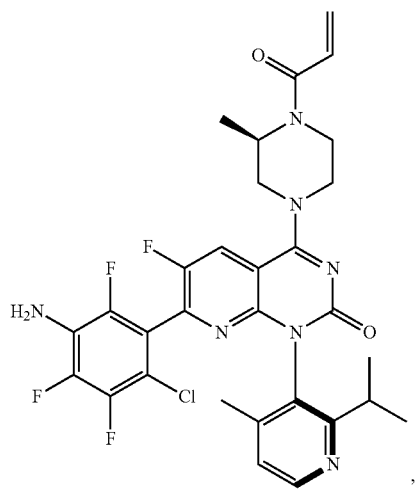
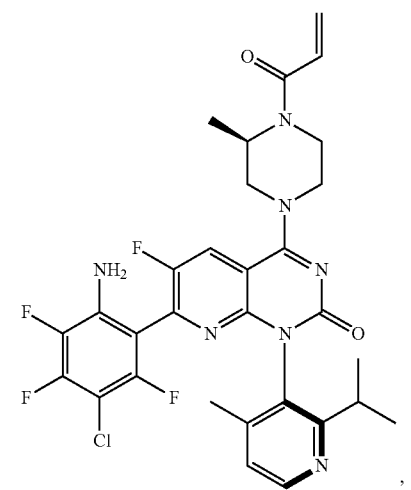
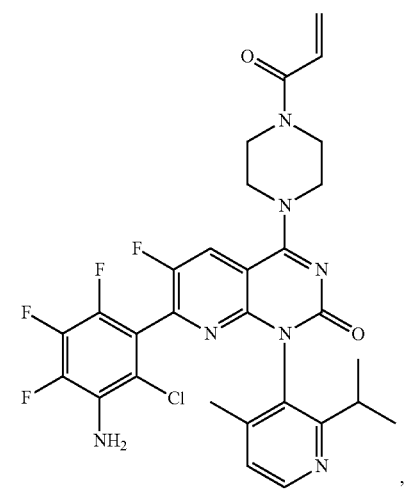
166
-continued
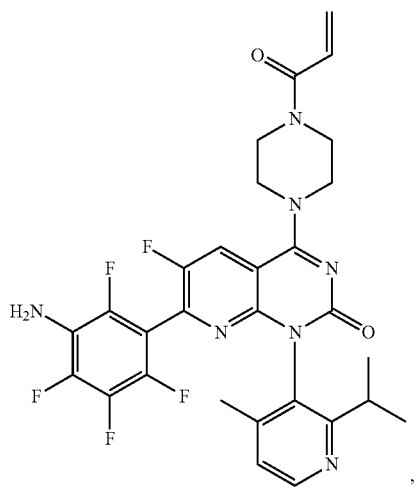
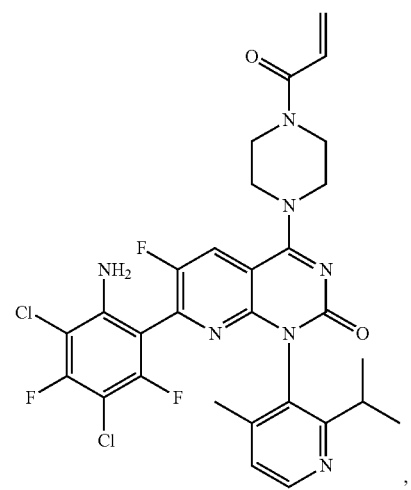
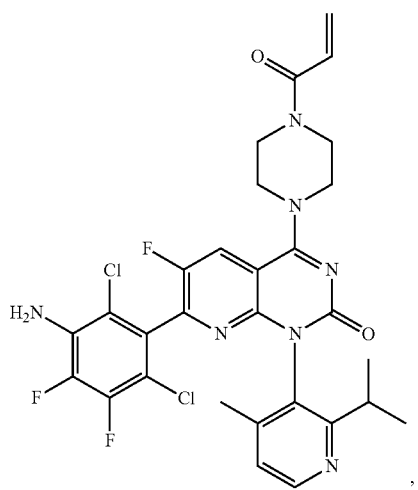

167
-continued
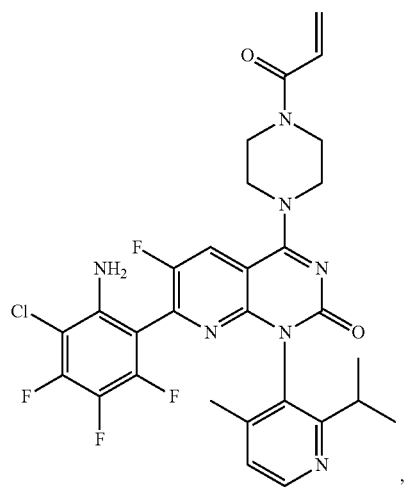
,
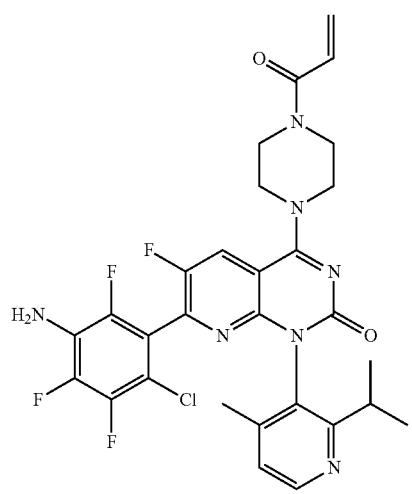
,
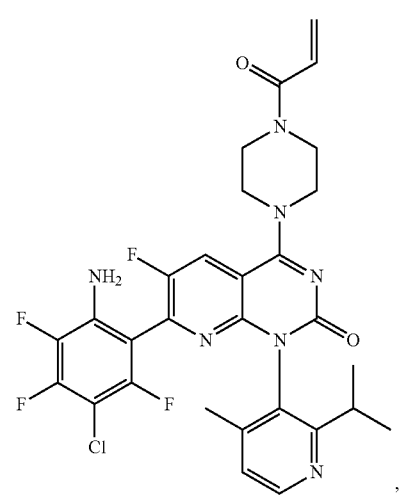
,
168
-continued
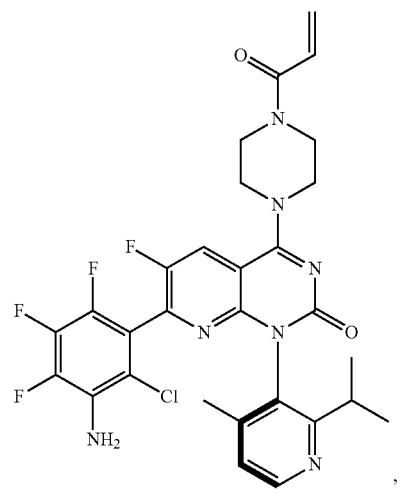
,
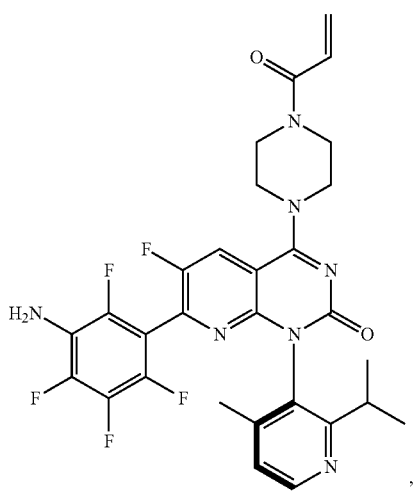
,
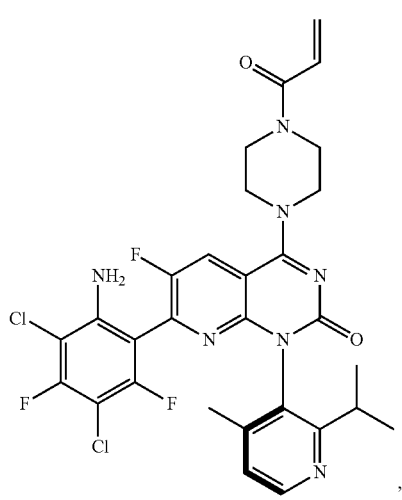
, 169
-continued
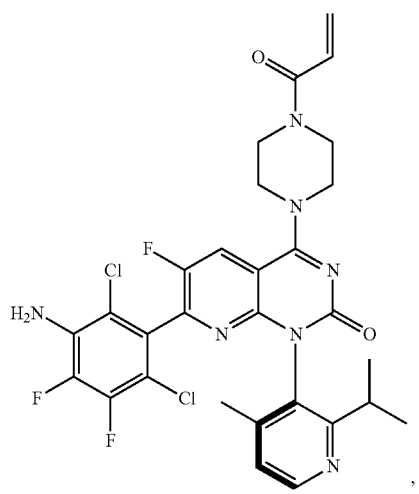
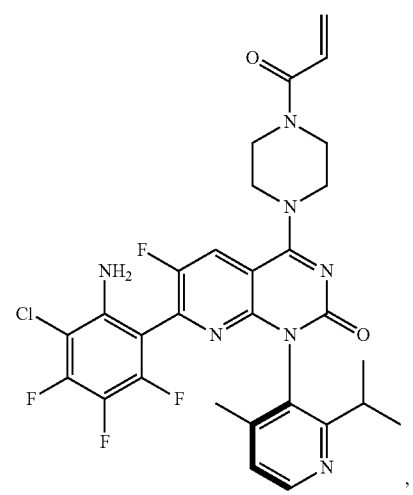
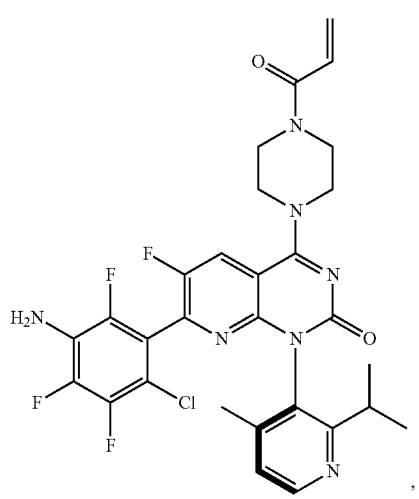
170
-continued
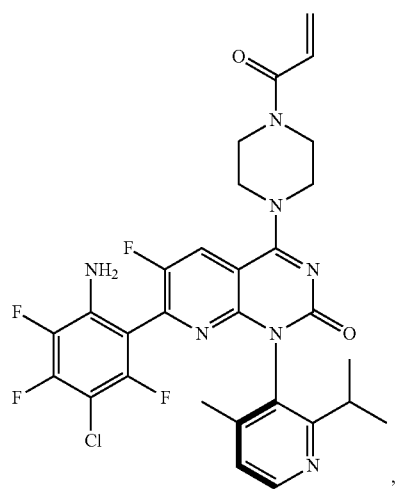
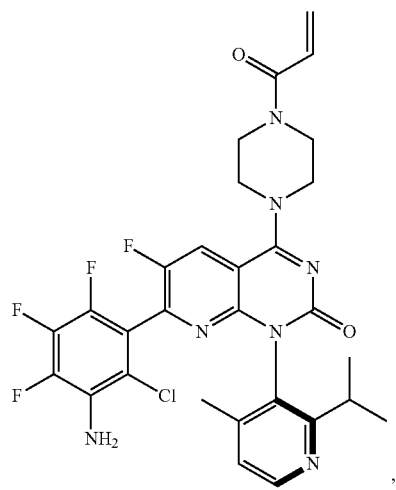
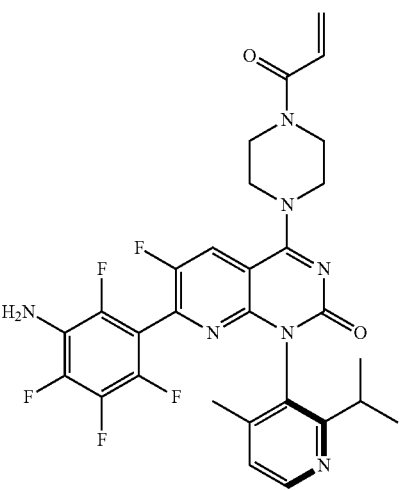

171
-continued
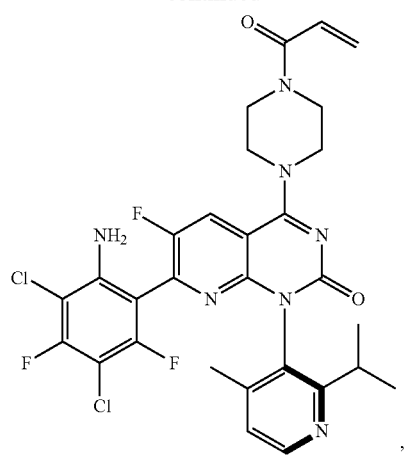
,
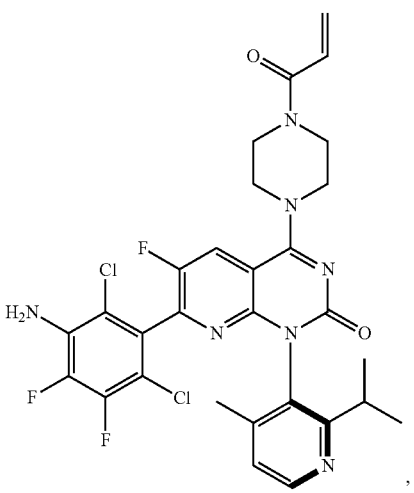
,
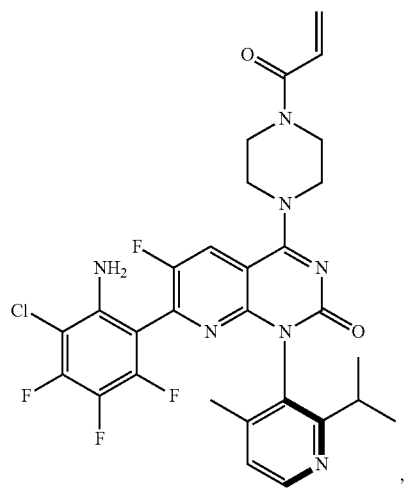
,
172
-continued
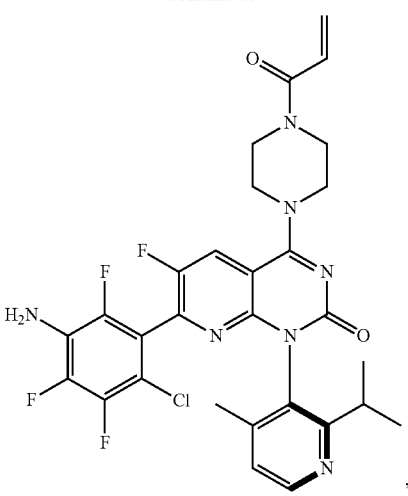
,
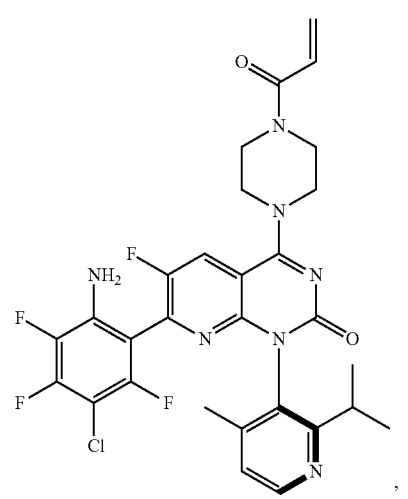
,
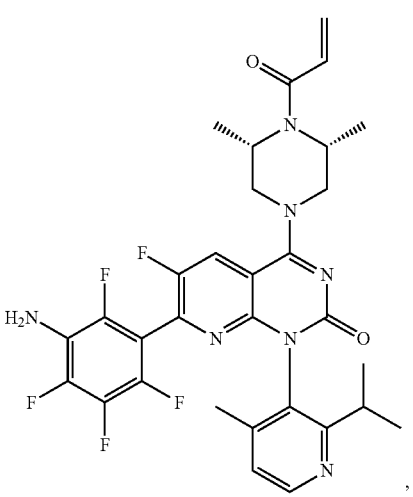
, 173
-continued
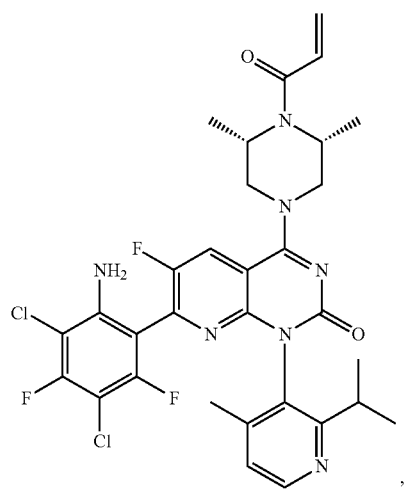
,
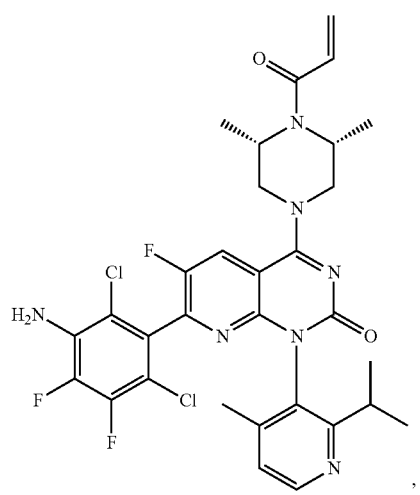
,
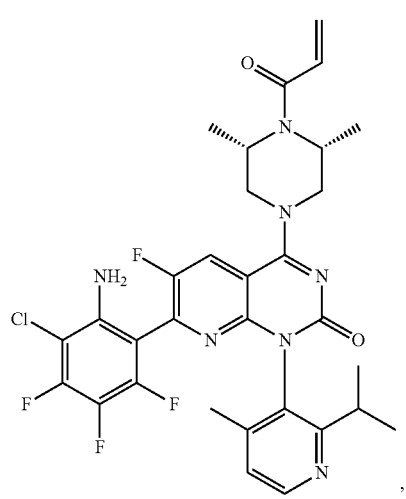
,
174
-continued
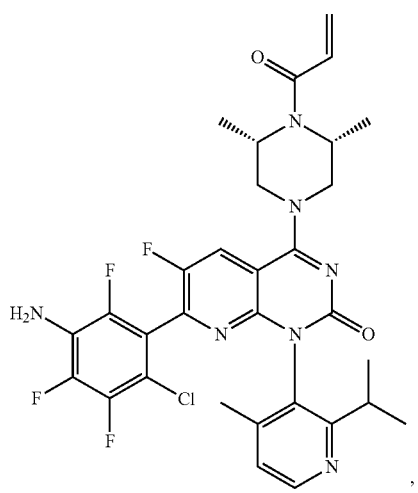
,
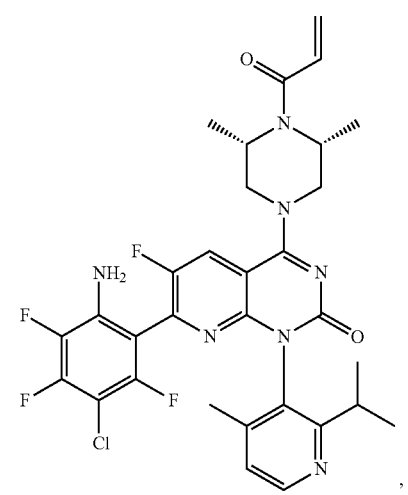
,
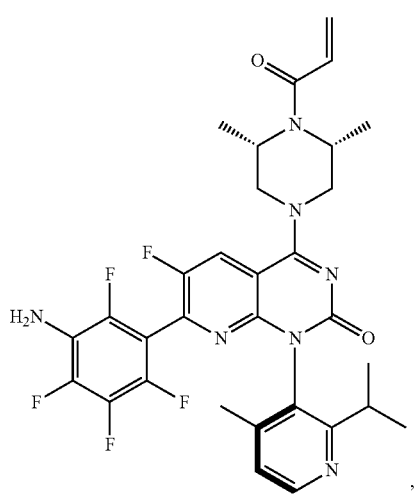
, 175
-continued
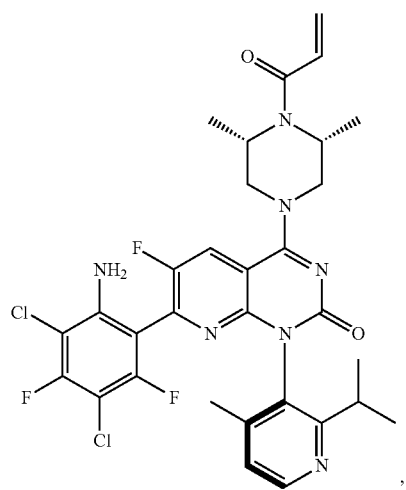
,
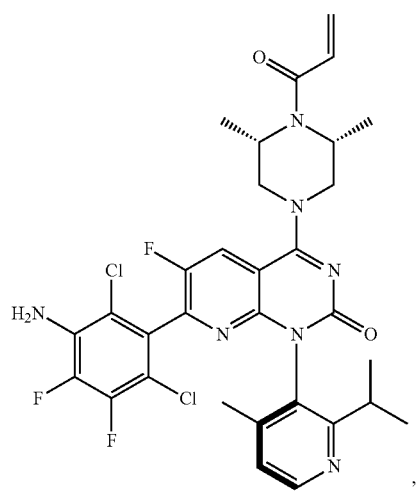
,
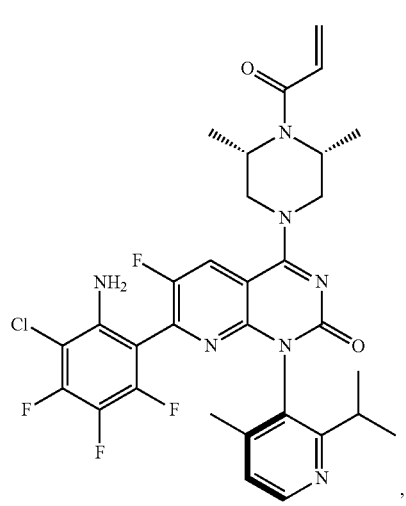
,
176
-continued
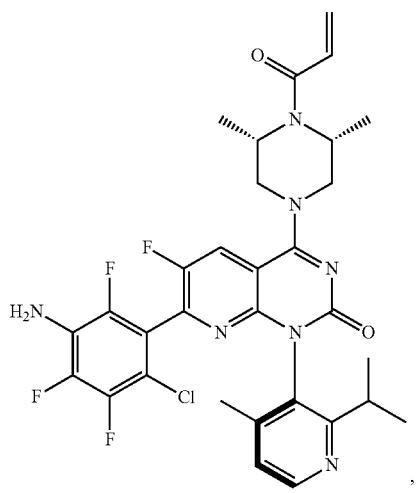
,
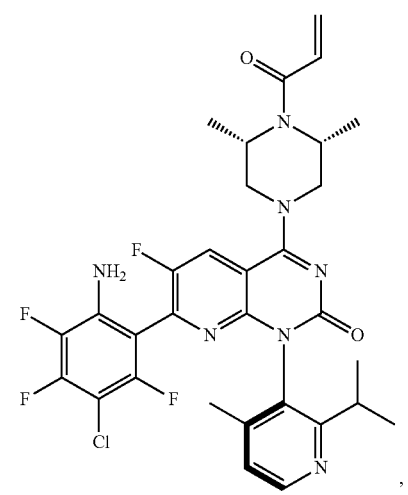
,
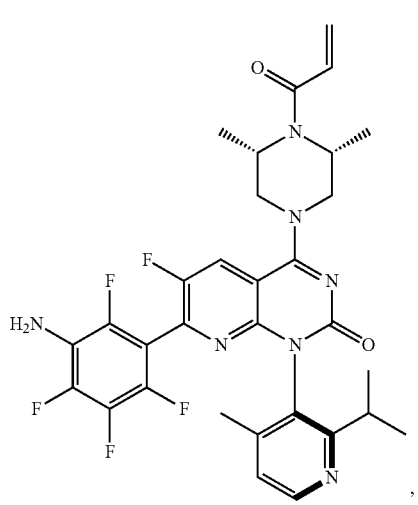
, 177
-continued
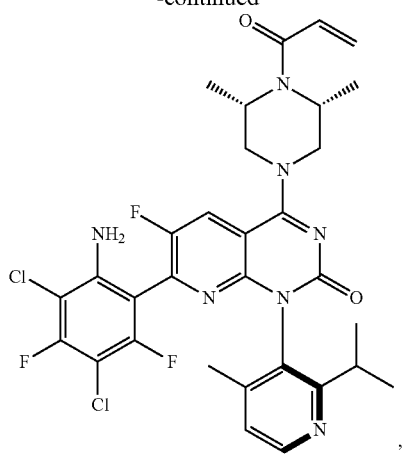
,
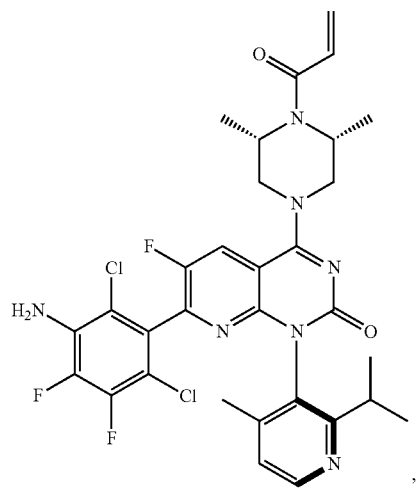
,
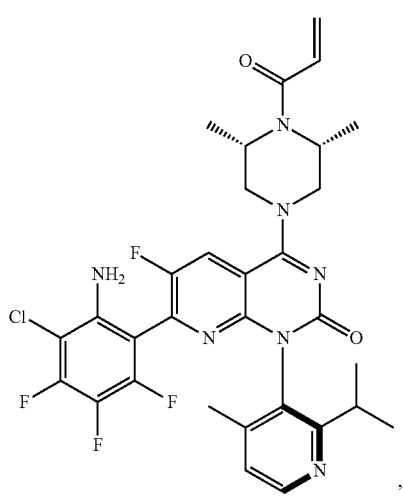
,
178
-continued
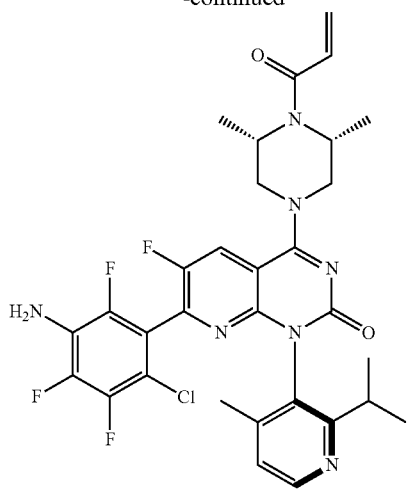
or
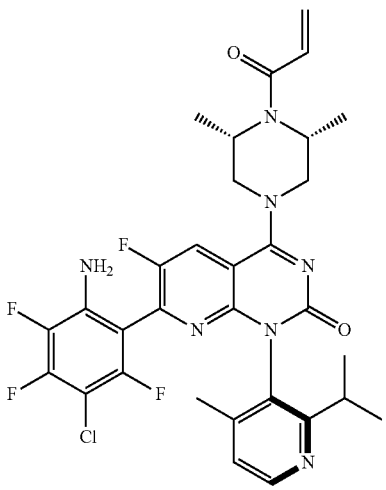
.
9. The compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof according to claim 1, wherein:

the compound is selected from:

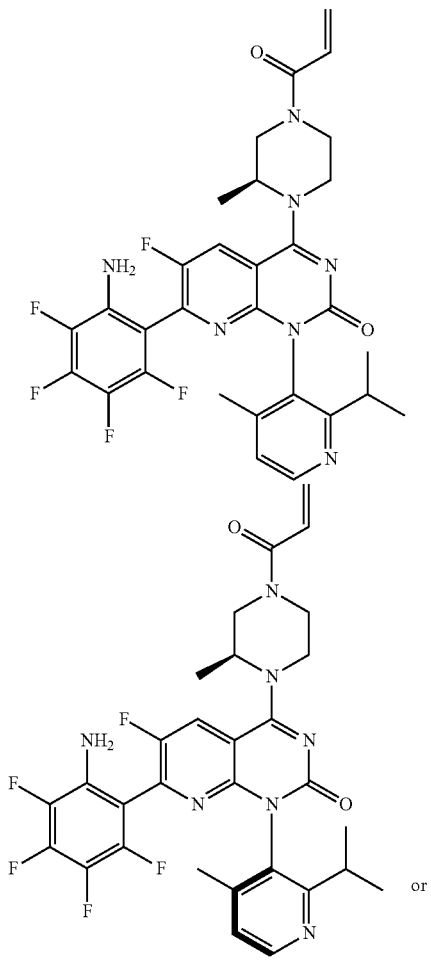

or

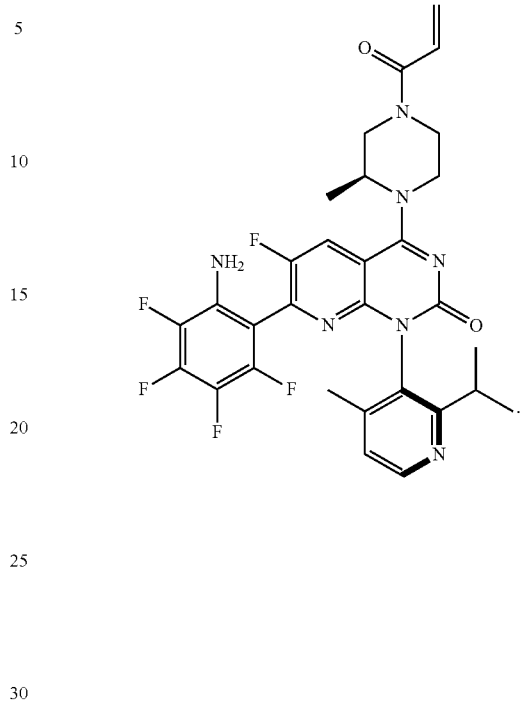

10. A pharmaceutical composition comprising the compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof according to claim 1, and at least one pharmaceutically acceptable excipient.

* * * * *